US008512964B2

(12) United States Patent
Tontonoz et al.

(10) Patent No.: US 8,512,964 B2
(45) Date of Patent: Aug. 20, 2013

(54) TARGETS FOR TREATMENT OF HYPERCHOLESTEROLEMIA

(75) Inventors: Peter J. Tontonoz, Pacific Palisades, CA (US); Noam Zelcer, Amstelveen (NL)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/132,296

(22) PCT Filed: Dec. 11, 2009

(86) PCT No.: PCT/US2009/067747
§ 371 (c)(1),
(2), (4) Date: Aug. 4, 2011

(87) PCT Pub. No.: WO2010/068918
PCT Pub. Date: Jun. 17, 2010

(65) Prior Publication Data
US 2011/0318367 A1     Dec. 29, 2011

Related U.S. Application Data

(60) Provisional application No. 61/122,273, filed on Dec. 12, 2008.

(51) Int. Cl.
*G01N 33/53* (2006.01)
*C07K 14/435* (2006.01)

(52) U.S. Cl.
USPC ................ 435/7.1; 435/6.18; 435/9; 530/350

(58) Field of Classification Search
None
See application file for complete search history.

(56) References Cited

U.S. PATENT DOCUMENTS

| 7,300,754 B2 | 11/2007 | Fadel et al. |
| 2004/0092573 A1 | 5/2004 | Robl et al. |
| 2005/0159362 A1 | 7/2005 | Sircar et al. |
| 2009/0163434 A1 | 6/2009 | Bader et al. |
| 2009/0192111 A1 | 7/2009 | Bader et al. |
| 2009/0214477 A1 | 8/2009 | Betz et al. |

FOREIGN PATENT DOCUMENTS

| WO | WO 2008/154423 | 12/2008 |
| WO | WO 2010/068918 | 6/2010 |

OTHER PUBLICATIONS

Nagano et al (2006; The EMBO Journal. 25: 1871-1882).*
International Search Report and Written Opinion dated Aug. 23, 2010 issued in WO/2010/068918 (PCT/US2009/067747).
International Preliminary Report on Patentability dated Jun. 14, 2011 issued in WO/2010/068918 (PCT/US2009/067747).
Abifadel et al. (2003) "Mutations in PCSK9 cause autosomal dominant hypercholesterolemia." *Nature Genetics* 34(2): 154-156.
Adams et al. (2004) "Cholesterol and 25-Hydroxycholesterol Inhibit Activation of SREBPs by Different Mechanisms, Both Involving SCAP and Insigs." *The Journal of Biological Chemistry* 279(50): 52772-52780.
Anderson et al. (1984) "Glycophorin is linked by band 4.1 protein to the human erythrocyte membrane skeleton." *Letter to Nature* 307: 655-658.
Bensinger et al. (2008) "LXR Signaling Couples Sterol Metabolism to Proliferation in the Acquired Immune Response." *Cell* 134: 97-111.
Bornhauser et al. (2003) "Functional activities and cellular localization of the ezrin, radixin, moesin (ERM) and Ring zinc ¢nger domains in MIR." *FEBS Letters* 553: 195-199.
Bretscher et al. (2002) "ERM Proteins and Merlin: Integrators at the Cell Cortex." *Nature Reviews* 3: 586-599.
Brown et al. (1986) "A Receptor-Mediated Pathway for Cholesterol Homeostasis." *Science* 232(4746): 34-47.
Cadwell et al. (2005) "Ubiquitination on Nonlysine Residues by a Viral E3 Ubiquitin Ligase." *Science* 309: 127-130.
Chen et al. (2007) "Enzymatic Reduction of Oxysterols Impairs LXR Signaling in Cultured Cells and the Livers of Mice." *Cell Metabolism* 5: 73-79.
Cohen et al. (2003) "Molecular mechanisms of autosomal recessive hypercholesterolemia." *Current Opinion in Lipidology* 14: 121-127.
Cohen et al. (2005) "Low LDL cholesterol in individuals of African descent resulting from frequent nonsense mutations in PCSK9." *Nature Genetics* 37(2): 161-165.
Garcia et al. (2001) "Autosomal Recessive Hypercholesterolemia Caused by Mutations in a Putative LDL Receptor Adaptor Protein." *Science* 292: 1394-1398.
Goldstein et al. (2006) "Autosomal Recessive Hypercholesterolemia Caused by Mutations in a Putative LDL Receptor Adaptor Protein." *Cell* 124: 35-46.
Hobbs et al. (1990) "The LDL Receptor Locus in Familial Hypercholesterolemia." *Annu. Rev. Genet* 24: 133-70.
Hua et al. (1993) "SREBP-2, a second basic-helix-loop-helix-leucine zipper protein that stimulates transcription by binding to a sterol regulatory element." *Proc. Natl. Acad. Sci.* 90: 11603-11607.
Joseph et al. (2002) "Synthetic LXR ligand inhibits the development of atherosclerosis in mice." *Proc. Natl. Acad. Sci.* 99(11): 7604-7609.
Kennedy et al. (2005) "ABCG1 has a critical role in mediating cholesterol efflux to HDL and preventing cellular lipid accumulation." *Cell Metabolism* 1: 121-131.
Lindholm et al. (2009) "Mylip makes an Idol turn into regulation of 13-19,23-76 LDL receptor." *Cell. Mol. Life Sci.* 66: 3399-3402.
Maxwell et al. (2004) "Adenoviral-mediated expression of Pcsk9 in mice results in a low-density lipoprotein receptor knockout phenotype." *Proc. Natl. Acad. Sci.* 101(18): 7100-7105.
Maxwell et al. (2005) "Overexpression of PCSK9 accelerates the degradation of the LDLR in a post-endoplasmic reticulum compartment." *Proc. Natl. Acad. Sci.* 102(6): 2069-2074.
Olsson et al. (1999) "MIR Is a Novel ERM-like Protein That Interacts with Myosin Regulatory Light Chain and Inhibits Neurite Outgrowth" *The Journal of Biological Chemistry* 274(51): 36288-36292.
Park et al. (2004) "Post-transcriptional Regulation of Low Density Lipoprotein Receptor Protein by Proprotein Convertase Subtilisin/Kexin Type 9a in Mouse Liver" *The Journal of Biological Chemistry* 279(48): 50630-50638.

(Continued)

*Primary Examiner* — Zachary Howard
(74) *Attorney, Agent, or Firm* — Tom Hunter; Weaver Austin Villeneuve & Sampson LLP

(57) ABSTRACT

In certain embodiments this invention pertains to the discovery that inhibition of myosin light chain interacting protein (Mylip) can mitigate one or more symptoms of hypercholesterolemia. Methods of treating hypercholesterolemia and methods of screening for agents to treat hypercholesterolemia are provided.

10 Claims, 22 Drawing Sheets

(56) References Cited

OTHER PUBLICATIONS

Peet et al. (1998) "Cholesterol and Bile Acid Metabolism Are Impaired in Mice Lacking the Nuclear Oxysterol Receptor LXRα" *Cell* 93: 693-704.

Repa et al. (2000) "Regulation of Absorption and ABC1-Mediated Efflux of Cholesterol by RXR Heterodimers" *Science* 289: 1524-1529.

Russell et al. (1984) "Domain Map of the LDL Receptor: Sequence Homology with the Epidermal Growth Factor Precursor" *Cell* 37: 577-585.

Schulman (2009) "Cholesterol Worships a New Idol." *Journal of Molecular Cell Biology* 1: 75-76.

Seidah et al. (2003) "The secretory proprotein convertase neural apoptosis-regulated convertase 1 (NARC-1): Liver regeneration and neuronal differentiation" *Proc. Natl. Acad. Sci.* 100(3): 928-933.

Sharkey et al. (1990) "Post-transcriptional regulation of retroviral vectortransduced low density lipoprotein receptor activity" *Journal of Lipid Research* 31: 2167-2178.

Tangirala et al. (2002) "Identification of macrophage liver X receptors as inhibitors of atherosclerosis" *Proc. Natl. Acad. Sci.* 99(18): 11896-11901.

Tolleshaug et al. (1983) "The LDL Receptor Locus in Familial Hypercholesterolemia: Multiple Mutations Disrupt Transport and Processing of a Membrane Receptor" *Cell* 32: 941-951.

Yokoyama et al. (1993) "SREBP-1, a Basic-Helix-Loop-Helix-Leucine Zipper Protein That Controls Transcription of the Low Density Lipoprotein Receptor Gene" *Cell* 75: 187-197.

Zhang et al. (2007) "Binding of Proprotein Convertase Subtilisin/Kexin Type 9 to Epidermal Growth Factor-like Repeat A of Low Density Lipoprotein Receptor Decreases Receptor Recycling and Increases Degradation" *The Journal of Biological Chemistry* 282(25): 18602-18612.

Zelcer et al. (2006) "Liver X receptors as integrators of metabolic and inflammatory signaling" *The Journal of Clinical Investigation* 116(3): 607-614.

Zelcer et al. (2009) "LXR Regulates Cholesterol Uptake Through Idol-Dependent Ubiquitination of the LDL Receptor" *Science* 325(5936): 100-104.

EP Supplementary Search Report dated Jun. 28, 2012 issued in EP09832652.3.

* cited by examiner

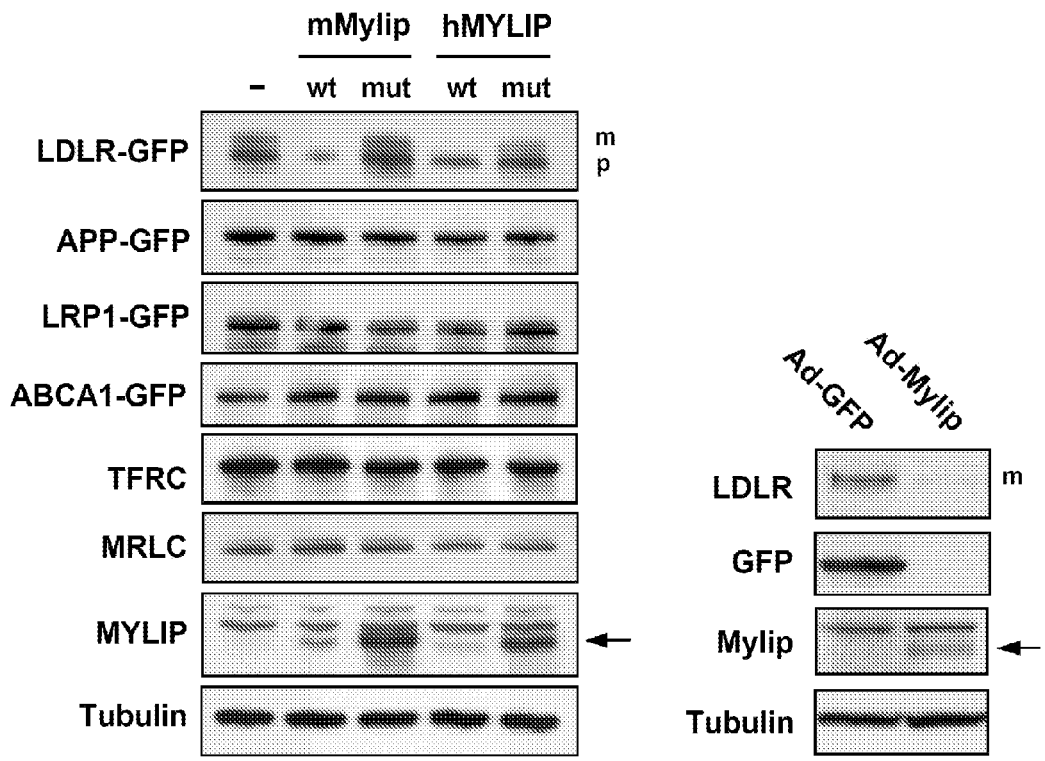
Fig. 2F
Fig. 2G
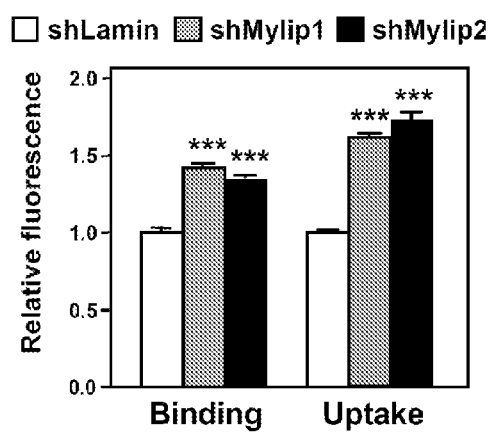
Fig. 2J
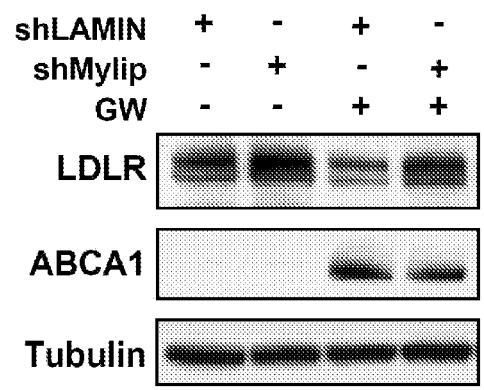
Fig. 2K

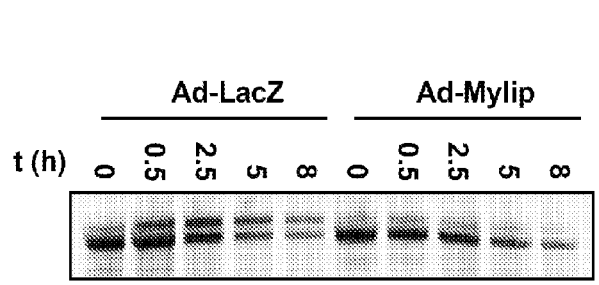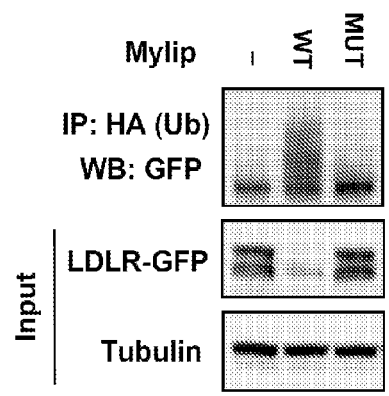

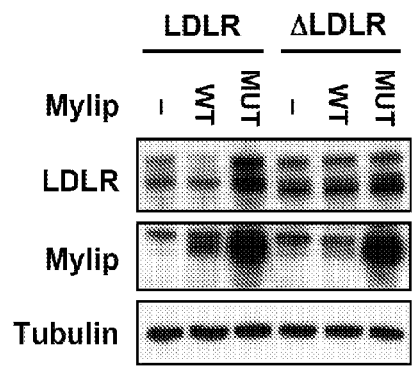

*Fig. 3C*

```
                   1     6                 20       28 29
                   |     |                 |        | |
H.Sapiens    -NWRLNINSINFDNPVYQTTEDEVHIHNQDGYSYPSRQMVSLEDDVA-C
P.troglodytes -NWRLNINSINFDNPVYQTTEDEVHIRNQDGYSYPSRQMVSLEDDVA-C
R.norvegicus -RNWRLRNINSINFDNPVYQTTEDEIHIRSQDGYTYPSRQMVSLEDDVA-C
M.musculus   -RNWRLNINSINFDNPVYQTTEDELHIRSQDGYTYPSRQMVSLEDDVA-C
O.cuniculus  -NWRLRSVHSINFDNPVYQTTEDEVHIRSQDGYTYPSRQMVSLEDDVA-C
```

*Fig. 3D*

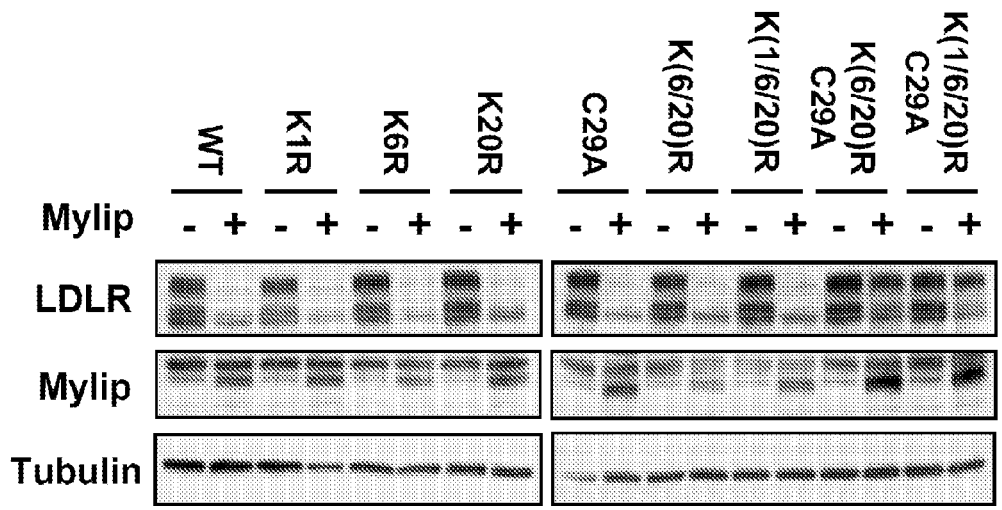
*Fig. 3E*
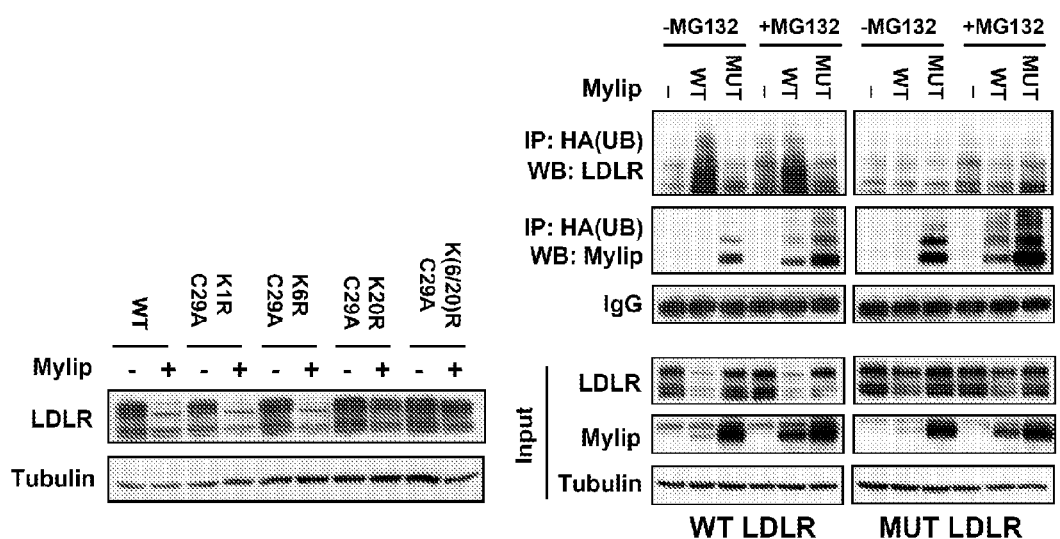
*Fig. 3F*    *Fig. 3G*

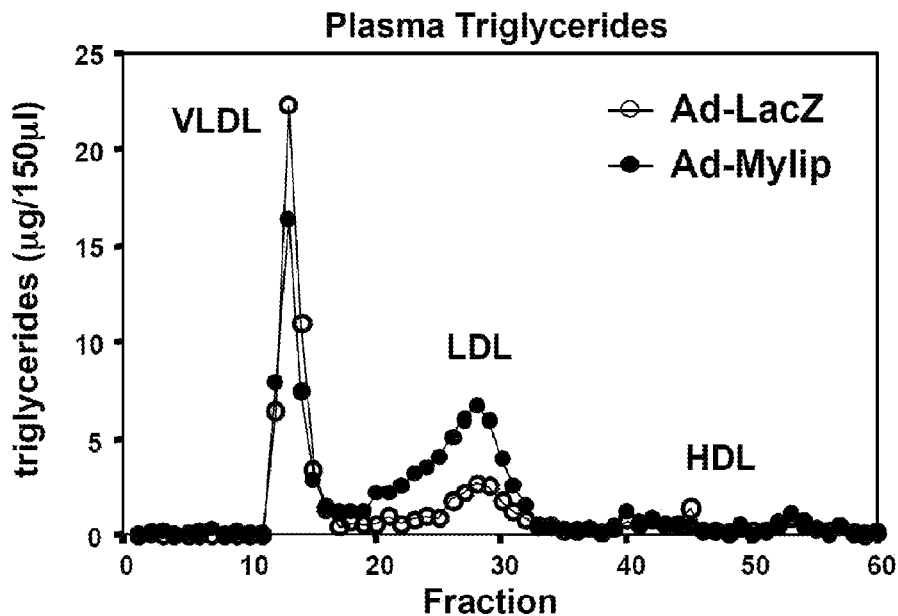
*Fig. 4C*
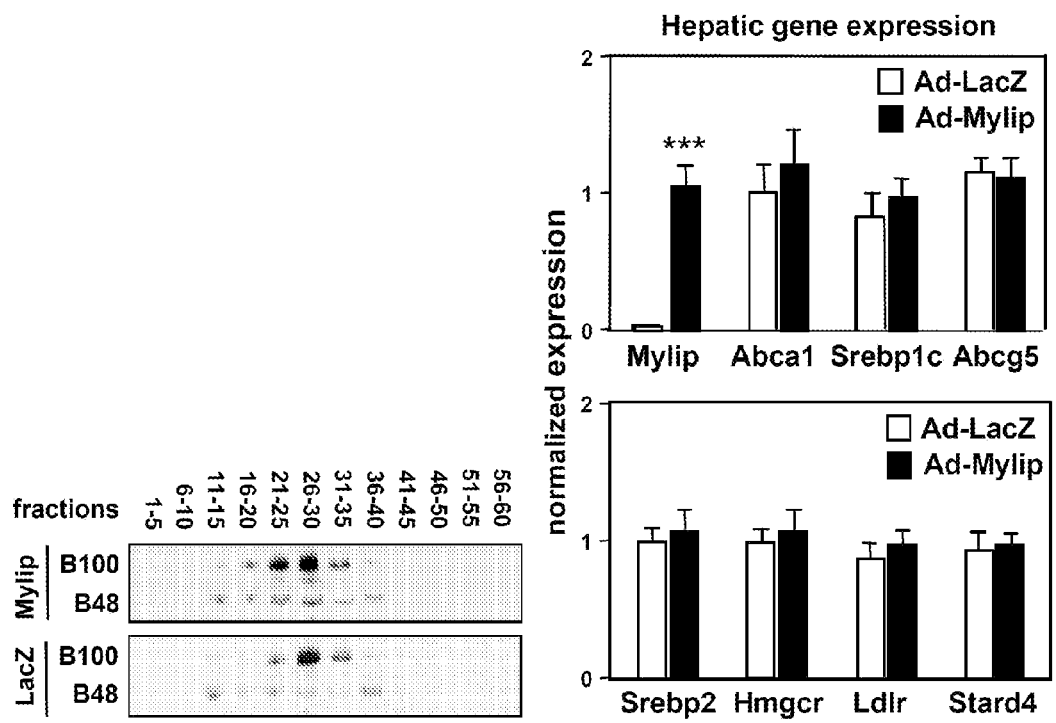
*Fig. 4D*        *Fig. 4E*

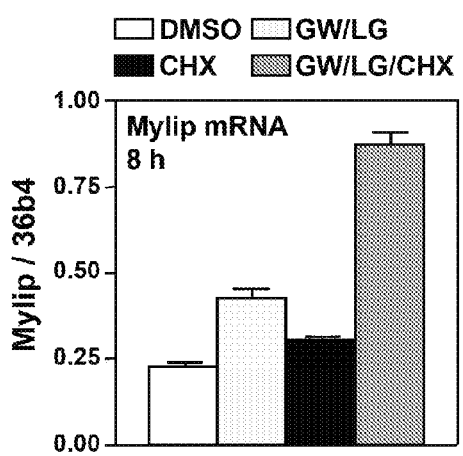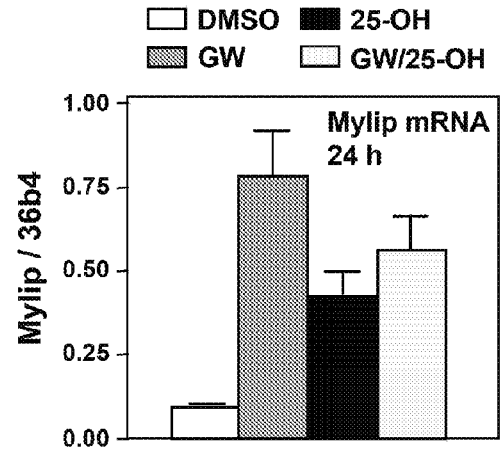
*Fig. 6A*            *Fig. 6B*
Mylip WT DR4   5-tccctactTAACCTacaaTGACCTcaagtttc-3
                      3-agggatgaATTGGAtgttACTGGAgttcaaag-5
Mylip MUT DR4   5-tccctactTATTCTacaaTGTTCTcaagtttc-3
                       3-agggatgaATAAGAtgttACAAGAgttcaaag-5
*Fig. 6C*
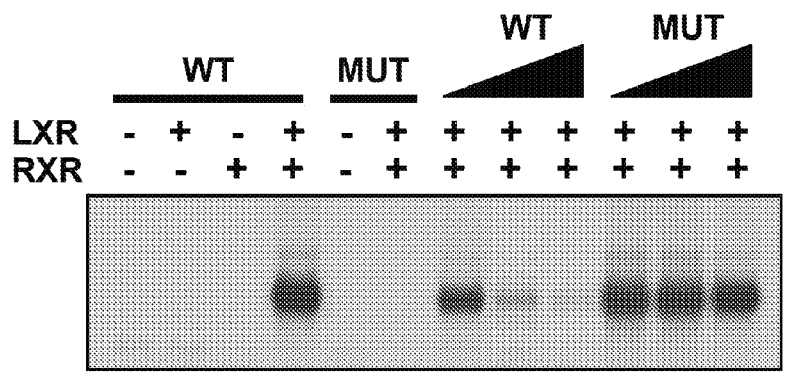
*Fig. 6E*

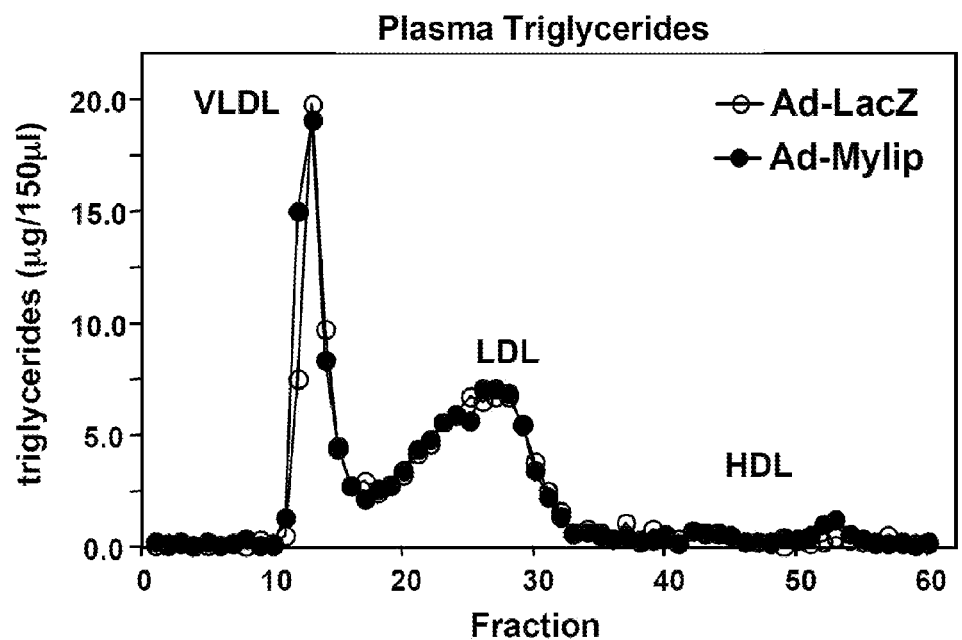
*Fig. 10E*
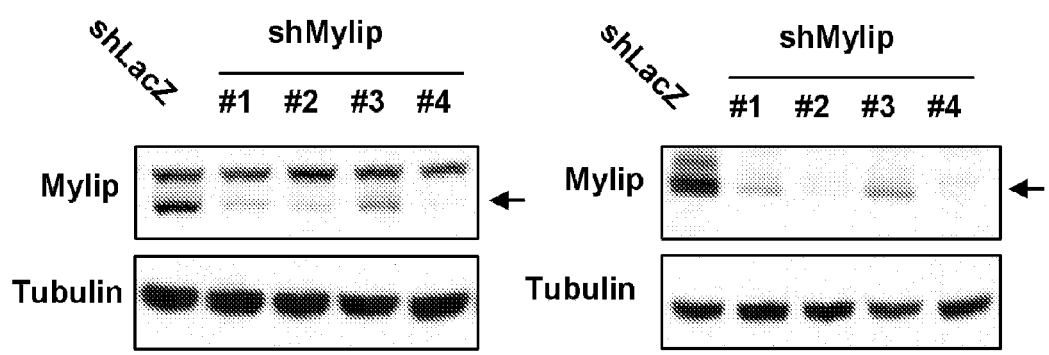
*Fig. 11A*  *Fig. 11B*

SEQUENCE LISTING

```
<160> NUMBER OF SEQ ID NOS: 42

<210> SEQ ID NO 1
<211> LENGTH: 50
<212> TYPE: PRT
<213> ORGANISM: Homo sapiens

<400> SEQUENCE: 1

Lys Asn Trp Arg Leu Lys Asn Ile Asn Ser Ile Asn Phe Asp Asn Pro
1               5                   10                  15

Val Tyr Gln Lys Thr Thr Glu Asp Glu Val His Ile Cys His Asn Gln
            20                  25                  30

Asp Gly Tyr Ser Tyr Pro Ser Arg Gln Met Val Ser Leu Glu Asp Asp
        35                  40                  45

Val Ala
    50

<210> SEQ ID NO 2
<211> LENGTH: 50
<212> TYPE: PRT
<213> ORGANISM: Pan groglodytes

<400> SEQUENCE: 2
```

-continued

Lys Asn Trp Arg Leu Lys Asn Ile Asn Ser Ile Asn Phe Asp Asn Pro
1               5                   10                  15

Val Tyr Gln Lys Thr Thr Glu Asp Glu Val His Ile Cys Arg Asn Gln
            20                  25                  30

Asp Gly Tyr Ser Tyr Pro Ser Arg Gln Met Val Ser Leu Glu Asp Asp
        35                  40                  45

Val Ala
    50

<210> SEQ ID NO 3
<211> LENGTH: 50
<212> TYPE: PRT
<213> ORGANISM: Rattus norvegicus

<400> SEQUENCE: 3

Arg Asn Trp Arg Leu Arg Asn Ile Asn Ser Ile Asn Phe Asp Asn Pro
1               5                   10                  15

Val Tyr Gln Lys Thr Thr Glu Asp Glu Ile His Ile Cys Arg Ser Gln
            20                  25                  30

Asp Gly Tyr Thr Tyr Pro Ser Arg Gln Met Val Ser Leu Glu Asp Asp
        35                  40                  45

Val Ala
    50

<210> SEQ ID NO 4
<211> LENGTH: 50
<212> TYPE: PRT
<213> ORGANISM: Mus musculus

<400> SEQUENCE: 4

Arg Asn Trp Arg Leu Lys Asn Ile Asn Ser Ile Asn Phe Asp Asn Pro
1               5                   10                  15

Val Tyr Gln Lys Thr Thr Glu Asp Glu Leu His Ile Cys Arg Ser Gln
            20                  25                  30

Asp Gly Tyr Thr Tyr Pro Ser Arg Gln Met Val Ser Leu Glu Asp Asp
        35                  40                  45

Val Ala
    50

<210> SEQ ID NO 5
<211> LENGTH: 50
<212> TYPE: PRT
<213> ORGANISM: Oryctolagus cuniculus

<400> SEQUENCE: 5

Lys Asn Trp Arg Leu Arg Ser Val His Ser Ile Asn Phe Asp Asn Pro
1               5                   10                  15

Val Tyr Gln Lys Thr Thr Glu Asp Glu Val His Ile Cys Arg Ser Gln
            20                  25                  30

Asp Gly Tyr Thr Tyr Pro Ser Arg Gln Met Val Ser Leu Glu Asp Asp
        35                  40                  45

Val Ala
    50

<210> SEQ ID NO 6
<211> LENGTH: 32
<212> TYPE: DNA
<213> ORGANISM: Mus musculus

<400> SEQUENCE: 6

```
tccctactta acctacaatg acctcaagtt tc                                    32

<210> SEQ ID NO 7
<211> LENGTH: 32
<212> TYPE: DNA
<213> ORGANISM: Mus musculus

<400> SEQUENCE: 7
gaaacttgag gtcattgtag gttaagtagg ga                                    32

<210> SEQ ID NO 8
<211> LENGTH: 32
<212> TYPE: DNA
<213> ORGANISM: Mus musculus

<400> SEQUENCE: 8
tccctactta ttctacaatg ttctcaagtt tc                                    32

<210> SEQ ID NO 9
<211> LENGTH: 32
<212> TYPE: DNA
<213> ORGANISM: Mus musculus

<400> SEQUENCE: 9
gaaacttgag aacattgtag aataagtagg ga                                    32

<210> SEQ ID NO 10
<211> LENGTH: 51
<212> TYPE: PRT
<213> ORGANISM: Homo sapiens

<400> SEQUENCE: 10

Leu Trp Lys Asn Trp Arg Leu Lys Asn Ile Asn Ser Ile Asn Phe Asp
1               5                   10                  15

Asn Pro Val Gln Lys Thr Thr Glu Asp Glu Val His Ile Cys His Asn
            20                  25                  30

Gln Asp Gly Tyr Ser Tyr Pro Ser Arg Gln Met Val Ser Leu Glu Asp
        35                  40                  45

Asp Val Ala
    50

<210> SEQ ID NO 11
<211> LENGTH: 56
<212> TYPE: PRT
<213> ORGANISM: Homo sapiens

<400> SEQUENCE: 11

Met Trp Arg Asn Trp Gln His Lys Asn Met Lys Ser Met Asn Phe Asp
1               5                   10                  15

Asn Pro Val Tyr Leu Lys Thr Thr Glu Glu Asp Leu Ser Ile Asp Ile
            20                  25                  30

Gly Arg His Ser Ala Ser Val Gly His Thr Tyr Pro Ala Ile Ser Val
        35                  40                  45

Val Ser Thr Asp Asp Asp Leu Ala
    50                  55

<210> SEQ ID NO 12
<211> LENGTH: 58
<212> TYPE: PRT
<213> ORGANISM: Homo sapiens

<400> SEQUENCE: 12
```

-continued

Ile Trp Arg Asn Trp Lys Arg Lys Asn Thr Lys Ser Met Asn Phe Asp
1               5                   10                  15

Asn Pro Val Tyr Arg Lys Thr Thr Glu Glu Asp Glu Asp Glu Leu
            20                  25                  30

His Ile Gly Arg Thr Ala Gln Ile Gly His Val Tyr Pro Ala Arg Val
            35                  40                  45

Ala Leu Ser Leu Glu Asp Asp Gly Leu Pro
    50                  55

<210> SEQ ID NO 13
<211> LENGTH: 57
<212> TYPE: PRT
<213> ORGANISM: Homo sapiens

<400> SEQUENCE: 13

Asn Ser Asp Leu Lys Gly Pro Leu Thr Ala Gly Pro Thr Asn Tyr Ser
1               5                   10                  15

Asn Pro Val Tyr Ala Lys Leu Tyr Met Asp Gly Gln Asn Cys Arg Asn
            20                  25                  30

Ser Leu Gly Ser Val Asp Glu Arg Lys Glu Leu Leu Pro Lys Lys Ile
            35                  40                  45

Glu Ile Gly Ile Arg Glu Thr Val Ala
    50                  55

<210> SEQ ID NO 14
<211> LENGTH: 57
<212> TYPE: PRT
<213> ORGANISM: Homo sapiens

<400> SEQUENCE: 14

Leu Asp Ala Asp Phe Ala Leu Asp Pro Asp Lys Pro Thr Asn Phe Thr
1               5                   10                  15

Asn Pro Val Tyr Ala Thr Leu Tyr Met Gly Gly His Gly Ser Arg His
            20                  25                  30

Ser Leu Ala Ser Thr Asp Glu Lys Arg Glu Leu Leu Gly Arg Gly Pro
            35                  40                  45

Glu Asp Glu Ile Gly Asp Pro Leu Ala
    50                  55

<210> SEQ ID NO 15
<211> LENGTH: 56
<212> TYPE: PRT
<213> ORGANISM: Homo sapiens

<400> SEQUENCE: 15

Glu Tyr Ile Asn Gln Ser Val Pro Lys Arg Pro Ala Gly Ser Val Gln
1               5                   10                  15

Asn Pro Val Tyr His Asn Gln Pro Leu Asn Pro Ala Pro Ser Arg Asp
            20                  25                  30

Pro His Tyr Gln Asp Pro His Ser Thr Ala Val Gly Asn Pro Glu Tyr
            35                  40                  45

Leu Asn Thr Val Gln Pro Thr Cys
    50                  55

<210> SEQ ID NO 16
<211> LENGTH: 23
<212> TYPE: DNA
<213> ORGANISM: Artificial
<220> FEATURE:
<223> OTHER INFORMATION: siRNA sequence

```
<220> FEATURE:
<221> NAME/KEY: misc_feature
<222> LOCATION: (3)..(21)
<223> OTHER INFORMATION: n is a, c, g, or t

<400> SEQUENCE: 16
aannnnnnnn nnnnnnnnnn ntt                                               23

<210> SEQ ID NO 17
<211> LENGTH: 25
<212> TYPE: DNA
<213> ORGANISM: Artificial
<220> FEATURE:
<223> OTHER INFORMATION: siRNA sequence
<220> FEATURE:
<221> NAME/KEY: misc_feature
<222> LOCATION: (3)..(23)
<223> OTHER INFORMATION: n is a, c, g, or t

<400> SEQUENCE: 17
aannnnnnnn nnnnnnnnnn nnntt                                             25

<210> SEQ ID NO 18
<211> LENGTH: 23
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (3)..(23)
<223> OTHER INFORMATION: n is a, c, g, or u

<400> SEQUENCE: 18
nannnnnnnn nnnnnnnnnn nnn                                               23

<210> SEQ ID NO 19
<211> LENGTH: 23
<212> TYPE: RNA
<213> ORGANISM: Artificial
<220> FEATURE:
<223> OTHER INFORMATION: siRNA sequence
<220> FEATURE:
<221> NAME/KEY: misc_feature
<222> LOCATION: (1)..(1)
<223> OTHER INFORMATION: n is a, c, g, or u
<220> FEATURE:
<221> NAME/KEY: misc_feature
<222> LOCATION: (4)..(20)
<223> OTHER INFORMATION: n is a, c, g, or u
<220> FEATURE:
<221> NAME/KEY: misc_feature
<222> LOCATION: (22)..(23)
<223> OTHER INFORMATION: n is a, c, g, or u

<400> SEQUENCE: 19
narnnnnnnn nnnnnnnnnn ynn                                               23

<210> SEQ ID NO 20
<211> LENGTH: 28
<212> TYPE: DNA
<213> ORGANISM: Artificial
<220> FEATURE:
<223> OTHER INFORMATION: PCR primer

<400> SEQUENCE: 20
gctagcccta cttaacctac aatgacct                                          28
```

```
<210> SEQ ID NO 21
<211> LENGTH: 28
<212> TYPE: DNA
<213> ORGANISM: Artificial
<220> FEATURE:
<223> OTHER INFORMATION: PCR primer

<400> SEQUENCE: 21
gctagcttct gatgcttcta cctctatc                                      28

<210> SEQ ID NO 22
<211> LENGTH: 25
<212> TYPE: DNA
<213> ORGANISM: Artificial
<220> FEATURE:
<223> OTHER INFORMATION: PCR primer

<400> SEQUENCE: 22
gagctcagtt cccgggagct acacg                                         25

<210> SEQ ID NO 23
<211> LENGTH: 50
<212> TYPE: DNA
<213> ORGANISM: Artificial
<220> FEATURE:
<223> OTHER INFORMATION: PCR primer

<400> SEQUENCE: 23
caccggagca aaggtgagag cttatcgaaa taagctctca cctttgctcc               50

<210> SEQ ID NO 24
<211> LENGTH: 50
<212> TYPE: DNA
<213> ORGANISM: Artificial
<220> FEATURE:
<223> OTHER INFORMATION: PCR primer

<400> SEQUENCE: 24
aaaaggagca aaggtgagag cttatttcga taagctctca cctttgctcc               50

<210> SEQ ID NO 25
<211> LENGTH: 50
<212> TYPE: DNA
<213> ORGANISM: Artificial
<220> FEATURE:
<223> OTHER INFORMATION: PCR primer

<400> SEQUENCE: 25
caccgcctta aactgagggt caagtcgaaa cttgaccctc agtttaaggc               50

<210> SEQ ID NO 26
<211> LENGTH: 50
<212> TYPE: DNA
<213> ORGANISM: Artificial
<220> FEATURE:
<223> OTHER INFORMATION: PCR primer

<400> SEQUENCE: 26
aaaagcctta aactgagggt caagtttcga cttgaccctc agtttaaggc               50

<210> SEQ ID NO 27
<211> LENGTH: 50
<212> TYPE: DNA
<213> ORGANISM: Artificial
<220> FEATURE:
<223> OTHER INFORMATION: PCR primer
```

```
<400> SEQUENCE: 27
caccggacag cgaaggacag aaactcgaaa gtttctgtcc ttcgctgtcc            50

<210> SEQ ID NO 28
<211> LENGTH: 50
<212> TYPE: DNA
<213> ORGANISM: Artificial
<220> FEATURE:
<223> OTHER INFORMATION: PCR primer

<400> SEQUENCE: 28
aaaaggacag cgaaggacag aaactttcga gtttctgtcc ttcgctgtcc            50

<210> SEQ ID NO 29
<211> LENGTH: 50
<212> TYPE: DNA
<213> ORGANISM: Artificial
<220> FEATURE:
<223> OTHER INFORMATION: PCR primer

<400> SEQUENCE: 29
caccgcatcg tgctcctgtt taagacgaat cttaaacagg agcacgatgc            50

<210> SEQ ID NO 30
<211> LENGTH: 50
<212> TYPE: DNA
<213> ORGANISM: Artificial
<220> FEATURE:
<223> OTHER INFORMATION: PCR primer

<400> SEQUENCE: 30
aaaagcatcg tgctcctgtt taagattcgt cttaaacagg agcacgatgc            50

<210> SEQ ID NO 31
<211> LENGTH: 18
<212> TYPE: DNA
<213> ORGANISM: Artificial
<220> FEATURE:
<223> OTHER INFORMATION: PCR primer

<400> SEQUENCE: 31
cgaggactgc ctcaacca                                               18

<210> SEQ ID NO 32
<211> LENGTH: 24
<212> TYPE: DNA
<213> ORGANISM: Artificial
<220> FEATURE:
<223> OTHER INFORMATION: PCR primer

<400> SEQUENCE: 32
tgcagtccaa aatagtcaac ttct                                        24

<210> SEQ ID NO 33
<211> LENGTH: 20
<212> TYPE: DNA
<213> ORGANISM: Artificial
<220> FEATURE:
<223> OTHER INFORMATION: PCR primer

<400> SEQUENCE: 33
ttcttcgtgg agcctcatct                                             20

<210> SEQ ID NO 34
<211> LENGTH: 21
```

```
<212> TYPE: DNA
<213> ORGANISM: Artificial
<220> FEATURE:
<223> OTHER INFORMATION: PCR primer

<400> SEQUENCE: 34
cctccttgat gtgcaagaaa a                                    21

<210> SEQ ID NO 35
<211> LENGTH: 20
<212> TYPE: DNA
<213> ORGANISM: Artificial
<220> FEATURE:
<223> OTHER INFORMATION: PCR primer

<400> SEQUENCE: 35
atgaggagct ctgtgccaag                                      20

<210> SEQ ID NO 36
<211> LENGTH: 22
<212> TYPE: DNA
<213> ORGANISM: Artificial
<220> FEATURE:
<223> OTHER INFORMATION: PCR primer

<400> SEQUENCE: 36
tccttatgtt ttgcaacaat gc                                   22

<210> SEQ ID NO 37
<211> LENGTH: 21
<212> TYPE: DNA
<213> ORGANISM: Artificial
<220> FEATURE:
<223> OTHER INFORMATION: PCR primer

<400> SEQUENCE: 37
tgtggagcct catctcatct t                                    21

<210> SEQ ID NO 38
<211> LENGTH: 23
<212> TYPE: DNA
<213> ORGANISM: Artificial
<220> FEATURE:
<223> OTHER INFORMATION: PCR primer

<400> SEQUENCE: 38
agggactctt taatgtgcaa gaa                                  23

<210> SEQ ID NO 39
<211> LENGTH: 22
<212> TYPE: DNA
<213> ORGANISM: Artificial
<220> FEATURE:
<223> OTHER INFORMATION: PCR primer

<400> SEQUENCE: 39
cagctatgag gacctgtgtg ag                                   22

<210> SEQ ID NO 40
<211> LENGTH: 20
<212> TYPE: DNA
<213> ORGANISM: Artificial
<220> FEATURE:
<223> OTHER INFORMATION: PCR primer

<400> SEQUENCE: 40
tccttatgct tcgcaacgat                                      20
```

```
<210> SEQ ID NO 41
<211> LENGTH: 22
<212> TYPE: DNA
<213> ORGANISM: Artificial
<220> FEATURE:
<223> OTHER INFORMATION: PCR primer

<400> SEQUENCE: 41
aggagatcaa ctccaccttc tg                                              22

<210> SEQ ID NO 42
<211> LENGTH: 18
<212> TYPE: DNA
<213> ORGANISM: Artificial
<220> FEATURE:
<223> OTHER INFORMATION: PCR primer

<400> SEQUENCE: 42
atctgcagac cggacagg                                                   18
```

TARGETS FOR TREATMENT OF HYPERCHOLESTEROLEMIA

CROSS-REFERENCE TO RELATED APPLICATIONS

This application is a 371 National Phase of PCT/US2009/067747, filed on Dec. 11, 2009, which claims benefit of and priority to U.S. Ser. No. 61/122,273, filed on Dec. 12, 2008, which is incorporated herein by reference in its entirety for all purposes.

STATEMENT OF GOVERNMENTAL SUPPORT

This invention was made with Government support under Grant No. R01 HL066088, awarded by the National Institutes of Health. The Government has certain rights in this invention.

FIELD OF THE INVENTION

The present invention relates to the field of lipid metabolism. In particular, in certain embodiments, this invention pertains to the discovery that inhibition of myosin light chain interacting protein (Mylip) can mitigate one or more symptoms of hypercholesterolemia.

BACKGROUND OF THE INVENTION

Elevated levels of cholesterol, and particularly of low-density lipoprotein (LDL) cholesterol, are a major risk factor for the development of cardiovascular disease, the leading cause of mortality in the developed world. Current treatments include lifestyle and dietary changes and the use of oral medication belonging, mainly, to the statin class of drugs. Statins inhibit the rate-limiting enzyme in the cholesterol biosynthetic pathway, HMG-CoA, which results in increased LDL-receptor (LDLR) levels and clearance of plasma LDL. Despite their widespread use statins reduce LDL by only 30-50%. Additionally, their use results in several common side effects including muscle pain, nausea, diarrhea, or constipation, but in rare cases statins may cause liver damage or life-threatening rhabdomyolysis. Therefore, alternatives, or additives to statin treatment would prove beneficial in treating hypercholesterolemia.

SUMMARY OF THE INVENTION

It was a surprising discovery that inhibition of that myosin light chain interacting protein (Mylip) (also known as Inducible Degrader of the LDLR or "IDOL") expression or activity can inhibit LDL receptor degradation and/or promote LDL uptake in a mammal, and/or mitigate one or more symptoms of hypercholesterolemia. Accordingly, in certain embodiments, methods of achieving these results are provided. The methods typically involve administering to a mammal in need thereof an inhibitor of Mylip expression and/or activity in an amount sufficient partially or fully produces such results.

Accordingly, in certain embodiments, methods of inhibiting LDL receptor degradation and/or promoting LDL uptake in a mammal are provided. The methods typically involve administering an agent to the mammal that inhibits expression and/or activity of myosin light chain interacting protein (Mylip) in an amount sufficient to inhibit LDL receptor degradation and/or to promote LDL uptake in the mammal.

In certain embodiments methods of mitigating one or more symptoms of hypercholesterolemia in a mammal are provided. The methods typically involve administering an agent to the mammal that inhibits expression and/or activity of myosin light chain interacting protein (Mylip) in an amount sufficient to mitigate one or more symptoms of hypercholesterolemia in the mammal.

In certain embodiments the Mylip expression and/or activity is inhibited in the liver of the mammal. In certain embodiments the mammal is a human or a non-human. In certain embodiments the mammal is a human diagnosed as having or at risk for hypercholesterolemia. In various embodiments the agent comprises an siRNA and/or an shRNA. In certain embodiments the agent comprises a molecule that binds to the FERM domain of Idol and inhibits interaction or binding of Idol with LDLR. In certain embodiments the agent comprises a molecule that binds to amino acid residues of LDLR that interact with Idol. In certain embodiments the molecule inhibits interaction with or binding of Idol to the amino acid residues conserved between the amino acid residues conserved between LDLR, VLDLR and apoER2. In certain embodiments the molecule is an antibody that binds to the FERM domain of Idol and/or the amino acid residues conserved between the amino acid residues conserved between LDLR, VLDLR and apoER2. In various embodiments the agent is administered in a unit dosage formulation. In certain embodiments the agent is combined with an excipient suitable for administration to a human. In certain embodiments the excipient is sterile.

In various embodiments compositions are provided for inhibiting LDL receptor degradation and/or promoting LDL uptake and/or for mitigating one or more symptoms of hypercholesterolemia in a mammal. Illustrative compositions comprise an agent that inhibits Mylip expression and/or activity in a mammal, where the composition is formulated for administration to a mammal.

In certain embodiments the use of an agent that inhibits Mylip expression and/or activity in the manufacture of a medicament for inhibiting LDL receptor degradation and/or promoting LDL uptake and/or for mitigating one or more symptoms of hypercholesterolemia in a mammal in a mammal is provided. In various embodiments the composition or use involves an agent that comprises an siRNA and/or an shRNA. In various embodiments the composition or use involves an agent that comprises molecule that binds to the FERM domain of Idol and inhibits interaction or binding of Idol with LDLR. In various embodiments the composition or use involves an agent comprising a molecule that inhibits interaction with or binding of Idol to amino acid residues conserved LDLR, VLDLR and apoER2. In various embodiments the composition or use involves an agent comprising an antibody that binds to the FERM domain of Idol and/or to amino acid residues conserved LDLR, VLDLR and apoER2. In various embodiments the agent is formulated with a carrier for administration to a human. In various embodiments the agent is formulated in a unit dosage formulation. In various embodiments the agent is formulated as a sterile formulation.

In certain embodiments non-human mammals are provided comprising a cell transfected with a construct that expresses Idol, whereby the Idol is expressed at a higher level in a tissue of the animal than the same animal without the construct. In certain embodiments the tissue is the liver of the mammal.

In certain embodiments viable non-human knockout animals are provided where the animals comprise a disruption in an endogenous Mylip/Idol gene, where the disruption results in the mammal exhibiting a decreased level of Idol as compared to a wild-type mammal. In certain embodiments the mammal is selected from the group consisting of a rodent, an equine, a bovine, a porcine, a lagomorph, a feline, a canine, a murine, a caprine, an ovine, and a non-human primate. In certain embodiments is a rat or a mouse. In certain embodiments the disruption is selected from the group consisting of an insertion, a deletion, a frameshift mutation, a substitution, and a stop codon. In certain embodiments the disruption comprises an insertion of an expression cassette into the endogenous Idol gene. In certain embodiments the expression cassette comprises a selectable marker. In certain embodiments the disruption is in a somatic cell. In certain embodiments the disruption is in a germ cell. In various embodiments the mammal is homozygous or heterozygous for the disrupted Mylip/Idol gene.

In various embodiments methods are also provided for screening for an agent that inhibits LDL receptor degradation and/or promotes LDL uptake in a mammal, and/or that mitigates one or more symptoms of hypercholesterolemia. In certain embodiments the methods involve contacting a cell with a test agent, and detecting the expression or activity of myosin light chain interacting protein (Mylip) where a decrease in Mylip expression or activity, e.g., as compared to the expression or activity of myosin light chain interacting protein (Mylip) in a control indicates that said test agent is an agent that inhibits LDL receptor degradation and/or promotes LDL uptake in a mammal. In certain embodiments the control comprises a cell contacted with the test agent at a lower concentration and/or the control comprises a cell that is not contacted with the test agent. In certain embodiments the detecting comprises detecting expression of a reporter gene whose expression is regulated by the myLIP promoter (e.g., by detecting Mylip mRNA from the cell). In certain embodiments the level of myLip mRNA is measured by hybridizing the mRNA to a probe that specifically hybridizes to a myLip nucleic acid. In certain embodiments the hybridizing is according to a method selected from the group consisting of a Northern blot, a Southern blot using DNA derived from a myLip RNA, an array hybridization, an affinity chromatography, and an in situ hybridization. In certain embodiments the probe is a member of a plurality of probes that forms an array of probes. In various embodiments the level of MyLip mRNA is measured using a nucleic acid amplification reaction (e.g., a realtime qPCR). In certain embodiments the amount of MyLip gene product is detected by detecting the level of MyLip protein from the cell (e.g., via a method selected from the group consisting of capillary electrophoresis, a Western blot, mass spectroscopy, ELISA, immunochromatography, and immunohistochemistry). In certain embodiments the cell is cultured ex vivo. In certain embodiments the test agent is administered to an animal comprising a cell containing a MyLip nucleic acid or a MyLip protein. In various embodiments detecting the expression or activity of myosin light chain interacting protein (Mylip) comprises detecting the activity of Mylip on an LDL receptor. In certain embodiments the cell is a cell transfected with a construct expressing a detectable LDL receptor (LDLR) and with a construct expressing an active Mylip. In certain embodiments the detecting comprises detecting the detectable LDL receptor where an increase in LDL receptor indicates inhibition of Mylip. In certain embodiments the detectable LDLR is an LDLR attached to a detectable label (e.g., an LDLR-luciferase fusion protein, or an LDLR-GFP fusion protein). In certain embodiments detecting the expression or activity of myosin light chain interacting protein (Mylip) comprises detecting Mylip auto-degredation. In certain embodiments the cell is a cell transfected with a construct expressing a detectable Mylip. In certain embodiments an increase of signal from the detectable Mylip indicates inhibition of Mylip autodegredation activity and indicates that the test agent is a Mylip inhibitor. In certain embodiments the detectable Mylip is a Mylip-luciferase fusion protein, or a Mylip-GFP fusion protein. In certain embodiments the cell is an HEK293 cell or an HepG2 cell. In certain embodiments detecting the expression or activity of myosin light chain interacting protein (Mylip) comprises detecting LDL uptake where an increase in LDL uptake is an indicator of Mylip inhibition. In certain embodiments the cell is a cell that expresses LDLR either endogenously or through transfection. In certain embodiments the cell is transfected with a construct expression Mylip. In certain embodiments the cell is contacted with labeled LDL (e.g., BODIPY-LDL) and the uptake of the LDL is determined. In certain embodiments the method is performed in a high throughput format. In various embodiments the cell is disposed in a microtiter plate. In certain embodiments the method is performed in a format selected from the group consisting of a 96 well format, a 100 well format, a 320 well format, a 384 well format, an 864 well format, and a 1536 well format.

In various embodiments methods are also provided for screening for an agent that inhibits LDL receptor degradation and/or that promotes LDL uptake and/or that mitigates one or more symptoms of hypercholesterolemia in a mammal. The methods typically involve contacting an Idol protein or a fragment thereof comprising the FERM domain with a test agent; detecting binding of the test agent to the Idol protein or fragment thereof; and scoring binding moieties as candidate agents that inhibit LDL receptor degradation and/or promote LDL uptake and/or that mitigate one or more symptoms of hypercholesterolemia in a mammal.

In various embodiments methods are provided of screening for an agent that inhibits LDL receptor degradation and/or promotes LDL uptake in a mammal and/or that mitigates one or more symptoms of hypercholesterolemia. The methods typically involve contacting an LDLR or a fragment thereof comprising the amino acid residues that interact with Idol with a test agent; detecting binding of the test agent to the LDLR or fragment thereof; and scoring binding moieties as candidate agents that inhibit LDL receptor degradation and/or promote LDL uptake and/or that mitigate one or more symptoms of hypercholesterolemia in a mammal.

In various embodiments methods are provided of screening for an agent that inhibits LDL receptor degradation and/or promotes LDL uptake in a mammal and/or that mitigates one or more symptoms of hypercholesterolemia. The methods typically involve contacting an LDLR or a fragment thereof comprising the amino acid residues that interact with Idol and/or an Idol protein or a fragment thereof comprising the FERM domain with a test agent; detecting interaction or binding of the LDLR with the Idol prtein or fragment; and scoring moieties that reduce or block LDLR/Idol interaction or binding as candidate agents that inhibit LDL receptor degradation and/or promote LDL uptake and/or that mitigate one or more symptoms of hypercholesterolemia in a mammal.

DEFINITIONS

The term microtiter plate refers to an apparatus comprising a plurality of wells within which can be disposed reagents, and/or cells, and/or nematodes or other organisms, and the like. Commercially available microtiter plates are typically commercially available in 96 well, 100 well, 320 well, a 384 well, 864 well, and 1536 well formats. The microtiter plates can be clear or opaque and can be fabricated out of low fluorescence materials.

A "genetic knock out" refers to an organism in which the normal activity/expression of one or more genes is disrupted/inhibited.

A "test agent" refers to refers to an agent that is to be screened in one or more of the assays described herein. The agent can be virtually any chemical compound. It can exist as a single isolated compound or can be a member of a chemical (e.g. combinatorial) library. In a particularly preferred embodiment, the test agent will be a small organic molecule.

The term small organic molecules refers to molecules of a size comparable to those organic molecules generally used in pharmaceuticals. The term excludes biological macromolecules (e.g., proteins, nucleic acids, etc.). In certain embodiments preferred small organic molecules range in size up to about 5000 Da, more preferably up to 2000 Da, and most preferably up to about 1000 Da.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these regions of the light and heavy chains respectively.

Antibodies exist as intact immunoglobulins or as a number of well characterized fragments produced by digestion with various peptidases or expressed de novo. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region thereby converting the (Fab')$_2$ dimer into an Fab' monomer. The Fab' monomer is essentially an Fab with part of the hinge region (see, *Fundamental Immunology*, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies, including, but are not limited to, Fab'$_2$, IgG, IgM, IgA, IgE, scFv, dAb, nanobodies, unibodies, and diabodies. In various embodiments preferred antibodies include, but are not limited to Fab'$_2$, IgG, IgM, IgA, IgE, and single chain antibodies, more preferably single chain Fv (scFv) antibodies in which a variable heavy and a variable light chain are joined together (directly or through a peptide linker) to form a continuous polypeptide.

In certain embodiments antibodies and fragments used in the constructs of the present invention can be bispecific. Bispecific antibodies or fragments can be of several configurations. For example, bispecific antibodies may resemble single antibodies (or antibody fragments) but have two different antigen binding sites (variable regions). In various embodiments bispecific antibodies can be produced by chemical techniques (Kranz et al. (1981) *Proc. Natl. Acad. Sci., USA*, 78: 5807), by "polydoma" techniques (see, e.g., U.S. Pat. No. 4,474,893), or by recombinant DNA techniques. In certain embodiments bispecific antibodies of the present invention can have binding specificities for at least two different epitopes at least one of which is a tumor associate antigen. In various embodiments the antibodies and fragments can also be heteroantibodies. Heteroantibodies are two or more antibodies, or antibody binding fragments (e.g., Fab) linked together, each antibody or fragment having a different specificity.

An "antigen-binding site" or "binding portion" refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. *Sequences of proteins of immunological interest*, 4th ed. U.S. Dept. Health and Human Services, Public Health Services, Bethesda, Md. (1987).

The terms "label" or "detectable label" are used herein to refer to any composition detectable by spectroscopic, photochemical, biochemical, immunochemical, electrical, optical or chemical means. Such labels include biotin for staining with labeled streptavidin conjugate, magnetic beads (e.g., DYNABEADS®), fluorescent dyes (e.g., fluorescein, texas red, rhodamine, green fluorescent protein, and the like), radiolabels (e.g., 3H, 125I, 35S, 14C, or 32P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

BRIEF DESCRIPTION OF THE DRAWINGS

FIG. 1A: BODIPY-LDL binding and uptake in HepG2 cells treated with DMSO or the synthetic LXR ligands GW3965 (GW) and T0901317 (T), (n=6). FIG. 1B: Immunoblot analysis of total HepG2 cell lysates. Cells were pretreated with DMSO or GW (1 μM) for 8 h and subsequently grown in LPDS, or in sterol depletion medium (LPDS supplemented with 5 μM simvastatin and 100 μM mevalonic acid) containing either DMSO or GW for an additional 18 h. The precursor (p) and mature (m) forms of the LDLR are indicated. FIG. 1C: Gene expression in HepG2 cells (n=5) following the indicated treatments was determined by realtime PCR. FIG. 1D: Immunoblot analysis of total SV589 cell lysates. Cells were pretreated with the LXR ligands GW or T (1 μM) for 8 h and subsequently cultured in sterol depletion medium for an additional 18 h. FIG. 1E: Immortalized MEFs from Lxrαβ(−/−) mice (DKO) and cells stably reconstituted with mLxra were pretreated with GW (1 μM) or 22R-hydroxycholesterol (2.5 μM) for 8 hrs and subsequently cultured in sterol depletion medium for an additional 18 h. FIG. 1F: Immunoblot analysis of total SV589 cell lysates. Cell were grown in 10% FBS and infected with adenovirus expressing GFP or Sult2b1 for 24 h and then cultured in sterol depletion medium for an additional 18 h. FIG. 1G: Immunofluorescence images of HepG2-LDLR-GFP cells treated with DMSO, GW and T (1 μM) for 72 hrs. *p<0.001. Error bars represent the mean±SD.

FIGS. 2A-2K show the LXR target gene Mylip is a regulator of LDLR protein expression. FIG. 2A: Induction of Mylip mRNA expression by GW or T (1 μM) in SV589 cells, HepG2 cells and in primary mouse astrocytes. FIG. 2B: LXR-dependent regulation of Mylip in MEFs and primary mouse hepatocytes following treatment with GW, T (both at 1 μM) or 22R-hydroxycholesterol (2.5 μM). FIG. 2C: Regulation of Mylip by LXR in vivo. Mice were gavaged with 20 mg/kg GW twice daily for three days and gene expression was analyzed by realtime PCR (n=6 mice/group). FIG. 2D: Dose-dependent reduction of LDLR-GFP protein in HEK293 cells co-transfected with Mylip and LDLR-GFP expression plasmids. Arrow indicates the Mylip protein. FIG. 2E: Immunofluorescence images of HEK293 cells co-transfected with LDLR-GFP and either wildtype or enzymatic mutant human and mouse Mylip. FIG. 2F: Immunoblot analysis of total 293 cell lysates co-transfected with Mylip constructs and the indicated GFP fusion proteins. Endogenous TFRC and MRLC are also shown. FIG. 2G: Primary hepatocytes were isolated and infected with Ad-GFP or Ad-Mylip for 24 h followed by culture in sterol depletion medium for an additional 18 h. FIG. 2H: BODIPY-LDL binding and uptake in DKO-mLxrα cells following infection with Ad-LacZ or Ad-Mylip (n=6); FIG. 2I: DKO-mLxrα cells were infected with control (shLamin) or two independent adenoviral Mylip shRNA constructs for 24 h and subsequently cultured for 18 h in sterol depletion medium. FIG. 2J: BODIPY-LDL binding and uptake in DKO-mLxrα cells following infection with Ad-shLAMIN, Ad-shMylip1, or Ad-shMylip2 (n=4). FIG. 2K: DKO-mLxrα cells were infected with the indicated adenovirus for 24 h. Subsequently, cells were pre-treated for 8 h with DMSO or GW (1 μM) followed by an additional 18 h in sterol depletion medium. A representative of 4 independent experiments is shown *p<0.05, p<0.01, *p<0.001.

FIGS. 3A-3G, show that Mylip reduces LDLR protein expression through ubiquitination of conserved residues in its cytoplasmic domain. FIG. 3A: 24 h following infection with Ad-LacZ or Ad-Mylip HepG2-LDLR-GFP cells were metabolically labelled with [$^{35}$S]Methionine and [$^{35}$S]Cysteine for 30 minutes. Samples were immunopreciptiated at the indicated time points following labeling. FIG. 3B: HEK293 cells were co-transfected with LDLR-GFP, Mylip and HA-Ubiquitin expression plasmids. Subsequently, samples were immunoblotted as indicated. FIG. 3C: Immunoblot analysis of total HEK293 cell lysates 48 h after co-transfection with Mylip and LDLR expression plasmids. FIG. 3D: Evolutionary conservation of the LDLR intracellular domain. Residues that serve as potential ubiquitination sites are indicated. *H. sapiens* (SEQ ID NO:1), *P. troglodytes* (SEQ ID NO:2), *R. norvegicus* (SEQ ID NO:3), *M. musculus* (SEQ ID NO:4), *O. cuniculus* (SEQ ID NO:5); FIGS. 3E and 3F: Immunoblot analysis of HEK293 total cell lysates co-transfected with control or Mylip expression plasmids along with the indicated mutated LDLR constructs. Numbering in the LDLR constructs refers to FIG. 1D. FIG. 3G: HEK293 cells were co-transfected with LDLR, Mylip and HA-Ubiquitin expression plasmids. Subsequently, cells were treated with vehicle or 25 μM MG132 for 6 h.

FIGS. 4A-4G show that expression of Mylip reduces LDLR expression and elevates plasma cholesterol and LDL levels in vivo. FIG. 4A: Analysis of plasma 6 days after transduction of C57BL/6 mice with Ad-LacZ or Ad-Mylip. FFA, free fatty acids (n=8 mice/group). FIGS. 4B and 4C: Cholesterol and triglyceride content of fractionated plasma from mice infected with Ad-LacZ or Ad-Mylip. FIG. 4D: Immunodetection of ApoB100, and ApoB48 in fractionated plasma of Ad-LacZ and Ad-Mylip infected mice. FIG. 4E: Gene expression in livers of Ad-LacZ and Ad-Mylip infected mice. FIG. 4F: Immunoblot analysis of total liver lysates. FIG. 4G: Cholesterol content of fractionated plasma from Ldlr(−/−) mice infected with Ad-LacZ, or Ad-Mylip. ***p<0.001.

FIGS. 6A-6E illustrate the identification of the Mylip gene as a direct target for LXR regulation. FIG. 6A: Mylip expression in RAW264.7 macrophage cells following treatment with the LXR ligand GW (1 μM), the RXR ligand LG268 (50 nM), and/or cycloheximide (CHX, 10 μg/mL). FIG. 6B: Mylip expression in thioglycolate-elicited peritoneal macrophages following 24 h treatment with DMSO, GW (1 μM), or 25-hydroxycholesterol (2.5 μM). FIG. 6C: Sequence of the LXRE in the mouse Mylip proximal promoter. Mylip WT DR4 sense strand (SEQ ID NO:6), Mylip WT DR4 antisense strand (SEQ ID NO:7), Mylip MUT DR4 sense strand (SEQ ID NO:8), Mylip MUT DR4 antisense strand (SEQ ID NO:9). FIG. 6D: HEK293 cells were transfected with LXR and RXR expression vectors along with the indicated promoter constructs and treated for 48 h with GW (1 μM) and LG268 (50 nM). FIG. 6E: EMSA analysis of LXR/RXR binding to radiolabeled Mylip LXRE.

FIG. 8A: Gene expression in DKO-Lxrα MEFs following transduction with the indicated adenoviral shRNA constructs determined by realtime PCR. FIG. 8B: Effect of Mylip knockdown on LDLR is comparable to sterol depletion. Immunoblot analysis of total DKO-Lxrα cell lysates. Where indicated cells were infected with Ad-shLAMIN or AdshMylip for 24 h. Subsequently, cells were culture in 10% LPDS, or sterol depletion medium for an additional 18 h.

FIG. 9A: The NPXY endocytosis motif is not required for Mylip inhibition of LDLR expression. Immunoblot analysis of total HEK293 cell lysates following co-transfection with plasmids encoding Mylip and/or LDLR- GFP or LDLR(Y18A)-GFP. Figure B: Mutation of I28 in the LDLR cytoplasmic domain does not inhibit Mylip action on the LDLR. Immunoblot analysis of total HEK293 cell lysates following co-transfection with plasmids encoding Mylip and LDLR various LDLR mutants as indicated.

FIGS. 10A-10E show that adenoviral expression of Mylip regulates plasma cholesterol levels in vivo. FIG. 10A: Analysis of plasma from Ad-LacZ and Ad-Mylip infected C57BL/6 mice. FFA, free fatty acids (n=8 mice/group). FIG. 10B: Cholesterol content of fractionated plasma from mice infected with Ad-LacZ, or Ad-Mylip. FIG. 10C: Gene expression in livers of AdLacZ, or Ad-Mylip infected mice determined by realtime PCR. FIG. 10D: Analysis of plasma from Ad-LacZ and Ad-Mylip infected C57BL/6 Ldlr(−/−) mice (n=5 mice/group). FIG. 10E: Triglyceride content of fractionated plasma from C57BL/6 Ldlr(−/−) mice) infected with Ad-LacZ, or Ad-Mylip (n=5 mice/group).

FIGS. 11A and 11B illustrate knockdown of Mylip expression by multiple shRNA sequences. Immunoblot analysis of total HEK293 cell lysates following co-transfection with pENTR-U6-shLacZ (control), or with four independent shRNA constructs targeting mouse Mylip and (FIG. 11A) non-tagged mutated mMylip (C387A), and (FIG. 11B) pEGFP-N3-wt mMylip.

FIG. 12A: Realtime PCR analysis of mRNA expression in WT and Idol−/− ES cells. FIG. 12B: Immunoblot analysis of LDLR protein expression in WT and Idol−/− ES cells treated with vehicle or LXR agonist.

DETAILED DESCRIPTION

Figure 1A:
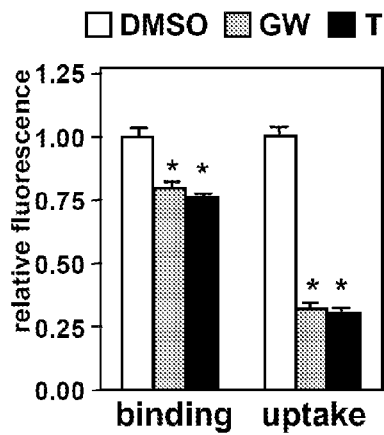
FIGS. 1A-1G show that activation of LXR inhibits LDL uptake through reduction in LDLR protein expression.

In various embodiments this invention pertains to a novel hepatic target for treatment of hypercholesterolemia. In particular, in certain embodiments, this invention pertains to the discovery that myosin light chain interacting protein (Mylip) (also known as Inducible Degrader of the LDLR or IDOL) is a regulator of cholesterol homeostasis. Mylip is a transcriptional target of the Liver X Receptors (LXR5) in different murine and human cells types and tissues including liver. Mylip is a highly conserved ERM-like protein that contains a C-terminal RING domain. Mylip is thought to function as an E3-ubiquitin ligase, but its protein targets and physiological roles are unknown.

Our research identified Mylip as an in vivo regulator of hepatic levels of the LDLR, independent of the cholesterol biosynthetic pathway that is targeted by statins. Adenoviral-mediated hepatic expression of Mylip results in severely diminished LDLR levels and increased total cholesterol and LDL levels. Similarly, Mylip reduces LDLR in vitro. Importantly, this activity depends on an intact RING (the E3-ubiquitin-ligase) domain suggesting that the ability of Mylip to reduce the LDLR depends on its enzymatic activity. Thus, genetic methods or chemicals that can inhibit the expression and/or activity of Mylip in the liver can form the basis for a new class of drugs for treating hypercholesterolemia and cardiac disease.

Accordingly, in certain embodiments, methods are provided for inhibiting LDL receptor degradation and/or promoting LDL uptake in a mammal, and/or one mitigating or more symptoms of hypercholesterolemia in a mammal. The methods typically involve administering to the mammal an agent that inhibits the expression and/or activity of Mylip. Methods are also provided of screening for such agents.

I. Assays for Inhibitors of Myosin Light Chain Interacting Protein (Mylip)

As indicated above, it was a surprising discovery that inhibition of Mylip expression or activity can inhibit LDL receptor degradation and/or promote LDL uptake in a mammal, and/or mitigate one or more symptoms of hypercholesterolemia. Mylip thus provides a target to screen for agents that inhibit LDL receptor degradation and/or promote LDL uptake in a mammal, and/or mitigate one or more symptoms of. In various embodiments the methods can involve contacting a cell, a tissue, an organism with one or more test agents and detecting (resulting changes in) the expression level and/or activity level of. Inhibition of Mylip expression tore of an aging process.

It is noted that when screening for Mylip inhibitors, a positive assay result need not indicate the particular test agent is a good pharmaceutical. Rather a positive result can simply indicate that the test agent can be used to inhibit Mylip activity and/or can also serve as a lead compound in the development of other modulators.

Using the methods described herein, test agents can readily be screened for the ability to inhibit Mylip expression and/or activity.

Activity-Based Assays.

For example, inhibition of Mylip expression and/or activity can readily be determined by placing one or more reporter genes under control of a promoter system whose regulation is controlled by Mylip or the Mylip promoter. Cell(s) containing such constructs are contacted with test agents, and a reduction in the reporter indicates that the test agent(s) inhibit Mylip expression or activity.

We have developed the following cell based assay systems/strategies for high throughput screening of Mylip/Idol inhibitors (see, e.g., Example 1). While specific examples of cell types, vectors, transfection strategies, tags are given, it will be recognized that these are illustrative and not limiting. Using the teachings provided herein, other cells, constructs, labels, and assay formats will be available to one of skill in the art.

The assays described below can also be employed in combination, with one serving as the primary screen and the others as secondary screens. In certain embodiments two of these assays could also be combined in the same reporter cell line (e.g. a single cell line that expresses both LDLR (1) and Mylip (2) reporters):

Cell Based Assay for Inhibitors of Mylip Action on the LDLR.

In certain embodiments cell based assays can be used to screen test agents (potential inhibitors) for inhibition of Mylip action on the LDL receptor (LDLR).

For example, a reporter cell line (e.g. HEK293, HepG2 cells) can be transfected (stably, transiently, virally etc.) with a tagged version of the LDLR, expression of which can be readily assayed by HTS methods. For example LDLR-luciferase fusion protein expression can be assayed by luciferase activity. Alternatively, LDLR-GFP fusion protein can be assayed by high content imaging. Other variations on this idea are possible.

A second component of the assay is to co-transfect (either stably or transiently or by adenoviral transduction) the reporter cells with active Mylip/Idol. In basal state, this results in very little or no signal from the LDLR-fusion protein because it is degraded by Mylip (see, e.g., FIG. 2E). HTS screening is used to identify small molecules, RNAs, genes etc that block Mylip action and thereby increase expression of LDLR-fusion reporter.

Cell Based Assay for Inhibitors of Mylip Auto-Degradation.

Another approach uses cell-based assays for inhibitors of Mylip auto-degradation. These assays take advantage of our discovery that Mylip E3 ligase activity leads to auto-degradation of Mylip protein. Thus, Mylip inhibitors can be identified by screening for compounds, genes, RNAs etc that stabilize Mylip protein expression (see FIGS. 2F and 2I). A reporter cell line (e.g. HEK293 cells, HepG2 cells) is transfected (stably or transiently, virally etc) with a tagged version of Mylip, expression of which can be readily assayed by HTS methods. For example, Mylip-luciferase fusion protein expression can be assayed by luciferase activity. Alternatively, Mylip-GFP fusion protein expression can be assayed by high content imaging. Other variations on this idea are possible. In the basal state, reporter cells express very little signal from the Mylip-luciferase (or other) fusion protein because Mylip catalyzes its own degradation and is very unstable. HTS screening is used to identify small molecules, RNAs, genes etc that block Mylip autodegradation thereby increase expression of Mylip-fusion reporter.

Cell Based Assay for Inhibitors of Mylip Action on LDL Uptake.

A reporter cell line (e.g. HEK293, HepG2 cells) expressing the LDLR (either endogenously or through transfection) can be cotransfected with Mylip expression vector. Uptake of labeled LDL (e.g., BODIPY-LDL) is determined (e.g., by high content imaging). In basal state, this results in very little or no labeled LDL uptake because the LDLR is degraded by Mylip. HTS screening is used to identify small molecules, RNAs, genes etc that block Mylip action and thereby increase BODIPY-LDL uptake (see, e.g., FIG. 2J).

Cell- and Animal-Based Inhibitor Assays.

In certain embodiments wildtype (WT) and Idol–/– cells or animals are screened for their response to candidate small molecule modulators (e.g., inhibitors) of Idol expression and/or activity. The effect of Idol-specific small molecules is lost or reduced in the Idol–/– cells, tissues, and/or animals. This screening method will be used, for example, in conjunction with the cell-based reporter screens described above.

Similarly animals, tissues, and/or cells overexpressing idol can be screened for the activity of candidate inhibitors using, for example, wildtype cells, and/or tissues, and/or animals as a control.

Nucleic-Acid Based Assays.

Using the known nucleic acid sequences for Mylip, copy number and/or, Mylip expression level, can be directly measured according to a number of different methods as described below. In particular, expression levels of a gene can be altered by changes in the copy number of the gene, and/or by changes in the transcription of the gene product (i.e. transcription of mRNA), and/or by changes in translation of the gene product (i.e. translation of the protein), and/or by post-translational modification(s) (e.g. protein folding, glycosylation, etc.). Thus useful assays of this invention include assaying for copy number, level of transcribed mRNA, level of translated protein, activity of translated protein, etc. Examples of such approaches are described below.

1) Target Molecules.

Changes in expression level can be detected by measuring changes in mRNA and/or a nucleic acid derived from the mRNA (e.g. reverse-transcribed cDNA, etc.). In order to measure the Mylip expression level it is desirable to provide a nucleic acid sample for such analysis. In certain preferred embodiments the nucleic acid is found in or derived from a biological sample. The term "biological sample", as used herein, refers to a sample obtained from an organism or from components (e.g., cells) of an organism, or from cells in culture. The sample may be of any biological tissue or fluid. Biological samples may also include organs or sections of tissues such as frozen sections taken for histological purposes.

The nucleic acid (e.g., mRNA nucleic acid derived from mRNA) is, in certain preferred embodiments, isolated from the sample according to any of a number of methods well known to those of skill in the art. Methods of isolating mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation*, Elsevier, N.Y. and Tijssen ed.

In a certain embodiments, the "total" nucleic acid is isolated from a given sample using, for example, an acid guanidinium-phenol-chloroform extraction method and polyA+ mRNA is isolated by oligo dT column chromatography or by using (dT)n magnetic beads (see, e.g., Sambrook et al., *Molecular Cloning: A Laboratory Manual* (2nd ed.), Vols. 1-3, Cold Spring Harbor Laboratory, (1989), or *Current Protocols in Molecular Biology*, F. Ausubel et al., ed. Greene Publishing and Wiley-Interscience, New York (1987)).

Frequently it is desirable to amplify the nucleic acid sample prior to assaying for expression level. Methods of amplifying nucleic acids are well known to those of skill in the art and include, but are not limited to polymerase chain reaction (PCR, see. e.g, Innis, et al., (1990) *PCR Protocols. A guide to Methods and Application. Academic Press, Inc. San Diego*,), ligase chain reaction (LCR) (see Wu and Wallace (1989) *Genomics* 4: 560, Landegren et al. (1988) *Science* 241: 1077, and Barringer et al. (1990) *Gene* 89: 117, transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.).

In one illustrative embodiment, where it is desired to quantify the transcription level (and thereby expression) of Mylip in a sample, the nucleic acid sample is one in which the concentration of the Mylip mRNA transcript(s), or the concentration of the nucleic acids derived from the Mylip mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5 fold difference in concentration of the target mRNA results in a 3 to 6 fold difference in hybridization intensity is sufficient for most purposes.

Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In one simple mbodiment, the Mylip-containing nucleic acid sample is the total mRNA or a total cDNA isolated and/or otherwise derived from a biological sample. The nucleic acid may be isolated from the sample according to any of a number of methods well known to those of skill in the art as indicated above.

2) Hybridization-Based Assays.

Using known Mylip sequences detecting and/or quantifying the Mylip transcript(s) can be routinely accomplished using nucleic acid hybridization techniques (see, e.g., Sambrook et al. supra). For example, one method for evaluating the presence, absence, or quantity of Mylip reverse-transcribed cDNA involves a "Southern Blot". In a Southern Blot, the DNA (e.g., reverse-transcribed Mylip mRNA), typically fragmented and separated on an electrophoretic gel, is hybridized to a probe specific for Mylip (or to a mutant thereof). Comparison of the intensity of the hybridization signal from the Mylip probe with a "control" probe (e.g. a probe for a "housekeeping gene) provides an estimate of the relative expression level of the target nucleic acid.

Alternatively, the Mylip mRNA can be directly quantified in a Northern blot. In brief, the mRNA is isolated from a given cell sample using, for example, an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify and/or quantify the target Mylip mRNA. Appropriate controls (e.g. probes to housekeeping genes) provide a reference for evaluating relative expression level.

An alternative means for determining the Mylip expression level is in situ hybridization. In situ hybridization assays are well known (e.g., Angerer (1987) Meth. Enzymol 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application.

In some applications it is necessary to block the hybridization capacity of repetitive sequences. Thus, in some embodiments, tRNA, human genomic DNA, or Cot-1 DNA is used to block non-specific hybridization.

3) Amplification-Based Assays.

In another embodiment, amplification-based assays can be used to measure Mylip expression (transcription) level. In such amplification-based assays, the target nucleic acid sequences (i.e., Mylip) act as template(s) in amplification reaction(s) (e.g. Polymerase Chain Reaction (PCR) or reverse-transcription PCR, or quantitative PCR (e.g., quantitative RT-PCR). In a quantitative amplification, the amount of amplification product will be proportional to the amount of template (e.g., Mylip mRNA) in the original sample. Comparison to appropriate (e.g. healthy tissue or cells unexposed to the test agent) controls provides a measure of the Mylip transcript level.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis et al. (1990) *PCR Protocols, A Guide to Methods and Applications*, Academic Press, Inc. N.Y.). One approach, for example, involves simultaneously co-amplifying a known quantity of a control sequence using the same primers as those used to amplify the target. This provides an internal standard that may be used to calibrate the PCR reaction.

One typical internal standard is a synthetic AW106 cRNA. The AW106 cRNA is combined with RNA isolated from the sample according to standard techniques known to those of skill in the art. The RNA is then reverse transcribed using a reverse transcriptase to provide copy DNA. The cDNA sequences are then amplified (e.g., by PCR) using labeled primers. The amplification products are separated, typically by electrophoresis, and the amount of labeled nucleic acid (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al. (1990) Academic Press, Inc. N.Y. The known nucleic acid sequence(s) for MYLIP are sufficient to enable one of skill to routinely select primers to amplify any portion of the gene.

4) Hybridization Formats and Optimization of Hybridization Conditions.

a) Array-Based Hybridization Formats.

In one embodiment, the methods of this invention can be utilized in array-based hybridization formats. Arrays are a multiplicity of different "probe" or "target" nucleic acids (or other compounds) attached to one or more surfaces (e.g., solid, membrane, or gel). In a certain embodiments, the multiplicity of nucleic acids (or other moieties) is attached to a single contiguous surface or to a multiplicity of surfaces juxtaposed to each other.

In an array format a large number of different hybridization reactions can be run essentially "in parallel." This provides rapid, essentially simultaneous, evaluation of a number of hybridizations in a single "experiment". Methods of performing hybridization reactions in array based formats are well known to those of skill in the art (see, e.g., Pastinen (1997) *Genome Res.* 7: 606-614; Jackson (1996) *Nature Biotechnol-* ogy 14:1685; Chee (1995) *Science* 274: 610; WO 96/17958, Pinkel et al. (1998) *Nature Genetics* 20: 207-211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted arrays (see, e.g., U.S. Pat. No. 5,807,522). This patent describes the use of an automated system that taps a microcapillary against a surface to deposit a small volume of a biological sample. The process is repeated to generate high-density arrays.

Arrays can also be produced using oligonucleotide synthesis technology. Thus, for example, U.S. Pat. No. 5,143,854 and PCT Patent Publication Nos. WO 90/15070 and 92/10092 teach the use of light-directed combinatorial synthesis of high density oligonucleotide arrays. Synthesis of high-density arrays is also described in U.S. Pat. Nos. 5,744,305, 5,800,992 and 5,445,934.

b) Other Hybridization Formats.

As indicated above a variety of nucleic acid hybridization formats are known to those skilled in the art. For example, common formats include sandwich assays and competition or displacement assays. Such assay formats are generally described in Hames and Higgins (1985) *Nucleic Acid Hybridization, A Practical Approach*, IRL Press; Gall and Pardue (1969) *Proc. Natl. Acad. Sci. USA* 63: 378-383; and John et al. (1969) *Nature* 223: 582-587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample will provide the target nucleic acid. The "capture" nucleic acid and "signal" nucleic acid probe hybridize with the target nucleic acid to form a "sandwich" hybridization complex. To be most effective, the signal nucleic acid should not hybridize with the capture nucleic acid.

Typically labeled signal nucleic acids are used to detect hybridization.

Complementary nucleic acids or signal nucleic acids may be labeled by any one of several methods typically used to detect the presence of hybridized polynucleotides. The most common method of detection is the use of autoradiography with 3H, $^{125}$I, $^{35}$S, $^{14}$C, or $^{32}$P-labelled probes or the like. Other labels include ligands that bind to labeled antibodies, fluorophores, chemi-luminescent agents, enzymes, and antibodies that can serve as specific binding pair members for a labeled ligand.

Detection of a hybridization complex may require the binding of a signal generating complex to a duplex of target and probe polynucleotides or nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

c) Optimization of Hybridization Conditions.

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In a preferred embodiment, hybridization is performed at low stringency to ensure hybridization and then subsequent washes are performed at higher stringency to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be present.

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array may be washed at successively higher stringency solutions and read between each wash. Analysis of the data sets thus produced will reveal a wash stringency above which the hybridization pattern is not appreciably altered and which provides adequate signal for the particular probes of interest.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.).

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes*, Elsevier, N.Y.).

Optimal conditions are also a function of the sensitivity of label (e.g., fluorescence) detection for different combinations of substrate type, fluorochrome, excitation and emission bands, spot size and the like. Low fluorescence background surfaces can be used (see, e.g., Chu (1992) *Electrophoresis* 13:105-114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

d) Labeling and Detection of Nucleic Acids.

The probes used herein for detection of Mylip expression levels can be full length or less than the full length of the Mylip or mutants thereof. Shorter probes are empirically tested for specificity. Preferred probes are sufficiently long so as to specifically hybridize with the Mylip target nucleic acid(s) under stringent conditions. The preferred size range is from about 10, 15, or 20 bases to the length of the Mylip mRNA, more preferably from about 30 bases to the length of the Mylip mRNA, and most preferably from about 40 bases to the length of the Mylip mRNA. The probes are typically labeled, with a detectable label as described above.

Polypeptide-Based Assays.

The effect of a test agent on MYLIP expression can also be determined by determining the effect of that test agent on translated Mylip protein.

The polypeptide(s) encoded by the Mylip gene can be detected and quantified by any of a number of methods well known to those of skill in the art. These may include analytic biochemical methods such as electrophoresis, capillary electrophoresis, high performance liquid chromatography (HPLC), thin layer chromatography (TLC), hyperdiffusion chromatography, mass spectroscopy, and the like, or various immunological methods such as fluid or gel precipitin reactions, immunodiffusion (single or double), immunoelectrophoresis, radioimmunoas say (RIA), enzyme-linked immunosorbent assays (ELISAs), immunofluorescent assays, western blotting, and the like.

In one preferred embodiment, the Mylip polypeptide(s) are detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol.* 182: *Guide to Protein Purification*, Academic Press, Inc., N.Y.).

In another preferred embodiment, Western blot (immunoblot) analysis is used to detect and quantify the presence of polypeptide(s) of this invention in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target polypeptide(s).

The antibodies specifically bind to the target polypeptide(s) and may be directly labeled or alternatively may be subsequently detected using labeled antibodies (e.g., labeled sheep anti-mouse antibodies) that specifically bind to a domain of the antibody.

In preferred embodiments, the Mylip polypeptide(s) are detected using an immunoassay. As used herein, an immunoassay is an assay that utilizes an antibody to specifically bind to the analyte (e.g., the target polypeptide(s)). The immunoassay is thus characterized by detection of specific binding of a polypeptide of this invention to an antibody as opposed to the use of other physical or chemical properties to isolate, target, and quantify the analyte.

Any of a number of well recognized immunological binding assays (see, e.g., U.S. Pat. Nos. 4,366,241; 4,376,110; 4,517,288; and 4,837,168) are well suited to detection or quantification of the polypeptide(s) identified herein. For a review of the general immunoassays, see also Asai (1993) *Methods in Cell Biology Volume* 37: *Antibodies in Cell Biology*, Academic Press, Inc. New York; Stites & Ten (1991) *Basic and Clinical Immunology* 7th Edition.

Immunological binding assays (or immunoassays) typically utilize a "capture agent" to specifically bind to and often immobilize the analyte (Mylip polypeptide). In preferred embodiments, the capture agent is an antibody.

Immunoassays also often utilize a labeling agent to specifically bind to and label the binding complex formed by the capture agent and the analyte. The labeling agent may itself be one of the moieties comprising the antibody/analyte complex. Thus, the labeling agent may be a labeled polypeptide or a labeled antibody that specifically recognizes the already bound target polypeptide. Alternatively, the labeling agent may be a third moiety, such as another antibody, that specifically binds to the capture agent/polypeptide complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401-1406, and Akerstrom (1985) *J. Immunol.*, 135: 2589-2542).

Typical immunoassays for detecting the target polypeptide(s) are either competitive or noncompetitive. Noncompetitive immunoassays are assays in which the amount of captured analyte is directly measured. In one "sandwich" assay, for example, the capture agents (antibodies) can be bound directly to a solid substrate where they are immobilized. These immobilized antibodies then capture the target polypeptide present in the test sample. The target polypeptide thus immobilized is then bound by a labeling agent, such as a second antibody bearing a label.

In competitive assays, the amount of analyte (MYLIP polypeptide) present in the sample is measured indirectly by measuring the amount of an added (exogenous) analyte displaced (or competed away) from a capture agent (antibody) by the analyte present in the sample. In one competitive assay, a known amount of, in this case, labeled polypeptide is added to the sample and the sample is then contacted with a capture agent. The amount of labeled polypeptide bound to the antibody is inversely proportional to the concentration of target polypeptide present in the sample.

In one embodiment, the antibody is immobilized on a solid substrate. The amount of target polypeptide bound to the antibody may be determined either by measuring the amount of target polypeptide present in an polypeptide/antibody complex, or alternatively by measuring the amount of remaining uncomplexed polypeptide.

The immunoassay methods of the present invention include an enzyme immunoassay (EIA) which utilizes, depending on the particular protocol employed, unlabeled or labeled (e.g., enzyme-labeled) derivatives of polyclonal or monoclonal antibodies or antibody fragments or single-chain antibodies that bind Mylip polypeptide(s), either alone or in combination. In the case where the antibody that binds Mylip polypeptide is not labeled, a different detectable marker, for example, an enzyme-labeled antibody capable of binding to the monoclonal antibody which binds the Mylip polypeptide, may be employed. Any of the known modifications of EIA, for example, enzyme-linked immunoabsorbent assay (ELISA), may also be employed. As indicated above, also contemplated by the present invention are immunoblotting immunoassay techniques such as western blotting employing an enzymatic detection system.

The immunoassay methods of the present invention may also be other known immunoassay methods, for example, fluorescent immunoassays using antibody conjugates or antigen conjugates of fluorescent substances such as fluorescein or rhodamine, latex agglutination with antibody-coated or antigen-coated latex particles, haemagglutination with antibody-coated or antigen-coated red blood corpuscles, and immunoassays employing an avidin-biotin or strepavidin-biotin detection systems, and the like.

The particular parameters employed in the immunoassays of the present invention can vary widely depending on various factors such as the concentration of antigen in the sample, the nature of the sample, the type of immunoassay employed and the like. Optimal conditions can be readily established by those of ordinary skill in the art. In certain embodiments, the amount of antibody that binds Mylip polypeptides is typically selected to give 50% binding of detectable marker in the absence of sample. If purified antibody is used as the antibody source, the amount of antibody used per assay will generally range from about 1 ng to about 100 ng. Typical assay conditions include a temperature range of about 4° C. to about 45° C., preferably about 25° C. to about 37° C., and most preferably about 25° C., a pH value range of about 5 to 9, preferably about 7, and an ionic strength varying from that of distilled water to that of about 0.2M sodium chloride, preferably about that of 0.15M sodium chloride. Times will vary widely depending upon the nature of the assay, and generally range from about 0.1 minute to about 24 hours. A wide variety of buffers, for example PBS, may be employed, and other reagents such as salt to enhance ionic strength, proteins such as serum albumins, stabilizers, biocides and non-ionic detergents may also be included.

The assays of this invention are scored (as positive or negative or quantity of target polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target polypeptide concentration.

Antibodies for use in the various immunoassays described herein can be routinely produced or obtained commercially.

Idol/LDLR Interaction Assays.

As shown in Example 2, the residues conserved between LDLR, VLDLR and apoER2 are important for Idol recognition. It was further determined that the FERM domain of Idol is important for interaction with the LDLR. Disruption of Idol FERM domain interaction with these LDLR residues using a small molecule would inactivate the Idol-LDLR pathway.

The Idol-LDLR recognition sequence can be used as the basis for screens aimed at identifying small molecules that specifically disrupted Idol-LDLR interaction e.g., by targeting this region of the LDLR.

Accordingly, in certain embodiments, screening systems are contemplated that screen for the ability of test agents to bind the FERM domain of LDLR and/or to bind/interact with the region of LDLR that interacts with Idol and/or that inhibit the interaction of Idol and LDLR.

In view of the teachings provided herein, methods of screening for agents that bind the FERM domain of Idol or that bind to the LDLR region that interacts with Idol are readily available to those of skill in the art. For example, in certain illustrative embodiments, Idol FERM domain and/or LDLR domains are immobilized and probed with test agents. Detection of the test agent (e.g., via a label attached to the test agent) indicates that the agent binds to the target moiety and is a good candidate modulator of Idol/LDLR interaction.

In another illustrative embodiment, the association of LDLR and Idol or a FERM domain of Idol in the presence of one or more test agents is assayed. This can be accomplished using for example a fluorescence resonance energy transfer system (FRET) comprising a donor fluorophore on one moiety (e.g., LDLR) and an acceptor fluorophore on the Idol molecule. The donor and acceptor quench each other when brought into proximity by the interaction of LDLR and Idol. When association is reduced or prevented by a test agent the FRET signal increases indicating that the test agent inhibits interaction of LDLR and Idol.

These assays are illustrative and not limiting. Using the teaching provided herein, numerous binding and/or LDLR/Idol interaction assays will be available to one of skill in the art.

Animal-Based Assays.

In certain embodiments cells, tissues, and/or animals are provided that are transfected with an Idol-encoding construct so they overexpress Idol. In other embodiments, cells, tissues, and/or animals in which Idol is "knocked out" are provided. It is completed that one or both of these constructs can be used in screens for Mylip (Idol) modulators.

For example, in certain embodiments, test agent(s) (e.g., small molecules) are screened for their erect on the Idol pathway based on the Idol-/- cells, tissues or animals. WT and Idol-/- are screened for response to candidate small molecules. The effect of Idol-specific small molecules will be lost in the Idol-/- cells. These screening methods can be used, for example, in conjunction with the cell-based reporter screens described herein.

In certain embodiments, knockout Mylip (Idol) animals are used in screens for modulators.

Assay Optimization.

The assays of this invention have immediate utility in screening for agents that inhibit Mylip expression and/or activity in a cell, tissue or organism. The assays of this invention can be optimized for use in particular contexts, depending, for example, on the source and/or nature of the biological sample and/or the particular test agents, and/or the analytic facilities available. Thus, for example, optimization can involve determining optimal conditions for binding assays, optimum sample processing conditions (e.g. preferred PCR conditions), hybridization conditions that maximize signal to noise, protocols that improve throughput, etc. In addition, assay formats can be selected and/or optimized according to the availability of equipment and/or reagents. Thus, for example, where commercial antibodies or ELISA kits are available it may be desired to assay protein concentration. Conversely, where it is desired to screen for modulators that alter transcription of Mylip gene, nucleic acid based assays are preferred.

Routine selection and optimization of assay formats is well known to those of ordinary skill in the art.

Pre-Screening for Agents that Bind Mylip.

In certain embodiments it is desired to pre-screen test agents for the ability to interact with (e.g. specifically bind to) a Mylip (or mutant/allele) nucleic acid or polypeptide. Specifically, binding test agents are more likely to interact with and thereby modulate Mylip expression and/or activity. Thus, in some embodiments, the test agent(s) are pre-screened for binding to Mylip nucleic acids or to Mylip proteins before performing the more complex assays described above.

In one embodiment, such pre-screening is accomplished with simple binding assays. Means of assaying for specific binding or the binding affinity of a particular ligand for a nucleic acid or for a protein are well known to those of skill in the art. In certain illustrative binding assays, the Mylip protein (e.g., Idol FERM domain or full-length Idol) or nucleic acid encoding such is immobilized and exposed to a test agent (which can be labeled), or alternatively, the test agent(s) are immobilized and exposed to an Mylip protein or to a Mylip nucleic acid (which can be labeled). The immobilized moiety is then washed to remove any unbound material and the bound test agent or bound Mylip nucleic acid or protein is detected (e.g. by detection of a label attached to the bound molecule). The amount of immobilized label is proportional to the degree of binding between the Mylip protein or nucleic acid and the test agent.

Scoring the Assay(s).

The assays of this invention are scored according to standard methods well known to those of skill in the art. The assays of this invention are typically scored as positive where there is a difference between the activity seen with the test agent present or where the test agent has been previously applied, and the (usually negative) control. In preferred embodiments, the change is a statistically significant change, e.g. as determined using any statistical test suited for the data set provided (e.g. t-test, analysis of variance (ANOVA), semi-parametric techniques, non-parametric techniques (e.g. Wilcoxon Mann-Whitney Test, Wilcoxon Signed Ranks Test, Sign Test, Kruskal-Wallis Test, etc.). Preferably the statistically significant change is significant at least at the 85%, more preferably at least at the 90%, still more preferably at least at the 95%, and most preferably at least at the 98% or 99% confidence level). In certain embodiments, the change is at least a 10% change, preferably at least a 20% change, more preferably at least a 50% change and most preferably at least a 90% change.

Agents for Screening: Combinatorial Libraries (e.g., Small Organic Molecules)

Virtually any agent can be screened according to the methods of this invention. Such agents include, but are not limited to nucleic acids, proteins, sugars, polysaccharides, glycoproteins, lipids, and small organic molecules. The term small organic molecule typically refers to molecules of a size comparable to those organic molecules generally used in pharmaceuticals. The term excludes biological macromolecules (e.g., proteins, nucleic acids, etc.). Preferred small organic molecules can range in size up to about 5000 Da, more preferably up to 2000 Da, and most preferably up to about 1000 Da.

Conventionally, new chemical entities with useful properties are generated by identifying a chemical compound (called a "lead compound") with some desirable property or activity, creating variants of the lead compound, and evaluating the property and activity of those variant compounds. However, the current trend is to shorten the time scale for all aspects of drug discovery. Because of the ability to test large numbers quickly and efficiently, high throughput screening (HTS) methods are replacing conventional lead compound identification methods.

In one preferred embodiment, high throughput screening methods involve providing a library containing a large number of potential therapeutic compounds (candidate compounds). Such "combinatorial chemical libraries" are then screened in one or more assays, as described herein to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis by combining a number of chemical "building blocks" such as reagents. For example, a linear combinatorial chemical library such as a polypeptide (e.g., mutein) library is formed by combining a set of chemical building blocks called amino acids in every possible way for a given compound length (i.e., the number of amino acids in a polypeptide compound). Millions of chemical compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al. (1994) 37(9): 1233-1250).

Preparation of combinatorial chemical libraries is well known to those of skill in the art. Such combinatorial chemical libraries include, but are not limited to, peptide libraries (see, e.g., U.S. Pat. No. 5,010,175, Furka (1991) Int. J. Pept. Prot. Res., 37: 487-493, Houghton et al. (1991) Nature, 354: 84-88). Peptide synthesis is by no means the only approach envisioned and intended for use with the present invention. Other chemistries for generating chemical diversity libraries can also be used. Such chemistries include, but are not limited to: peptoids (PCT Publication No WO 91/19735, 26 Dec. 1991), encoded peptides (PCT Publication WO 93/20242, 14 Oct. 1993), random bio-oligomers (PCT Publication WO 92/00091, 9 Jan. 1992), benzodiazepines (U.S. Pat. No. 5,288,514), diversomers such as hydantoins, benzodiazepines and dipeptides (Hobbs et al., (1993) Proc. Nat. Acad. Sci. USA 90: 6909-6913), vinylogous polypeptides (Hagihara et al. (1992) J. Amer. Chem. Soc. 114: 6568), nonpeptidal peptidomimetics with a Beta-D-Glucose scaffolding (Hirschmann et al., (1992) J. Amer. Chem. Soc. 114: 9217-9218), analogous organic syntheses of small compound libraries (Chen et al. (1994) J. Amer. Chem. Soc. 116: 2661), oligocarbamates (Cho, et al., (1993) Science 261:1303), and/or peptidyl phosphonates (Campbell et al., (1994) J. Org. Chem. 59: 658). See, generally, Gordon et al., (1994) J. Med. Chem. 37:1385, nucleic acid libraries (see, e.g., Strategene, Corp.), peptide nucleic acid libraries (see, e.g., U.S. Pat. No. 5,539, 083) antibody libraries (see, e.g., Vaughn et al. (1996) Nature Biotechnology, 14(3): 309-314), and PCT/US96/10287), carbohydrate libraries (see, e.g., Liang et al. (1996) Science, 274: 1520-1522, and U.S. Pat. No. 5,593,853), and small organic molecule libraries (see, e.g., benzodiazepines, Baum (1993) C&EN, Jan 18, page 33, isoprenoids U.S. Pat. No. 5,569,588, thiazolidinones and metathiazanones U.S. Pat. No. 5,549, 974, pyrrolidines U.S. Pat. Nos. 5,525,735 and 5,519,134, morpholino compounds U.S. Pat. No. 5,506,337, benzodiazepines U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

A number of well known robotic systems have also been developed for solution phase chemistries. These systems include, but are not limited to, automated workstations like the automated synthesis apparatus developed by Takeda Chemical Industries, LTD. (Osaka, Japan) and many robotic systems utilizing robotic arms (Zymate II, Zymark Corporation, Hopkinton, Mass.; Orca, Hewlett-Packard, Palo Alto, Calif.) which mimic the manual synthetic operations performed by a chemist and the Venture™ platform, an ultra-high-throughput synthesizer that can run between 576 and 9,600 simultaneous reactions from start to finish (see Advanced ChemTech, Inc. Louisville, Ky.)). Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

High Throughput Screening

Any of the assays described herein are amenable to high-throughput screening (HTS). Moreover, the cells utilized in the methods of this invention need not be contacted with a single test agent at a time. To the contrary, to facilitate high-throughput screening, a single cell may be contacted by at least two, preferably by at least 5, more preferably by at least 10, and most preferably by at least 20 test compounds. If the cell scores positive, it can be subsequently tested with a subset of the test agents until the agents having the activity are identified.

High throughput assays for hybridizaiton assays, immunoassays, and for various reporter gene products are well known to those of skill in the art. For example, multi-well fluorimeters are commercially available (e.g., from Perkin-Elmer).

In addition, high throughput screening systems are commercially available (see, e.g., Zymark Corp., Hopkinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems provide detailed protocols the various high throughput. Thus, for example, Zymark Corp. provides technical bulletins describing screening systems for detecting the modulation of gene transcription, ligand binding, and the like.

Modulator Databases.

In certain embodiments, the agents that score positively in the assays described herein (e.g. show an ability to inhibit Mylip expression and/or activity) can be entered into a database of putative and/or actual Mylip inhibitors and/or aging inhibitors. The term database refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intranet, data or databases stored in specialized hardware (e.g. in microchips), and the like.

II. Inhibition of Mylip.

It was a surprising discovery that inhibition of Mylip expression or activity can inhibit LDL receptor degradation and/or promote LDL uptake in a mammal, and/or mitigate one or more symptoms of hypercholesterolemia. Any of a variety of methods to inhibit Mylip can be used.

RNAi Inhibition of Mylip/Idol.

Post-transcriptional gene silencing (PTGS) or RNA interference (RNAi) refers to a mechanism by which double-stranded (sense strand) RNA (dsRNA) specifically blocks expression of its homologous gene when injected, or otherwise introduced into cells. The discovery of this incidence came with the observation that injection of antisense or sense RNA strands into *Caenorhabditis elegans* cells resulted in gene-specific inactivation (Guo and Kempheus (1995) *Cell* 81: 611-620). While gene inactivation by the antisense strand was expected, gene silencing by the sense strand came as a surprise. Adding to the surprise was the finding that this gene-specific inactivation actually came from trace amounts of contaminating dsRNA (Fire et al. (1998) *Nature* 391: 806-811).

Since then, this mode of post-transcriptional gene silencing has been tied to a wide variety of organisms: plants, flies, trypanosomes, planaria, hydra, zebrafish, and mice (Zamore et al. (2000). *Cell* 101: 25-33; Gura (2000) *Nature* 404: 804-808). RNAi activity has been associated with functions as disparate as transposon-silencing, anti-viral defense mechanisms, and gene regulation (Grant (1999) *Cell* 96: 303-306).

By injecting dsRNA into tissues, one can inactivate specific genes not only in those tissues, but also during various stages of development. This is in contrast to tissue-specific knockouts or tissue-specific dominant-negative gene expressions, which do not allow for gene silencing during various stages of the developmental process (see, e.g., Gura (2000) *Nature* 404: 804-808). The double-stranded RNA is cut by a nuclease activity into 21-23 nucleotide fragments. These fragments, in turn, target the homologous region of their corresponding mRNA, hybridize, and result in a double-stranded substrate for a nuclease that degrades it into fragments of the same size (Hammond et al. (2000) *Nature*, 404: 293-298; Zamore et al. (2000). *Cell* 101: 25-33).

It has been shown that when short (18-30 bp) RNA duplexes are introduced into mammalian cells in culture, sequence-specific inhibition of target mRNA can be realized without inducing an interferon response. Certain of these short dsRNAs, referred to as small inhibitory RNAs ("siRNAs"), can act catalytically at sub-molar concentrations to cleave greater than 95% of the target mRNA in the cell. A description of the mechanisms for siRNA activity, as well as some of its applications are described in Provost et al. (2002) *EMBO J.*, 21(21): 5864-5874; Tabara et al. (2002) *Cell* 109 (7):861-71; Martinez et al. (2002) *Cell* 110(5): 563; Hutvagner and Zamore (2002), *Science* 297: 2056, and the like.

Using the known nucleotide sequence for the Mylip/Idol gene and/or mRNA, Mylip/Idol siRNAs can readily be produced. In various embodiments siRNA that inhibit Mylip/Idol can comprise partially purified RNA, substantially pure RNA, synthetic RNA, recombinantly produced RNA, as well as altered RNA that differs from naturally-occurring RNA by the addition, deletion, substitution and/or alteration of one or more nucleotides.

Such alterations can include, for example, addition of non-nucleotide material, such as to the end(s) of the siRNA or to one or more internal nucleotides of the siRNA, including modifications that make the siRNA resistant to nuclease digestion.

In various embodiments one or both strands of the siRNA can comprise a 3' overhang. As used herein, a "3' overhang" refers to at least one unpaired nucleotide extending from the 3'-end of an RNA strand. Thus in one embodiment, the siRNA comprises at least one 3' overhang of from 1 to about 6 nucleotides (which includes ribonucleotides or deoxynucleotides) in length, from 1 to about 5 nucleotides in length, from 1 to about 4 nucleotides in length, or about 2 to about 4 nucleotides in length.

In an illustrative embodiment in which both strands of the siRNA molecule comprise a 3' overhang, the length of the overhangs can be the same or different for each strand. In certain embodiments the 3' overhang is present on both strands of the siRNA, and is one, two, or three nucleotides in length. For example, each strand of the siRNA can comprise 3' overhangs of dithymidylic acid ("TT") or diuridylic acid ("uu").

In order to enhance the stability of the siRNA, the 3' overhangs can be also stabilized against degradation. In one embodiment, the overhangs are stabilized by including purine nucleotides, such as adenosine or guanosine nucleotides. In certain embodiments substitution of pyrimidine nucleotides by modified analogues, e.g., substitution of uridine nucleotides in the 3' overhangs with 2'-deoxythymidine, is tolerated and does not affect the efficiency of RNAi degradation. In particular, it is believed the absence of a 2' hydroxyl in the 2'-deoxythymidine can significantly enhance the nuclease resistance of the 3' overhang In certain embodiments, the siRNA comprises the sequence AA(N19)TT (SEQ ID NO:16), AA(N21)TT (SEQ ID NO:17), NA(N21) (SEQ ID NO:18), and the like, where N is any nucleotide. In various embodiments these siRNA comprise approximately 30%-70% GC, and preferably comprise approximately 50% G/C. The sequence of the sense siRNA strand corresponds to (N19)TT or N21 (i.e., positions 3 to 23), respectively. In the latter case, the 3' end of the sense siRNA is converted to TT. The rationale for this sequence conversion is to generate a symmetric duplex with respect to the sequence composition of the sense and antisense strand 3' overhangs. The antisense RNA strand is then synthesized as the complement to positions 1 to 21 of the sense strand.

Because position 1 of the 23-nt sense strand in these embodiments is not recognized in a sequence-specific manner by the antisense strand, the 3'-most nucleotide residue of the antisense strand can be chosen deliberately. However, the penultimate nucleotide of the antisense strand (complementary to position 2 of the 23-nt sense strand in either embodiment) is generally complementary to the targeted sequence.

In another illustrative embodiment, the siRNA comprises the sequence NAR(N17)YNN (SEQ ID NO:19), where R is a purine (e.g., A or G) and Y is a pyrimidine (e.g., C or U/T). The respective 21-nt sense and antisense RNA strands of this embodiment therefore generally begin with a purine nucleotide. Such siRNA can be expressed from pol III expression vectors without a change in targeting site, as expression of RNAs from pol III promoters is only believed to be efficient when the first transcribed nucleotide is a purine.

In various embodiments the siRNA of the invention can be targeted to any stretch of approximately 10-30, or 15-25, or 19-25 contiguous nucleotides in any of the target mRNA sequences (the "target sequence"). Techniques for selecting target sequences for siRNA are given, for example, in Tuschl et al., "The siRNA User Guide," revised May 6, 2004. The "siRNA User Guide" is available on the world wide web at a website maintained by Dr. Thomas Tuschl, and can be found by accessing the website of Rockefeller University and searching with the keyword "siRNA." In addition, the "siRNA User Guide" can be located by performing a google search for "siRNA User Guide" and can also be found at "www.rockefeller.edu/labheads/tuschl/sirna.html. Techniques for selecting target sequences for siRNA and miRNA can also be found in Sioud (2008) *siRNA and miRNA Gene Silencing: From Bench to Bedside (Methods in Molecular Biology)*, Humana Press.

In certain embodiments the sense strand of the present siRNA comprises a nucleotide sequence identical to any contiguous stretch of about 19 to about 25 nucleotides in the target Mylip/Idol mRNA. Generally, a target sequence on the target mRNA can be selected from a given cDNA sequence corresponding to the target mRNA, preferably beginning 50 to 100 nucleotides downstream (i.e., in the 3' direction) from the start codon. The target sequence can, however, be located in the 5' or 3' untranslated regions, or in the region nearby the start.

The Mylip/Idol silencing siRNAs can be obtained using a number of techniques known to those of skill in the art. For example, the siRNA can be chemically synthesized or recombinantly produced using methods known in the art, such as the *Drosophila* in vitor system described in U.S. published application US 2002/0086356.

In certain embodiments the siRNAs are chemically synthesized using appropriately protected ribonucleoside phosphoramidites and a conventional DNA/RNA synthesizer. The siRNAs can be synthesized as two separate, complementary RNA molecules, or as a single RNA molecule with two complementary regions. Commercial suppliers of synthetic RNA molecules or synthesis reagents include Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Custom siRNA can be obtained from commercial suppliers (see, e.g., Thermo Fisher Scientific, Lafayette Colo.; Qiagen, Valencia, Calif.; Applied Biosystems, Foster City, Calif.; and the like).

In certain embodiments siRNA can also be expressed from recombinant circular or linear DNA plasmids using any suitable promoter. Suitable promoters for expressing siRNA from a plasmid include, for example, the U6 or H1 RNA pol III promoter sequences and the cytomegalovirus promoter. Selection of other suitable promoters is within the skill in the art. The recombinant plasmids can also comprise inducible or regulatable promoters for expression of the siRNA in a particular tissue or in a particular intracellular environment.

The siRNA expressed from recombinant plasmids can either be isolated from cultured cell expression systems by standard techniques, or can be expressed intracellularly at or near the target area(s) in vivo. The use of recombinant plasmids to deliver siRNA to cells in vivo is discussed in more detail below.

siRNA can be expressed from a recombinant plasmid either as two separate, complementary RNA molecules, or as a single RNA molecule with two complementary regions. Selection of plasmids suitable for expressing siRNAs, methods for inserting nucleic acid sequences for expressing the siRNA into the plasmid, and methods of delivering the recombinant plasmid to the cells of interest are within the skill in the art (see, e.g., Tuschl (2002) *Nat. Biotechnol.*, 20: 446-448; Brummelkamp et al. (2002) *Science* 296: 550 553; Miyagishi et al. (2002) *Nat. Biotechnol.* 20: 497-500; Paddison et al. (2002) *Genes Dev.* 16: 948-958; Lee et al. (2002) *Nat. Biotechnol.* 20: 500-505; Paul et al. (2002) *Nat. Biotechnol.* 20: 505-508, and the like).

In one illustrative embodiment, a plasmid comprising nucleic acid sequences for expressing an siRNA for inhibiting Mylip/Idol comprises a sense RNA strand coding sequence in operable connection with a polyT termination sequence under the control of a human U6 RNA promoter, and an antisense RNA strand coding sequence in operable connection with a polyT termination sequence under the control of a human U6 RNA promoter. The plasmid is ultimately intended for use in producing an recombinant adeno-associated viral vector comprising the same nucleic acid sequences for expressing the siRNA As used herein, "in operable connection with a polyT termination sequence" means that the nucleic acid sequences encoding the sense or antisense strands are adjacent to the polyT termination signal in the 5' direction or sufficiently close so that during transcription of the sense or antisense sequences from the plasmid, the polyT termination signals act to terminate transcription after the desired product is transcribed.

As used herein, "under the control" of a promoter means that the nucleic acid sequences encoding the sense or antisense strands are located 3' of the promoter, so that the promoter can initiate transcription of the sense or antisense coding sequences.

In various embodiments the siRNA can be expressed from recombinant viral vectors intracellularly at or near the target site(s) in vivo. The recombinant viral vectors comprise sequences encoding the siRNA of the invention and any suitable promoter for expressing the siRNA sequences. Suitable promoters include, but are not limited to, the U6 or H1 RNA pol III promoter sequences and the cytomegalovirus promoter. Selection of other suitable promoters is within the skill in the art. The recombinant viral vectors can also comprise inducible or regulatable promoters for expression of the siRNA in a particular tissue or in a particular intracellular environment. The use of recombinant viral vectors to deliver siRNA of the invention to cells in vivo is discussed in more detail below.

The siRNA can be expressed from a recombinant viral vector either as two separate, complementary RNA molecules, or as a single RNA molecule with two complementary regions.

Any viral vector capable of accepting the coding sequences for the siRNA molecule(s) to be expressed can be used, for example vectors derived from adenovirus (AV); adeno-associated virus (AAV); retroviruses (e.g. lentiviruses (LV), Rhabdoviruses, murine leukemia virus); herpes virus, and the like. The tropism of the viral vectors can also be modified by pseudotyping the vectors with envelope proteins or other surface antigens from other viruses. For example, an AAV vector can be pseudotyped with surface proteins from vesicular stomatitis virus (VSV), rabies, Ebola, Mokola, and the like.

Selection of recombinant viral vectors suitable for use in methods for inserting nucleic acid sequences for expressing the siRNA into the vector, and methods of delivering the viral vector to the cells of interest are within the skill in the art (see, e.g., Domburg (1995) *Gene Therap.* 2: 301-310; Eglitis (1988) *Biotechniques* 6: 608-614; Miller (1990) *Hum. Gene Therap.* 1: 5-14; Anderson (1998) *Nature* 392: 25-30, and the like).

In certain embodiments suitable viral vectors include those derived from AV and AAV. In one illustrative embodiment, the siRNA of the invention is expressed as two separate, complementary single-stranded RNA molecules from a recombinant AAV vector comprising, for example, either the U6 or H1 RNA promoters, or the cytomegalovirus (CMV) promoter. A suitable AV vector for expressing the siRNA, a method for constructing the recombinant AV vector, and a method for delivering the vector into target cells, are described in Xia et al. (2002) *Nat. Biotech.* 20: 1006 1010.

Suitable AAV vectors for expressing the siRNA, methods for constructing the recombinant AV vector, and methods for delivering the vectors into target cells are also described in Samulski et al. (1987) *J. Virol.* 61: 3096-3101; Fisher et al. (1996) *J. Virol.*, 70: 520-532; Samulski et al. (1989) *J. Virol.* 63: 3822-3826; U.S. Pat. Nos. 5,252,479 and 5,139,941; International Patent Application Nos. WO 1994/013788; and WO 1993/024641, and the like.

The ability of an siRNA containing a given target sequence to cause RNAi-mediated degradation of the target mRNA can be evaluated using standard techniques for measuring the levels of RNA or protein in cells. For example, siRNA can be delivered to cultured cells, and the levels of target mRNA can be measured by Northern blot or dot blotting techniques, or by quantitative RT-PCR. Alternatively, the levels of Mylip/Idol in cells can be measured by ELISA or Western blot.

RNAi-mediated degradation of target Mylip/Idol mRNA by an siRNA containing a given target sequence can also be evaluated with suitable animal models of aging.

In certain embodiments the siRNA can be delivered as a small hairpin RNA or short hairpin RNA (shRNA). shRNA is a sequence of RNA that makes a tight hairpin turn that can be used to silence gene expression via RNA interference. In typical embodiments, shRNA uses a vector introduced into cells and utilizes the U6 promoter to ensure that the shRNA is always expressed. This vector is usually passed on to daughter cells, allowing the gene silencing to be inherited. The shRNA hairpin structure is cleaved by the cellular machinery into siRNA, which is then bound to the RNA-induced silencing complex (RISC). This complex binds to and cleaves mRNAs that match the siRNA that is bound to it.

The shRNA/siRNA described herein target and cause the RNAi-mediated degradation of EIF4A, or alternative splice forms, mutants or cognates thereof. Degradation of the target mRNA by the present siRNA reduces the production of a functional gene product from the EIF4A gene. Thus, methods are provided for inhibiting expression of EIF4A in a subject, comprising administering an effective amount of an EIF4A siRNA to the subject, such that the target mRNA is degraded.

It is understood that the siRNA of described herein can degrade the target mRNA in substoichiometric amounts. Without wishing to be bound by any theory, it is believed that the siRNA described herein cause degradation of the target mRNA in a catalytic manner. Thus, compared to standard anti-angiogenic therapies, significantly less siRNA needs to be delivered to have a therapeutic effect.

One skilled in the art can readily determine an effective amount of the siRNA to be administered to a given subject, by taking into account factors such as the size and weight of the subject; the age, health and sex of the subject; the route of administration; and whether the administration is regional or systemic.

siRNAs suitable to inhibit Mylip are known to those of skill and a number are commercially available. Thus, for example, Table 1, illustrates data from the SIGMA® online catalogue describing a number of Mylip siRNAs and shRNAs.

TABLE 1

Information about Mylip and siRNA for Mylip from SIGMA ® catalogue.

Properties

| | |
|---|---|
| Official Symbol | MYLIP |
| Species | *Homo sapiens* |
| Entrez Gene ID | 29116 |
| Alternate Symbol | MYLIP; MIR |
| Refseq ID(s) | NM_013262 |
| Other Designations | band 4.1 superfamily member BZF-1; cellular modulator of immune recognition (c-MIR) |
| Accession No.(s) | AF006003; AF187016; AF212221; AF258586; AJ420601; AK026739; AK074391; BC002860; BT007055; NM_013262 |
| Protein ID(s) | NP_037394 |
| Homolog(s) | Mylip(mouse); Mylip_predicted(Rat) |
| Function(s) | cytoskeleton; ligase; ubiquitin pathway |
| Available Product(s) | siRNA; MISSION ® shRNA panels; shRNA; MISSION ® siRNA panels |

Related Products
MISSION ® shRNA

| Type | Description |
|---|---|
| SHGLY-NM_013262 | MISSION ® shRNA Bacterial Glycerol Stock |
| SHVRS-NM_013262 | MISSION ® shRNA Lentiviral Transdution Particles |
| SHDNA-NM_013262 | MISSION ® shRNA Plasmid DNA |

| Product # | Description |
|---|---|
| MISSION ® shRNA panels | |
| SH2111 | MISSION ® shRNA Human gene family set, bacterial glycerol stock, ubiquitin ligases (E1, E2, E3) |
| MISSION ® siRNA panels | |
| SI00100 | MISSION ® siRNA Human druggable genome library, 6650 targets |
| SI01100 | MISSION ® siRNA Human gene family panels ligase panel, 949 targets | siRNA

| siRNA ID | Refseq ID | Approx. siRNA start | | Ranking |
|---|---|---|---|---|
| SASI_Hs01_00172371 | NM_013262 | 1418 | MISSION ® siRNA | 1 |
| SASI_Hs01_00172372 | NM_013262 | 491 | MISSION ® siRNA | 2 |
| SASI_Hs01_00172373 | NM_013262 | 384 | MISSION ® siRNA | 3 |
| SASI_Hs01_00172374 | NM_013262 | 371 | MISSION ® siRNA | 4 |
| SASI_Hs01_00172375 | NM_013262 | 886 | MISSION ® siRNA | 5 |
| SASI_Hs01_00172376 | NM_013262 | 1161 | MISSION ® siRNA | 6 |
| SASI_Hs01_00172377 | NM_013262 | 878 | MISSION ® siRNA | 7 |
| SASI_Hs01_00172378 | NM_013262 | 639 | MISSION ® siRNA | 8 |
| SASI_Hs01_00172379 | NM_013262 | 345 | MISSION ® siRNA | 9 |
| SASI_Hs01_00172370 | NM_013262 | 389 | MISSION ® siRNA | 10 |

Double stranded RNA (dsRNA) can be introduced into cells by any of a wide variety of means. Such methods include, but are not limited to lipid-mediated transfection (e.g. using reagents such as lipofectamine), liposome delivery, dendrimer-mediated transfection, and gene transfer using a viral (e.g., adenoviral vector) or bacterial vector. Where the vector expresses (transcribes) a single-stranded RNA, the vector can be designed to transcribe two complementary RNA strands that will then hybridize to form a double-stranded RNA.

Antisense Approaches.

In various embodiments Mylip expression can be down-regulated or entirely inhibited by the use of antisense molecules. An "antisense sequence or antisense nucleic acid" is a nucleic acid that is complementary to the coding Mylip mRNA nucleic acid sequence or a subsequence thereof. Binding of the antisense molecule to the Mylip mRNA interferes with normal translation of the Mylip transcription factor.

Thus, in accordance with certain embodiments of this invention, antisense molecules include oligonucleotides and oligonucleotide analogs that are hybridizable with Mylip messenger RNA. This relationship is commonly denominated as "antisense." The oligonucleotides and oligonucleotide analogs are able to inhibit the function of the RNA, either its translation into protein, its translocation into the cytoplasm, or any other activity necessary to its overall biological function. The failure of the messenger RNA to perform all or part of its function results in a reduction or complete inhibition of expression of Mylip polypeptides.

In the context of this invention, the term "oligonucleotide" refers to a polynucleotide formed from naturally-occurring bases and/or cyclofuranosyl groups joined by native phosphodiester bonds. This term effectively refers to naturally-occurring species or synthetic species formed from naturally-occurring subunits or their close homologs. The term "oligonucleotide" may also refer to moieties which function similarly to oligonucleotides, but which have non naturally-occurring portions. Thus, oligonucleotides may have altered sugar moieties or inter-sugar linkages. Exemplary among these are the phosphorothioate and other sulfur containing species that are known for use in the art. In accordance with some preferred embodiments, at least one of the phosphodiester bonds of the oligonucleotide has been substituted with a structure which functions to enhance the ability of the compositions to penetrate into the region of cells where the RNA whose activity is to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with structures which are, at once, substantially non-ionic and non-chiral, or with structures which are chiral and enantiomerically specific. Persons of ordinary skill in the art will be able to select other linkages for use in the practice of the invention.

In one embodiment, the internucleotide phosphodiester linkage is replaced with a peptide linkage. Such peptide nucleic acids tend to show improved stability, penetrate the cell more easily, and show enhances affinity for their target. Methods of making peptide nucleic acids are known to those of skill in the art (see, e.g., U.S. Pat. Nos. 6,015,887, 6,015,710, 5,986,053, 5,977,296, 5,902,786, 5,864,010, 5,786,461, 5,773,571, 5,766,855, 5,736,336, 5,719,262, and 5,714,331).

Oligonucleotides may also include species that include at least some modified base forms. Thus, purines and pyrimidines other than those normally found in nature may be so employed. Similarly, modifications on the furanosyl portions of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)[n]NH_2$ or $O(CH_2)[n]CH_3$, where n is from 1 to about 10, and other substituents having similar properties.

Such oligonucleotides are best described as being functionally interchangeable with natural oligonucleotides or synthesized oligonucleotides along natural lines, but which have one or more differences from natural structure. All such analogs are comprehended by this invention so long as they function effectively to hybridize with messenger RNA of MYLIP to inhibit the function of that RNA.

The oligonucleotides in accordance with certain embodiments of this invention comprise from about 3 to about 50 subunits. It is more preferred that such oligonucleotides and analogs comprise from about 8 to about 25 subunits and still more preferred to have from about 12 to about 20 subunits. As will be appreciated, a subunit is a base and sugar combination suitably bound to adjacent subunits through phosphodiester or other bonds. The oligonucleotides used in accordance with this invention can be conveniently and routinely made through the well-known technique of solid phase synthesis. Equipment for such syntheses is sold by several vendors (e.g. Applied Biosystems). Any other means for such synthesis may also be employed, however, the actual synthesis of the oligonucleotides is well within the talents of the routineer. It is also will known to prepare other oligonucleotide such as phosphorothioates and alkylated derivatives.

Ribozymes.

In another approach, Mylip expression can be inhibited by the use of ribozymes. As used herein, "ribozymes" include RNA molecules that contain antisense sequences for specific recognition, and an RNA-cleaving enzymatic activity. The catalytic strand cleaves a specific site in a target (Mylip) RNA, preferably at greater than stoichiometric concentration. Two "types" of ribozymes are particularly useful in this invention, the hammerhead ribozyme (Rossi et al. (1991) *Pharmac. Ther.* 50: 245-254) and the hairpin ribozyme (Hampel et al. (1990) *Nucl. Acids Res.* 18: 299-304, and U.S. Pat. No. 5,254,678).

Because both hammerhead and hairpin ribozymes are catalytic molecules having antisense and endoribonucleotidase activity, ribozyme technology has emerged as a potentially powerful extension of the antisense approach to gene inactivation. The ribozymes of the invention typically consist of RNA, but such ribozymes may also be composed of nucleic acid molecules comprising chimeric nucleic acid sequences (such as DNA/RNA sequences) and/or nucleic acid analogs (e.g., phosphorothioates).

Accordingly, within one aspect of the present invention ribozymes have the ability to inhibit Mylip expression. Such ribozymes may be in the form of a "hammerhead" (for example, as described by Forster and Symons (1987) *Cell* 48: 211-220, Haseloff and Gerlach (1988) *Nature* 328: 596-600; Walbot and Bruening (1988) *Nature* 334: 196; Haseloff and Gerlach (1988) *Nature* 334: 585) or a "hairpin" (see, e.g. U.S. Pat. No. 5,254,678 and Hampel et al., European Patent Publication No. 0 360 257, published Mar. 26, 1990), and have the ability to specifically target, cleave and Mylip nucleic acids.

Ribozymes, as well as DNA encoding such ribozymes and other suitable nucleic acid molecules can be chemically synthesized using methods well known in the art for the synthesis of nucleic acid molecules. Alternatively, Promega, Madison, Wis., USA, provides a series of protocols suitable for the production of RNA molecules such as ribozymes. The ribozymes also can be prepared from a DNA molecule or other nucleic acid molecule (which, upon transcription, yields an RNA molecule) operably linked to an RNA polymerase promoter, e.g., the promoter for T7 RNA polymerase or SP6 RNA polymerase. Such a construct may be referred to as a vector. Accordingly, also provided by this invention are nucleic acid molecules, e.g., DNA or cDNA, coding for the ribozymes of this invention. When the vector also contains an RNA polymerase promoter operably linked to the DNA molecule, the ribozyme can be produced in vitro upon incubation with the RNA polymerase and appropriate nucleotides. In a separate embodiment, the DNA may be inserted into an expression cassette (see, e.g., Cotten and Birnstiel (1989) *EMBO J* 8(12):3861-3866; Hempel et al. (1989) *Biochem.* 28: 4929-4933, etc.).

After synthesis, the ribozyme can be modified by ligation to a DNA molecule having the ability to stabilize the ribozyme and make it resistant to RNase. Alternatively, the ribozyme can be modified to the phosphothio analog for use in liposome delivery systems. This modification also renders the ribozyme resistant to endonuclease activity.

The ribozyme molecule also can be in a host prokaryotic or eukaryotic cell in culture or in the cells of an organism/patient. Appropriate prokaryotic and eukaryotic cells can be transfected with an appropriate transfer vector containing the DNA molecule encoding a ribozyme of this invention. Alternatively, the ribozyme molecule, including nucleic acid molecules encoding the ribozyme, may be introduced into the host cell using traditional methods such as transformation using calcium phosphate precipitation (Dubensky et al. (1984) *Proc. Natl. Acad. Sci., USA*, 81: 7529-7533), direct microinjection of such nucleic acid molecules into intact target cells (Acsadi et al. (1991) *Nature* 352: 815-818), and electroporation whereby cells suspended in a conducting solution are subjected to an intense electric field in order to transiently polarize the membrane, allowing entry of the nucleic acid molecules. Other procedures include the use of nucleic acid molecules linked to an inactive adenovirus (Cotton et al. (1990) *Proc. Natl. Acad. Sci., USA*, 89:6094), lipofection (Felgner et al. (1989) *Proc. Natl. Acad. Sci. USA* 84: 7413-7417), microprojectile bombardment (Williams et al. (1991) *Proc. Natl. Acad. Sci., USA*, 88: 2726-2730), polycation compounds such as polylysine, receptor specific ligands, liposomes entrapping the nucleic acid molecules, spheroplast fusion whereby *E. coli* containing the nucleic acid molecules are stripped of their outer cell walls and fused to animal cells using polyethylene glycol, viral transduction, (Cline et al., (1985) *Pharmac. Ther.* 29: 69; and Friedmann et al. (1989) *Science* 244: 1275), and DNA ligand (Wu et al (1989) *J. Biol. Chem.* 264: 16985-16987), as well as psoralen inactivated viruses such as Sendai or Adenovirus. In one preferred embodiment, the ribozyme is introduced into the host cell utilizing a lipid, a liposome or a retroviral vector.

When the DNA molecule is operatively linked to a promoter for RNA transcription, the RNA can be produced in the host cell when the host cell is grown under suitable conditions favoring transcription of the DNA molecule. The vector can be, but is not limited to, a plasmid, a virus, a retrotransposon or a cosmid. Examples of such vectors are disclosed in U.S. Pat. No. 5,166,320. Other representative vectors include, but are not limited to adenoviral vectors (e.g., WO 94/26914, WO 93/9191; Kolls et al. (1994) PNAS 91(1):215-219; Kass-Eisler et al., (1993) *Proc. Natl. Acad. Sci., USA*, 90(24): 11498-502, Guzman et al. (1993) *Circulation* 88(6): 2838-48, 1993; Guzman et al. (1993) *Cir. Res.* 73(6):1202-1207, 1993; Zabner et al. (1993) *Cell* 75(2): 207-216; Li et al. (1993) *Hum Gene Ther.* 4(4): 403-409; Caillaud et al. (1993) *Eur. J Neurosci.* 5(10): 1287-1291), adeno-associated vector type 1 ("AAV-1") or adeno-associated vector type 2 ("AAV-2") (see WO 95/13365; Flotte et al. (1993) *Proc. Natl. Acad. Sci., USA*, 90(22):10613-10617), retroviral vectors (e.g., EP 0 415 731; WO 90/07936; WO 91/02805; WO 94/03622; WO 93/25698; WO 93/25234; U.S. Pat. No. 5,219,740; WO 93/11230; WO 93/10218) and herpes viral vectors (e.g., U.S. Pat. No. 5,288,641). Methods of utilizing such vectors in gene therapy are well known in the art, see, for example, Larrick and Burck (1991) *Gene Therapy: Application of Molecular Biology*, Elsevier Science Publishing Co., Inc., New York, N.Y, and Kreigler (1990) *Gene Transfer and Expression: A Laboratory Manual*, W.H. Freeman and Company, New York.

To produce ribozymes in vivo utilizing vectors, the nucleotide sequences coding for ribozymes are preferably placed under the control of a strong promoter such as the lac, SV40 late, SV40 early, or lambda promoters. Ribozymes are then produced directly from the transfer vector in vivo.

Inhibiting Mylip/Idol LDLR Interaction.

As shown in Example 2, the residues conserved between LDLR, VLDLR and apoER2 are important for Idol recognition. We have further determined that the FERM domain of Idol is critical for interaction with the LDLR. Disruption of Idol FERM domain interaction with these LDLR residues using a small molecule would inactivate the Idol-LDLR pathway.

The Idol-LDLR recognition sequence can be used as the basis for screens aimed at identifying small molecules that specifically disrupted Idol-LDLR interaction e.g, by targeting this region of the LDLR.

Accordingly in certain embodiment, it is contemplated that Idol/LDLR inhibition can be achieved by using agents (e.g., antibodies, small organic molecules, etc.) that bind the FERM domain of Idol or that bind/interact with the region of LDLR that interacts with Idol.

Mylip Inhibitors

In certain embodiments, it is contemplated that small organic molecules can be used in inhibit Mylip expression and/or activity. It is believed inhibitors identified using, for example, the screening methods described herein can readily be used to inhibit Mylip.

III. Modes of Administration.

The mode of administration of the Mylip inhibitor (agent that inhibits expression and/or activity of Mylip) depends on the nature of the particular agent. Antisense molecules, catalytic RNAs (ribozymes), catalytic DNAs, small organic molecules, RNAi, and other molecules (e.g. lipids, antibodies, etc.) used as MyLip inhibitors can be formulated as pharmaceuticals (e.g. with suitable excipient) and delivered using standard pharmaceutical formulation and delivery methods as described below. Antisense molecules, catalytic RNAs (ribozymes), catalytic DNAs, and additionally, knockout constructs, and constructs encoding intrabodies can be delivered and (if necessary) expressed in target cells (e.g. hepatic cells) using methods of gene therapy, e.g. as described below.

A) Pharmaceutical Formulations.

The compositions of the invention include bulk drug compositions useful in the manufacture of non-pharmaceutical compositions (e.g., impure or non-sterile compositions) and pharmaceutical compositions (i.e., compositions that are suitable for administration to a subject or patient) that can be used directly and/or in the preparation of unit dosage forms. Such compositions comprise a therapeutically effective amount of one or more therapeutic agents (e.g. Mylip inhibitors) disclosed herein or a combination of the agent(s) and a pharmaceutically acceptable carrier. Preferably, compositions of the invention comprise a therapeutically effective amount of an inhibitor of expression and/or activity of Mylip inhibitors and optionally, a pharmaceutically acceptable carrier.

The agents that inhibit expression or activity of Mylip used in the methods of this invention, (e.g. to mitigate one or more symptoms of hypercholesterolemia) can be prepared and administered in a wide variety of rectal, oral and parenteral dosage forms for treating and preventing neurological damage, increased vascular permeability associated with trauma, and the like. One or more Mylip inhibitors can be administered by injection, that is, intravenously, intramuscularly, intracutaneously, subcutaneously, intraduodenally, or intraperitoneally. Also, the compounds can be administered by inhalation, for example, intranasally. Additionally, the compounds can be administered transdermally.

In certain embodiments, the term "pharmaceutically acceptable" means approved by a regulatory agency of the Federal or a state government or listed in the U.S. Pharmacopeia or other generally recognized pharmacopeia for use in animals, and more particularly in humans, or suitable for administration to an animal or human. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of the compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Pharmaceutical compositions comprising the inhibitors of Mylip expression and/or activity can be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the molecules into preparations that can be used pharmaceutically. Proper formulation is dependent upon the route of administration chosen.

For topical or transdermal administration, the Mylip inhibitors can be formulated as solutions, gels, ointments, creams, lotion, emulsion, suspensions, etc. as are well-known in the art. Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the Mylip inhibitors an be formulated in aqueous solutions, e.g., in physiologically compatible buffers such as Hanks's solution, Ringer's solution, or physiological saline buffer. The solution can contain formulatory agents such as suspending, stabilizing and/or dispersing agents. Alternatively, compositions comprising the inhibitors of Mylip expression and/or activity can be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the Mylip inhibitors can be readily formulated by combining the inhibitors with pharmaceutically acceptable carriers well known in the art. Such carriers enable the inhibitors of to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like can be added.

For buccal administration, the Mylip inhibitors can take the form of tablets, lozenges, etc. formulated in conventional manner.

For administration by inhalation, the Mylip inhibitors for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator may be formulated containing a powder mix of the Mylip inhibitors and a suitable powder base such as lactose or starch.

The Mylip inhibitors can also be formulated in rectal or vaginal compositions such as suppositories or retention enemas, e.g., containing conventional suppository bases In various embodiments other pharmaceutical delivery systems can be employed. Liposomes and emulsions are well known examples of delivery vehicles that may be used to deliver the Mylip inhibitors. Certain organic solvents such as dimethylsulfoxide also may be employed, although usually at the cost of greater toxicity. Additionally, the Mylip inhibitors can be delivered using a sustained-release system, such as semipermeable matrices of solid polymers containing the therapeutic agent. Various sustained-release materials have been established and are well known by those skilled in the art. Sustained-release capsules may, depending on their chemical nature, release the Mylip inhibitors for a few days, a few weeks, or up to over 100 days. Depending on the chemical nature and the biological stability of the inhibitors additional strategies for stabilization can be employed.

B) "Genetic" Delivery Methods.

As indicated above, antisense molecules, catalytic RNAs (ribozymes), catalytic DNAs, RNAi, and additionally, knockout constructs, and constructs encoding intrabodies can be delivered and transcribed and/or expressed in target cells (e.g. hepatic cells) using methods of gene therapy. Thus, in certain preferred embodiments, the nucleic acids encoding knockout constructs, intrabodies, antisense molecules, catalytic RNAs or DNAs, etc. are cloned into gene therapy vectors that are competent to transfect cells (such as human or other mammalian cells) in vitro and/or in vivo.

Many approaches for introducing nucleic acids into cells in vivo, ex vivo and in vitro are known. These include lipid or liposome based gene delivery (WO 96/18372; WO 93/24640; Mannino and Gould-Fogerite (1988) *BioTechniques* 6(7): 682-691; Rose U.S. Pat. No. 5,279,833; WO 91/06309; and Felgner et al. (1987) *Proc. Natl. Acad. Sci. USA* 84: 7413-7414) and replication-defective retroviral vectors harboring a therapeutic polynucleotide sequence as part of the retroviral genome (see, e.g., Miller et al. (1990) *Mol. Cell. Biol.* 10:4239 (1990); Kolberg (1992) *J. NIH Res.* 4: 43, and Cornetta et al. (1991) *Hum. Gene Ther.* 2: 215).

For a review of gene therapy procedures, see, e.g., Anderson, *Science* (1992) 256: 808-813; Nabel and Felgner (1993) *TIBTECH* 11: 211-217; Mitani and Caskey (1993) *TIBTECH* 11: 162-166; Mulligan (1993) *Science*, 926-932; Dillon (1993) *TIBTECH* 11: 167-175; Miller (1992) *Nature* 357: 455-460; Van Brunt (1988) *Biotechnology* 6(10): 1149-1154; Vigne (1995) Restorative Neurology and Neuroscience 8: 35-36; Kremer and Perricaudet (1995) *British Medical Bulletin* 51(1) 31-44; Haddada et al. (1995) in *Current Topics in Microbiology and Immunology*, Doerfler and Böhm (eds) Springer-Verlag, Heidelberg Germany; and Yu et al., (1994) *Gene Therapy*, 1:13-26.

Widely used vector systems include, but are not limited to adenovirus, adeno associated virus, and various retroviral expression systems. The use of adenoviral vectors is well known to those of skill and is described in detail, e.g., in WO 96/25507. Particularly preferred adenoviral vectors are described by Wills et al. (1994) *Hum. Gene Therap.* 5: 1079-1088.

Adeno-associated virus (AAV)-based vectors used to transduce cells with target nucleic acids, e.g., in the in vitro production of nucleic acids and peptides, and in in vivo and ex vivo gene therapy procedures are describe, for example, by West et al. (1987) *Virology* 160:38-47; Carter et al. (1989) U.S. Pat. No. 4,797,368; Carter et al. WO 93/24641 (1993); Kotin (1994) *Human Gene Therapy* 5:793-801; Muzyczka (1994) *J. Clin. Invst.* 94:1351 for an overview of AAV vectors. Lebkowski, U.S. Pat. No. 5,173,414; Tratschin et al. (1985) *Mol. Cell. Biol.* 5(11):3251-3260; Tratschin, et al. (1984) *Mol. Cell. Biol.*, 4: 2072-2081; Hermonat and Muzyczka (1984) *Proc. Natl. Acad. Sci. USA*, 81: 6466-6470; McLaughlin et al. (1988) and Samulski et al. (1989) *J. Virol.*, 63:03822-3828. Cell lines that can be transformed by rAAV include those described in Lebkowski et al. (1988) *Mol. Cell. Biol.*, 8:3988-3996.

Widely used retroviral vectors include those based upon murine leukemia virus (MuLV), gibbon ape leukemia virus (GaLV), Simian Immunodeficiency virus (SIV), human immunodeficiency virus (HIV), alphavirus, and combinations thereof (see, e.g., Buchscher et al. (1992) *J. Virol.* 66(5) 2731-2739; Johann et al. (1992) *J. Virol.* 66 (5):1635-1640 (1992); Sommerfelt et al., (1990) *Virol.* 176:58-59; Wilson et al. (1989) *J. Virol.* 63:2374-2378; Miller et al., *J. Virol.* 65:2220-2224 (1991); Wong-Staal et al., PCT/US94/05700, and Rosenburg and Fauci (1993) in *Fundamental Immunology*, Third Edition Paul (ed) Raven Press, Ltd., New York and the references therein, and Yu et al. (1994) *Gene Therapy*, supra; U.S. Pat. No. 6,008,535, and the like). Other suitable viral vectors include, but are not limited to herpes virus, lentivirus, and vaccinia virus.

Alone, or in combination with viral vectors, a number of non-viral vectors are also useful for transfecting cells to express constructs that block or inhibit Mylip expression. Suitable non-viral vectors include, but are not limited to, plasmids, cosmids, phagemids, liposomes, water-oil emulsions, polethylene imines, biolistic pellets/beads, and dendrimers.

Liposomes were first described in 1965 as a model of cellular membranes and quickly were applied to the delivery of substances to cells. Liposomes entrap DNA by one of two mechanisms which has resulted in their classification as either cationic liposomes or pH-sensitive liposomes. Cationic liposomes are positively charged liposomes which interact with the negatively charged DNA molecules to form a stable complex. Cationic liposomes typically consist of a positively charged lipid and a co-lipid. Commonly used co-lipids include dioleoyl phosphatidylethanolamine (DOPE) or dioleoyl phosphatidylcholine (DOPC). Co-lipids, also called helper lipids, are in most cases required for stabilization of liposome complex. A variety of positively charged lipid formulations are commercially available and many other are under development. Two of the most frequently cited cationic lipids are lipofectamine and lipofectin. Lipofectin is a commercially available cationic lipid first reported by Phil Felgner in 1987 to deliver genes to cells in culture. Lipofectin is a mixture of N-[1-(2,3-dioleyloyx) propyl]-N-N-N-trimethyl ammonia chloride (DOTMA) and DOPE.

DNA and lipofectin or lipofectamine interact spontaneously to form complexes that have a 100% loading efficiency. In other words, essentially all of the DNA is complexed with the lipid, provided enough lipid is available. It is assumed that the negative charge of the DNA molecule interacts with the positively charged groups of the DOTMA. The lipid:DNA ratio and overall lipid concentrations used in forming these complexes are extremely important for efficient gene transfer and vary with application. Lipofectin has been used to deliver linear DNA, plasmid DNA, and RNA to a variety of cells in culture. Shortly after its introduction, it was shown that lipofectin could be used to deliver genes in vivo. Following intravenous administration of lipofectin-DNA complexes, both the lung and liver showed marked affinity for uptake of these complexes and transgene expression. Injection of these complexes into other tissues has had varying results and, for the most part, are much less efficient than lipofectin-mediated gene transfer into either the lung or the liver.

PH-sensitive, or negatively-charged liposomes, entrap DNA rather than complex with it. Since both the DNA and the lipid are similarly charged, repulsion rather than complex formation occurs. Yet, some DNA does manage to get entrapped within the aqueous interior of these liposomes. In some cases, these liposomes are destabilized by low pH and hence the term pH-sensitive. To date, cationic liposomes have been much more efficient at gene delivery both in vivo and in vitro than pH-sensitive liposomes. pH-sensitive liposomes have the potential to be much more efficient at in vivo DNA delivery than their cationic counterparts and should be able to do so with reduced toxicity and interference from serum protein.

In another approach dendrimers complexed to the DNA have been used to transfect cells. Such dendrimers include, but are not limited to, "starburst" dendrimers and various dendrimer polycations.

Dendrimer polycations are three dimensional, highly ordered oligomeric and/or polymeric compounds typically formed on a core molecule or designated initiator by reiterative reaction sequences adding the oligomers and/or polymers and providing an outer surface that is positively changed.

These dendrimers may be prepared as disclosed in PCT/US83/02052, and U.S. Pat. Nos. 4,507,466, 4,558,120, 4,568,737, 4,587,329, 4,631,337, 4,694,064, 4,713,975, 4,737,550, 4,871,779, 4,857,599.

Typically, the dendrimer polycations comprise a core molecule upon which polymers are added. The polymers may be oligomers or polymers which comprise terminal groups capable of acquiring a positive charge. Suitable core molecules comprise at least two reactive residues which can be utilized for the binding of the core molecule to the oligomers and/or polymers. Examples of the reactive residues are hydroxyl, ester, amino, imino, imido, halide, carboxyl, carboxyhalide maleimide, dithiopyridyl, and sulfhydryl, among others. Preferred core molecules are ammonia, tris-(2-aminoethyl)amine, lysine, ornithine, pentaerythritol and ethylenediamine, among others. Combinations of these residues are also suitable as are other reactive residues.

Oligomers and polymers suitable for the preparation of the dendrimer polycations of the invention are pharmaceutically-acceptable oligomers and/or polymers that are well accepted in the body. Examples of these are polyamidoamines derived from the reaction of an alkyl ester of an α,β-ethylenically unsaturated carboxylic acid or an α,β-ethylenically unsaturated amide and an alkylene polyamine or a polyalkylene polyamine, among others. Preferred are methyl acrylate and ethylenediamine. The polymer is preferably covalently bound to the core molecule.

The terminal groups that may be attached to the oligomers and/or polymers should be capable of acquiring a positive charge. Examples of these are azoles and primary, secondary, tertiary and quaternary aliphatic and aromatic amines and azoles, which may be substituted with S or O, guanidinium, and combinations thereof. The terminal cationic groups are preferably attached in a covalent manner to the oligomers and/or polymers. Preferred terminal cationic groups are amines and guanidinium. However, others may also be utilized. The terminal cationic groups may be present in a proportion of about 10 to 100% of all terminal groups of the oligomer and/or polymer, and more preferably about 50 to 100%.

The dendrimer polycation may also comprise 0 to about 90% terminal reactive residues other than the cationic groups. Suitable terminal reactive residues other than the terminal cationic groups are hydroxyl, cyano, carboxyl, sulfhydryl, amide and thioether, among others, and combinations thereof. However others may also be utilized.

The dendrimer polycation is generally and preferably non-covalently associated with the polynucleotide. This permits an easy disassociation or disassembling of the composition once it is delivered into the cell. Typical dendrimer polycation suitable for use herein have a molecular weight ranging from about 2,000 to 1,000,000 Da, and more preferably about 5,000 to 500,000 Da. However, other molecule weights are also suitable. Preferred dendrimer polycations have a hydrodynamic radius of about 11 to 60 Å, and more preferably about 15 to 55 Å. Other sizes, however, are also suitable. Methods for the preparation and use of dendrimers in gene therapy are well known to those of skill in the art and describe in detail, for example, in U.S. Pat. No. 5,661,025.

Where appropriate, two or more types of vectors can be used together. For example, a plasmid vector may be used in conjunction with liposomes. In the case of non-viral vectors, nucleic acid may be incorporated into the non-viral vectors by any suitable means known in the art. For plasmids, this typically involves ligating the construct into a suitable restriction site. For vectors such as liposomes, water-oil emulsions, polyethylene amines and dendrimers, the vector and construct may be associated by mixing under suitable conditions known in the art.

C) Effective Dosages.

The inhibitors of Mylip expression and/or activity will generally be used in an amount effective to achieve the intended purpose (e.g. to provided for inhibiting LDL receptor degradation and/or promoting LDL uptake in a mammal, and/or one mitigating or more symptoms of hypercholesterolemia in a mammal). In certain embodiments, the Mylip inhibitors utilized in the methods of this invention are administered at a dose that is effective to partially or fully for inhibit LDL receptor degradation and/or promote LDL uptake in a mammal, and/or one mitigate one or more symptoms of hypercholesterolemia in a mammal (e.g., a statistically significant decrease at the 90%, more preferably at the 95%, and most preferably at the 98% or 99% confidence level). In certain embodiments the compounds can also be used prophalactically at the same dose levels.

Typically, the inhibitors of Mylip expression and/or activity, or pharmaceutical compositions thereof, are administered or applied in a therapeutically effective amount. A therapeutically effective amount is an amount effective that is effective to partially or fully for inhibit LDL receptor degradation and/or promote LDL uptake in a mammal, and/or one mitigate one or more symptoms of hypercholesterolemia in a mammal. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One skilled in the art could readily optimize administration to humans based on animal data.

Dosage amount and interval may be adjusted individually to provide plasma levels of the inhibitors which are sufficient to maintain therapeutic effect.

In certain embodiments, an initial dosage of about 1 µg preferably from about 1 mg to about 1000 mg per kilogram daily will be effective. A daily dose range of about 5 to about 75 mg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 to about 500 mg/kg, and ideally about 25 to about 250 mg/kg.

In cases of local administration or selective uptake, the effective local concentration of the inhibitors may not be related to plasma concentration. One skilled in the art will be able to optimize therapeutically effective local dosages without undue experimentation. The amount of inhibitor administered will, of course, be dependent on the subject being treated, on the subject's weight, the severity of the affliction, the manner of administration and the judgment of the prescribing physician.

The therapy may be repeated intermittently. The therapy may be provided alone or in combination with other drugs and/or procedures.

D) Toxicity.

Preferably, a therapeutically effective dose of the inhibitors of Mylip expression and/or activity described herein will provide therapeutic benefit without causing substantial toxicity.

Toxicity of the inhibitors described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Inhibitors which exhibit high therapeutic indices are preferred. The data obtained from these cell culture assays and animal studies can be used in formulating a dosage range that is not toxic for use in human. The dosage of the inhibitors described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p. 1).

IV. Mylip Knock-Out and Knock-In Cells, Tissues, and/or Animals.

In certain embodiments, cells, tissues, and/or animals transfected with a construct that expresses Idol are provided. In certain embodiments, cells, tissues and/or animals transfected with a construct that disrupts the Idol gene and thereby reduces Idol expression are provided.

Idol Knock-Ins.

In certain embodiments, cells, tissues, and/or animals comprising a construct that encodes and expresses Idol are contemplated. In various embodiments, these cells, tissues and/or animals, express Idol at a level higher than in the untrasnfected cell, tissue, and/or animal. Typically this involves creating a DNA sequence that encodes Idol, placing the DNA in an expression cassette under the control of a particular promoter, and transfecting a cell (in vitro or in vivo) with the expression cassette whereby the cell expresses the encoded Idol. In various embodiments, such expression can be constitutive, inducible, or tissue-specific using constitutive, inducible, or tissue-specific promoters.

Methods of expressing heterologous proteins in cells are well known to those of skill in the art (see, e.g., Sambrook et al., Molecular Cloning: A Laboratory Manual, Vols. 1-3, Cold Spring Harbor Laboratory Press, 2 ed., 1989, or F. Ausubel et al., Current Protocols in Molecular Biology (Green Publishing and Wiley-Interscience: New York, 1987) and periodic updates).

Idol knockouts.

In certain embodiments, animals comprising a disruption of one or both alleles of an Idol gene (Idol "knockouts") are provided. The knockout animals of this invention are useful as systems in which to screen for various agents (e.g. drugs) that modulate Idol expression and/or activity and thereby modulatge LDL receptor degredaton and/or LDL uptake.

The Idol knockouts utilize nucleic acid sequences (transgenes) that are capable of inactivating endogenous Idol genes. Such transgenes preferably contain a nucleic acid sequence (e.g., a DNA sequence) that is identical to some portion of the endogenous Idol gene that is to be disrupted. Preferred transgenes of this invention also contain an insertion, deletion, or substitution of one or more nucleotides; a frameshift mutation; and/or a stop codon as compared with undisrupted alleles of the same Idol gene naturally-occurring in the species.

Homologous recombination of the transgene with a Idol allele disrupts the expression of that allele. Such a disruption can be by a number of mechanisms including, but not limited to, interference in initiation of transcription and/or translation, by premature termination of transcription and/or translation, and/or by production of a non-functional Idol protein.

In one illustrative embodiment, such transgenes are derived by deleting nucleotides from the nucleic acid sequence encoding the functional Idol gene. Although the resultant mutated nucleic acid sequence is incapable of being transcribed and/or translated into a functional Idol gene product, such transgenes will have sufficient sequence homology with an endogenous Idol allele of a selected non-human animal such that the transgene is capable of homologous recombination with the endogenous Idol allele.

In one embodiment, transgenes are produced by ligation of an expression cassette encoding a selectable marker into the nucleic acid sequence encoding the Idol gene products and/or into the nucleic acid sequence regulating transcription of the Idol gene product. The cassette is typically inserted in a location such that it replaces or disrupts regions of the encoded protein required for protein functionality. The cassette is also typically inserted in a location such that splicing out of the cassette introduces a frameshift mutation resulting in non-functional reversions. In one embodiment, the expression cassette comprises one or more selectable marker(s), such as, e.g., β-galactosidase and/or neomycin phosphotransferase II.

Such transgenes are preferably designed for replacement of one or more exons of the endogenous Idol gene. Although insertional transgenes may also be used, replacement transgenes are preferred because they significantly reduce the likelihood of secondary recombination and reversion to the wild-type Idol gene.

The Idol knockouts of this invention are useful themselves as models systems for a number of pathologies or can be crossed with animals exhibiting particular phenotypic traits to produce useful animal models.

In certain embodiments, homologous recombination is used to control the site of integration of a specific DNA sequence (transgene) into the naturally present Idol sequence of an animal cell and thereby disrupt that gene and prevent normal its normal expression (see, e.g., Watson (1977) In: *Molecular Biology of the Gene*, 3rd Ed., W.A. Benjamin, Inc., Menlo Park, Calif.).

Typically, this is accomplished using, for example, a positive/negative selection (PNS) (Thomas and Cappechi (1987) *Cell* 51: 503-512). This method involves the use of two selectable markers: one a positive selection marker such as the bacterial gene for neomycin resistance (neo); the other a negative selection marker such as the herpes virus thymidine kinase (HSV-tk) gene. Neo confers resistance to the drug G-418, while HSV-tk renders cells sensitive to the nucleoside analog gangcyclovir (GANC) or 1-(2-deoxy-2-fluoro-b-d-arabinofuranosyl)-5-iodouraci2l (FIAU). The DNA encoding the positive selection marker in the transgene (e.g., neo) is generally linked to an expression regulation sequence that allows for its independent transcription in the target cells (e.g., embryonic stem (ES) cells). It is flanked by first and second sequence portions of at least a part of the Idol gene.

These first and second sequence portions target the transgene to a specific allele. A second independent expression unit capable of producing the expression product for a negative selection marker, e.g., for HSV-tk is positioned adjacent to or in close proximity to the distal end of the first or second portions of the first DNA sequence. Upon transfection, some of the ES cells incorporate the transgene by random integration, others by homologous recombination between the endogenous allele and sequences in the transgene. As a result, one copy of the targeted allele is disrupted by homologous recombination with the-transgene with simultaneous loss of the sequence encoding herpes HSV-tk gene. Random integrants, which occur via the ends of the transgene, contain herpes HSV-tk and remain sensitive to GANC or FIAU. Therefore, selection, either sequentially or simultaneously with G418 and GANC enriches for transfected ES cells containing the transgene integrated into the genome by homologous recombination.

Other strategies that select for homologous recombination events but do not use PNS may also be used.

It is possible that in some circumstances it will not be desirable to have an expressed antibiotic resistance gene incorporated into the knockout animal. Therefore, in certain embodiments, one or more genetic elements are included in the knockout construct that permit the antibiotic resistance gene to be excised once the construct has undergone homologous recombination with the Idol gene.

The methods described herein and illustrated in Example 2 are capable of mutating both alleles of the cell's Idol gene; however, since the frequency of such dual mutational events is the square of the frequency of a single mutational event, cells having mutations in both of their Idol alleles will be only a very small proportion of the total population of mutated cells. It is possible to readily identify (for example through the use of Southern hybridization or other methods) whether the mutational events are single-allele or dual-allele events. Animals having a mutational event in a single allele may be cross-bred to produce homozygous animals (having the disruption in both alleles) if the disruption becomes incorporated in the germ line.

In one embodiment, the nucleic acid molecule(s) that are to be introduced into the recipient cell contain a region of homology with a region of the Idol gene. In a preferred embodiment, the nucleic acid molecule will contain two regions having homology with the cell's Idol gene. These "regions of homology" will preferably flank the precise sequence whose incorporation into the Idol gene is desired.

The nucleic acid molecule(s) may be single stranded, but are preferably double stranded. The molecule(s) may be introduced to the cell as DNA molecules, as one or more RNA molecules which may be converted to DNA by reverse transcriptase or by other means.

To produce the knockout animal, cells are transformed with the construct (e.g., transgene) described above. As used herein, the term "transformed" is defined as introduction of exogenous DNA into the target cell by any means known to the skilled artisan. These methods of introduction can include, without limitation, transfection, microinjection, infection (with, for example, retroviral-based vectors), electroporation and microballistics. The term "transformed," unless otherwise indicated, is not intended herein to indicate alterations in cell behavior and growth patterns accompanying immortalization, density-independent growth, malignant transformation or similar acquired states in culture.

To create animals having a particular gene inactivated in all cells, it is preferable to introduce a knockout construct into the germ cells (sperm or eggs, i.e., the "germ line") of the desired species. Genes or other DNA sequences can be introduced into the pronuclei of fertilized eggs by microinjection or other methods. Following pronuclear fusion, the developing embryo may carry the introduced gene in all its somatic and germ cells since the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is preferred that a cultured cell containing the desired knockout construct be capable of generating a whole animal. This is generally accomplished by placing the cell into a developing embryo environment of some sort.

Cells capable of giving rise to at least several differentiated cell types are hereinafter termed "pluripotent" cells. Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking a functional Idol gene. That is, cultured ES cells can be transformed with a knockout construct, as described herein, and cells selected in which the Idol gene is inactivated through insertion of the construct within the Idol gene.

The transgenic non-human animals of the invention are produced by introducing transgenes into the germline of the non-human animal. Embryonic target cells at various developmental stages can be used to introduce transgenes. Different methods are used depending on the stage of development of the embryonic target cell.

Microinjection is one illustrative method for transformation of a zygote. In the mouse, the male pronucleus reaches the size of approximately 20 micrometers in diameter which allows reproducible injection of 1-2 pl of DNA solution. The use of zygotes as a target for gene transfer has a major advantage in that in most cases the injected DNA will be incorporated into the host gene before the first cleavage (Brinster et al. (1985) *Proc. Natl. Acad. Sci. USA* 82, 4438-4442). As a consequence, all cells of the transgenic non-human animal will carry the incorporated transgene. This will, in general, also be reflected in the efficient transmission of the transgene to offspring of the founder since 50% of the germ cells will harbor the transgene.

The gene sequence being introduced need not be incorporated into any kind of self-replicating plasmid or virus (Jaenisch, (1988) *Science*, 240: 1468-1474). Indeed, the presence of vector DNA has been found, in many cases, to be undesirable (Hammer et al. (1987) *Science* 235: 53; Chada et al. (1986) *Nature* 319: 685; Kollias et al., (1986) *Cell* 46: 89; Shani, (1986) *Molec, Cell, Biol.* 6: 2624 (1986); Chada, et al. (1985) *Nature*, 314: 377; Townes et al. (1985) *EMBO J.* 4: 1715).

Once the DNA molecule has been injected into the fertilized egg cell, the cell is implanted into the uterus of a recipient female, and allowed to develop into an animal. Since all of the animal's cells are derived from the implanted fertilized egg, all of the cells of the resulting animal (including the germ line cells) contain the introduced gene sequence. If, as occurs in about 30% of events, the first cellular division occurs before the introduced gene sequence has integrated into the cell's genome, the resulting animal will be a chimeric animal.

By breeding and inbreeding such animals, it is possible to routinely produce heterozygous and homozygous transgenic animals. Despite any unpredictability in the formation of such transgenic animals, the animals have generally been found to be stable, and to be capable of producing offspring that retain and express the introduced gene sequence.

The success rate for producing transgenic animals is greatest in mice. Approximately 25% of fertilized mouse eggs into which DNA has been injected, and which have been implanted in a female, will become transgenic mice. A number of other transgenic animals have also been produced. These include rabbits, sheep, cattle, and pigs (Jaenisch (1988) *Science* 240: 1468-1474; Hammer et al., (1986) *J. Animal. Sci,* 63: 269; Hammer et al. (1985) *Nature* 315: 680; Wagner et al., (1984) *Theriogenology* 21: 29).

Retroviral infection can also be used to introduce a transgene into a non-human animal. The developing non-human embryo can be cultured in vitro to the blastocyst stage. During this time, the blastomeres can be targets for retroviral infection (Jaenich (1976) *Proc. Natl. Acad. Sci USA* 73: 1260-1264). Efficient infection of the blastomeres is obtained by enzymatic treatment to remove the zona pellucida (Hogan, et al. (1986) In *Manipulating the Mouse Embryo*, Cold Spring Harbor Laboratory Press, Cold Spring Harbor, N.Y.). The viral vector system used to introduce the transgene is typically a replication-defective retrovirus carrying the transgene (Jahner, et al. (1985) *Proc. Natl. Acad. Sci. USA* 82, 6927-6931; Van der Putten, et al. (1985) *Proc. Natl. Acad. Sci., USA,* 82, 6148-6152). Transfection is easily and efficiently obtained by culturing the blastomeres on a monolayer of virus-producing cells (Van der Putten, supra; Stewart et al. (1987) *EMBO J.,* 6: 383-388). Alternatively, infection can be performed at a later stage. Virus or virus-producing cells can be injected into the blastocoele (Jahner et al. (1982) *Nature,* 298: 623-628). Most of the founders will be mosaic for the transgene since incorporation occurs only in a subset of the cells, which formed the transgenic non-human animal. Further, the founder may contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner et al. (1982) supra).

A third and preferred target cell for transgene introduction is the embryonic stem cell (ES). ES cells are obtained from pre-implantation embryos cultured in vitro and fused with embryos (Evans, et al. (1981) Nature, 292: 154-156; Bradley, et al. (1984) *Nature,* 309: 255-258; Gossler, et al. (1986) *Proc. Natl. Acad. Sci., USA,* 83:, 9065-9069; and Robertson, et al. (1986) *Nature,* 322: 445-448). Transgenes can be efficiently introduced into the ES cells a number of means well known to those of skill in the art. Such transformed ES cells can thereafter be combined with blastocysts from a non-human animal. The ES cells thereafter colonize the embryo and contribute to the germ line of the resulting chimeric animal (for a review see Jaenisch (1988) *Science,* 240: 1468-1474).

The DNA molecule containing the desired gene sequence may be introduced into the pluripotent cell by any method which will permit the introduced molecule to undergo recombination at its regions of homology. Transgenes can be efficiently introduced into the ES cells by DNA transfection or by retrovirus-mediated transduction.

In a particular embodiment, the DNA is introduced by electroporation (Toneguzzo et al., (1988) *Nucleic Acids Res.,* 16: 5515-5532; Quillet et al. (1988) *J. Immunol.,* 141: 17-20; Machy et al. (1988) *Proc. Natl. Acad. Sci., USA,* 85: 8027-8031). After permitting the introduction of the DNA molecule(s), the cells are cultured under conventional conditions, as are known in the art.

In order to facilitate the recovery of those cells that have received the DNA molecule containing the desired gene sequence, it is preferable to introduce the DNA containing the desired gene sequence in combination with a second gene sequence that would contain a detectable marker gene sequence. Where it is only desired to introduce a disruption into a gene, the DNA sequence containing the detectable marker sequence may itself comprise the disruption. For the purposes of the present invention, any gene sequence whose presence in a cell permits one to recognize and clonally isolate the cell may be employed as a detectable (selectable) marker gene sequence.

In one embodiment, the presence of the detectable (selectable) marker sequence in a recipient cell is recognized by hybridization, by detection of radiolabelled nucleotides, or by other assays of detection which do not require the expression of the detectable marker sequence. In one embodiment, such sequences are detected using polymerase chain reaction (PCR) or other DNA amplification techniques to specifically amplify the DNA marker sequence (Mullis et al., (1986) Cold Spring Harbor *Symp. Quant. Biol.* 51: 263-273; Erlich et al. EP 50,424; EP 84,796, EP 258,017 and EP 237,362; Mullis EP 201,184; Mullis et al., U.S. Pat. No. 4,683,202; Erlich U.S. Pat. No. 4,582,788; and Saiki et al. U.S. Pat. No. 4,683,194).

Most preferably, however, the detectable marker gene sequence will be expressed in the recipient cell and will result in a selectable phenotype. Selectable markers are well known to those of skill in the art. Some examples include the hprt gene (Littlefield (1964) *Science* 145: 709-710), the thymidine kinase gene of herpes simplex virus (Giphart-Gassier et al. (1989) *Mutat, Res.,* 214: 223-232), the nDtII gene (Thomas et al. (1987) *Cell,* 51: 503-512; Mansour et al. (1988) Nature 336: 348-352), or other genes which confer resistance to amino acid or nucleoside analogues, or antibiotics, etc.

Thus, for example, cells that express an active HPRT enzyme are unable to grow in the presence of certain nucleoside analogues (such as 6-thioguanine, 8-azapurine, etc.), but are able to grow in media supplemented with HAT (hypoxanthine, aminopterin, and thymidine). Conversely, cells which fail to express an active HPRT enzyme are unable to grow in media containing HATG, but are resistant to analogues such as 6-thioguanine, etc. (Littlefield (1964) *Science,* 145: 709-710). Cells expressing active thymidine kinase are able to grow in media containing HAT, but are unable to grow in media containing nucleoside analogues such as bromo-deoxyuridine (Giphart-Gassler et al. (1989) Mutat. Res. 214: 223-232). Cells containing an active HSV-tk gene are incapable of growing in the presence of gangcylovir or similar agents.

The detectable marker gene may also be any gene that can compensate for a recognizable cellular deficiency. Thus, for example, the gene for HPRT could be used as the detectable marker gene sequence when employing cells lacking HPRT activity. This agent is an example of agents may be used to select mutant cells, or to "negatively select" for cells which have regained normal function.

In preferred embodiments, the chimeric or transgenic animal cells of the present invention are prepared by introducing one or more DNA molecules into a precursor pluripotent cell, most preferably an ES cell, or equivalent (Robertson (1989) pages 39-44 In: Current communications in Molecular Biology, Capecchi, M. R. (ed.), Cold Spring Harbor Press, Cold Spring Harbor, N.Y. The term "precursor" is intended to denote only that the pluripotent cell is a precursor to the desired ("transfected") pluripotent cell which is prepared in accordance with the teachings of the present invention. The pluripotent (precursor or transfected) cell may be cultured in vivo, in a manner known in the art (Evans et al., (1981) Nature 292: 154-156) to form a chimeric or transgenic animal. The transfected cell, and the cells of the embryo that it forms upon introduction into the uterus of a female are herein referred to respectively, as "embryonic stage" ancestors of the cells and animals of the present invention.

Any ES cell may be used in accordance with the methods described herein. In certain embodiments, it is, however, preferred to use primary isolates of ES cells. Such isolates may be obtained directly from embryos such as the CCE cell line disclosed by Robertson, E. J., In: *Current Communications in Molecular Biology*, Capecchi, M. R. (ed.), Cold Spring Harbor Press, Cold Spring Harbor, N.Y. (1989), pp. 39-44), or from the clonal isolation of ES cells from the CCE cell line (Schwartzberg et al. (1989) *Science* 212: 799-803). Such clonal isolation may be accomplished according to the method of Robertson (1987) In: Teratocarcinomas and Embryonic Stem Cells: A Practical Approach, E. J. Robertson, Ed., IRL Press, Oxford. The purpose of such clonal propagation is to obtain ES cells that have a greater efficiency for differentiating into an animal. Clonally selected ES cells are approximately 10-fold more effective in producing transgenic animals than the progenitor cell line CCE. An example of ES cell lines which have been clonally derived from embryos are the ES cell lines, AB1 (hprt+) or AB2.1 (hprt-).

The ES cells are preferably cultured on stromal cells (such as STO cells (especially SNL76/7 STO cells) and/or primary embryonic G418 R fibroblast cells) as described by Robertson, supra. Methods for the production and analysis of chimeric mice are well known to those of skill in the art (see, e.g., Bradley (1987) pages 113-151 In: *Teratocarcinomas and Embryonic Stem Cells; A Practical Approach*, E. J. Robertson, ed., IRL Press, Oxford). The stromal (and/or fibroblast) cells serve to eliminate the clonal overgrowth of abnormal ES cells. Most preferably, the cells are cultured in the presence of leukocyte inhibitory factor ("lif") (Gough et al. (1989) *Reprod. Fertil.*, 1: 281-288; Yamamori et al. (1989) *Science*, 246: 1412-1416). Since the gene encoding lif has been cloned (Gough, et al. supra.), it is especially preferred to transform stromal cells with this gene, by means known in the art, and to then culture the ES cells on transformed stromal cells that secrete lif into the culture medium.

ES cell lines may be derived or isolated from any species (for example, chicken, fish, etc.), although cells derived or isolated from mammals such as rodents, rabbits, sheep, goats, pigs, cattle, primates and humans are preferred. Cells derived from rodents (i.e., mouse, rat, hamster, etc.) are particularly preferred.

In fact, ES cell lines have been derived for mice and pigs as well as other animals (see, e.g., Robertson, Embryo-Derived Stem Cell Lines. In: *Teratocarcinomas and Embryonic Stem Cells*: A Practical Approach (E. J. Robertson, ed.), IRL Press, Oxford (1987); PCT Publication No. WO/90/03432; PCT Publication No. 94/26884. Generally these cells lines must be propagated in a medium containing a differentiation-inhibiting factor (DIF) to prevent spontaneous differentiation and loss of mitotic capability. Leukemia Inhibitory Factor (LIF) is particularly useful as a DIF. Other DIFs useful for prevention of ES cell differentiation include, without limitation, Oncostatin M (Gearing and Bruce (1992) *The New Biologist* 4: 61-65), interleukin 6 (IL-6) with soluble IL-6 receptor (sIL-6R) (Taga et al. (1989) *Cell* 58: 573-581), and ciliary neurotropic factor (CNTF) (Conover et al. (1993) *Development* 19: 559-565). Other known cytokines may also function as appropriate DIFs, alone or in combination with other DIFs.

As a useful advance in maintenance of ES cells in an undifferentiated state, a novel variant of LIF (T-LIF) has been identified (see U.S. Pat. No. 5,849,991). In contrast to the previously identified forms of LIF which are extracellular, T-LIF is intracellularly localized. The transcript was cloned from murine ES cells using the RACE technique (Frohman et al. (1988) *Proc. Natl. Acad. Sci., USA*, 85: 8998-9002) and subjected to sequence analysis. Analysis of the obtained nucleic acid sequence and deduced amino acid sequence indicates that T-LIF is a truncated form of the LIF sequence previously reported in the literature. Expression of the T-LIF nucleic acid in an appropriate host cell yields a 17 kD protein that is unglycosylated. This protein is useful for inhibiting differentiation of murine ES cells in culture.

Production of the knockout animals of this invention is not dependent on the availability of ES cells. In various embodiments, knockout animals of this invention can be produced using methods of somatic cell nuclear transfer. In preferred embodiments using such an approach, a somatic cell is obtained from the species in which the Idol gene is to be knocked out. The cell is transfected with a construct that introduces a disruption in the Idol gene (e.g., via heterologous recombination) as described herein. Cells harboring a knocked-out Idol are selected as described herein. The nucleus of such cells harboring the knockout is then placed in an unfertilized enucleated egg (e.g., eggs from which the natural nuclei have been removed by microsurgery). Once the transfer is complete, the recipient eggs contain a complete set of genes, just as they would if they had been fertilized by sperm. The eggs are then cultured for a period before being implanted into a host mammal (of the same species that provided the egg) where they are carried to term, culminating in the birth of a transgenic animal comprising a nucleic acid construct containing one or more disrupted Idol genes The production of viable cloned mammals following nuclear transfer of cultured somatic cells has been reported for a wide variety of species including, but not limited to frogs (McKinnell (1962) *J. Hered.* 53, 199-207), calves (Kato et al. (1998) *Science* 262: 2095-2098), sheep (Campbell et al. (1996) *Nature* 380: 64-66), mice (Wakayama and Yanagimachi (1999) *Nat. Genet.* 22: 127-128), goats (Baguisi et al. (1999) *Nat. Biotechnol.* 17: 456-461), monkeys (Meng et al. (1997) *Biol. Reprod.* 57: 454-459), and pigs (Bishop et al. (2000) *Nature Biotechnology* 18: 1055-1059). Nuclear transfer methods have also been used to produce clones of transgenic animals. Thus, for example, the production of transgenic goats carrying the human antithrombin III gene by somatic cell nuclear transfer has been reported (Baguisi et al. (1999) *Nature Biotechnology* 17: 456-461).

Using methods of nuclear transfer as describe in these and other references, cell nuclei derived from differentiated fetal or adult, mammalian cells are transplanted into enucleated mammalian oocytes of the same species as the donor nuclei. The nuclei are reprogrammed to direct the development of cloned embryos, which can then be transferred into recipient females to produce fetuses and offspring, or used to produce cultured inner cell mass (CICM) cells. The cloned embryos can also be combined with fertilized embryos to produce chimeric embryos, fetuses and/or offspring.

Somatic cell nuclear transfer also allows simplification of transgenic procedures by working with a differentiated cell source that can be clonally propagated. This eliminates the need to maintain the cells in an undifferentiated state, thus, genetic modifications, both random integration and gene targeting, are more easily accomplished. Also by combining nuclear transfer with the ability to modify and select for these cells in vitro, this procedure is more efficient than previous transgenic embryo techniques.

Nuclear transfer techniques or nuclear transplantation techniques are known in the literature. See, in particular, Campbell et al. (1995) *Theriogenology*, 43:181; Collas et al. (1994) *Mol. Report Dev.*, 38:264-267; Keefer et al. (1994) *Biol. Reprod.*, 50:935-939; Sims et al. (1993) *Proc. Natl. Acad. Sci., USA*, 90:6143-6147; WO 94/26884; WO 94/24274, WO 90/03432, U.S. Pat. Nos. 5,945,577, 4,944,384, 5,057,420 and the like.

Having shown that disruption of the Idol gene produces Idol-deficient animals that are viable, one of skill will recognize that there are a wide number of animals including natural and transgenic animals that have other desirable phenotypes and that can be used to practice the invention. Preferred animals are mammals including, but not limited to, rodents (e.g, murines), equines, bovines, porcines, lagomorphs, felines, canines, caprines, ovines, non-human primates, and the like.

Zygotes or ES cells from the Idol knockouts of this invention can be used as embryonic target cells for introduction of other heterologous genes or knockout constructs. Alternatively somatic cells can be used as targets for the introduction of various heterologous expression cassettes or knockout constructs.

In other embodiments, the knockout animals of this invention can be can be cross-bred with other animals exhibiting various natural or induced pathologies. In various embodiments, the knockout animals of this invention are crossed with animals having one or more knockouts other than the Idol knockout.

In certain preferred embodiments, a transgenic non-human animal is bred that that includes a deficiency in Idol expression (e.g., a heterozygous or homozygous Idol knockout) and a deficiency in a second recombinantly disrupted gene.

V. Kits

In certain embodiments kits are provided for the treatment methods and/or screening methods described herein (e.g., to inhibit LDL receptor degradation and/or promote LDL uptake in a mammal, and/or mitigate one or more symptoms of hypercholesterolemia, or to screen for agents that inhibit Mylip expression and/or activity). "Therapeutic" kits typically include a container containing one or more Mylip inhibitors (e.g., siRNA, shRNA, etc.). Such kits can, optionally include instruments for formulating or administering the agent(s). Screening kits can include any of the reagents for performing the screening assays described herein. In certain embodiments, the kits comprise a construct containing a reporter gene whose expression is regulated by Mylip or cell(s) comprising such a construct. In addition the kits typically include instructional materials disclosing means of use of the inhibitors to slow aging, or instructional materials describing how to screen for agents that slow aging. The kits can additionally include buffers and other reagents routinely used for the practice of a particular method. Such kits and appropriate contents are well known to those of skill in the art.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

LXR Regulates Cholesterol Uptake Through Mylip-Dependent Ubiquitination of the LDL Receptor The LDL receptor (LDLR) is a critical determinant of plasma cholesterol levels. Here we show that the sterol-responsive nuclear receptor LXR regulates LDLR-mediated lipoprotein uptake independent of SREBPs. Ligand activation of LXR redistributes the LDLR from the plasma membrane to an intracellular compartment and promotes its degradation. This effect is accomplished through the transcriptional induction of myosin light chain interacting protein (Mylip), an E3 ubiquitin ligase. Enzymatically active Mylip triggers ubiquitination of the LDLR on its cytoplasmic domain, thereby targeting it for degradation. Mylip knockdown inhibits LDLR degradation and promotes LDL uptake. Conversely, expression of Mylip in mouse liver dramatically reduces LDLR protein and elevates plasma LDL levels. The LXR-Mylip-LDLR axis defines a previously unrecognized pathway for sterol regulation of LDL metabolism and an enzyme target for the treatment of hypercholesterolemia.

Introduction

The LDL receptor (LDLR) is central to the maintenance of plasma cholesterol levels (Russell et al. (1984) Cell 37: 577). Mutations in this receptor are the leading cause of autosomal dominant hypercholesterolemia (ADH), characterized by defective hepatic LDL uptake, elevated plasma cholesterol levels, and increased risk of cardiovascular disease (Tolleshaug et al. (1983) Cell 32: 941; Brown and Goldstein (1986) *Science* 232: 34). In line with its pivotal role in cholesterol homeostasis, expression of the LDLR is tightly regulated. Transcription of the LDLR gene is coupled to cellular cholesterol levels through the action of the sterol response element binding protein (SREBP) transcription factors (Yokoyama et al. (1993) *Cell* 75: 187; Hua et al. (1993) *Proc. Natl. Acad. Sci., USA*, 90: 11603). Enhanced processing of SREBPs to their mature forms when cellular sterol levels decline leads to increased cholesterol biosynthesis and enhanced LDLR transcription (Goldstein et al. (2006) *Cell* 124: 35). Posttranscriptional regulation of LDLR expression is also a major determinant of lipoprotein metabolism. Genetic studies have identified mutations in the genes encoding the LDLR adaptor protein 1 (LDLRAP1/ARH) (Garcia et al. (2001) *Science* 292: 1394; Cohen et al. (2003) *Curr Opin Lipidol* 14: 121) and the SREBP target gene proprotein convertase subtilisin/kexin 9 (PCSK9) that result in altered stability, endocytosis, or trafficking of the LDLR (Abifadel et al. (2003) *Nat Genet* 34: 154; Cohen et al. (2005) *Nat Genet* 37: 161; Seidah et al. (2003) *Proc. Natl. Acad. Sci., USA*, 100: 928; Maxwell et al. *Proc. Natl. Acad. Sci., USA*, 101: 7100; Park et al. (2004) *J Biol Chem* 279: 50630).

The Liver X Receptors (LXRs) provide a complementary pathway for the transcriptional control of cholesterol metabolism. LXRα (NR1H3) and LXRβ (NR1H2) are sterol-dependent nuclear receptors activated in response to cellular cholesterol excess (Zelcer and Tontonoz (2006) *J Clin Invest* 116: 607). LXRs target genes such as ABCA1 and ABCG1 promote the efflux of cellular cholesterol and help to maintain whole-body sterol homeostasis (Repa et al. (2000) *Science* 289: 1524; Kennedy et al. (2005) *Cell Metab* 1: 121). Mice lacking LXRs develop marked accumulation of sterols in their tissues and accelerated atherosclerosis, whereas synthetic LXR agonists promote reverse cholesterol transport and protect against atherosclerosis (Peet et al. (1998) *Cell* 93: 693; Tangirala et al. (2002) *Proc. Natl. Acad. Sci., USA*, 99: 11896; Joseph et al. (2002) *Proc. Natl. Acad. Sci., USA*, 99: 7604). The coordinated regulation of intracellular sterol levels by the LXR and SREBP signaling pathways led us to hypothesize that LXRs may act to limit cholesterol uptake in addition to promoting cholesterol efflux.

Figure 1B:
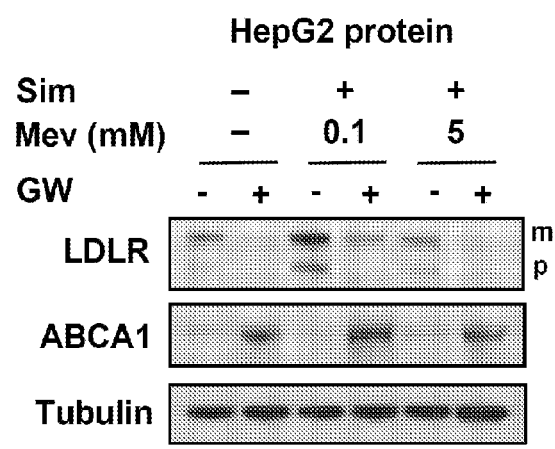
Figure 1C:
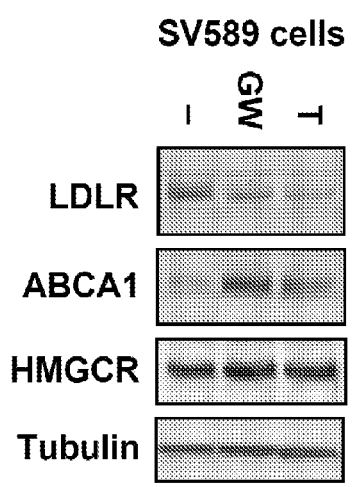
Figure 1D:
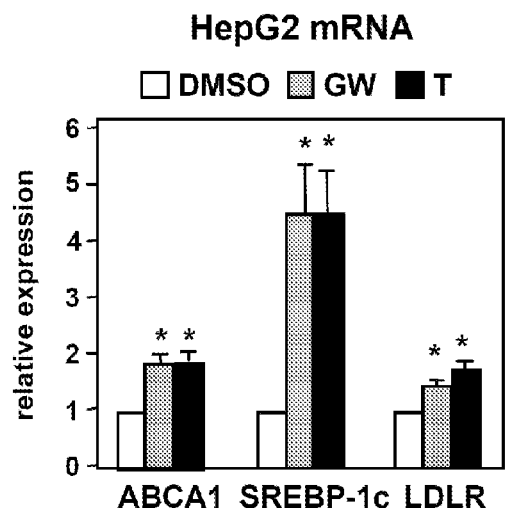
Figure 5:
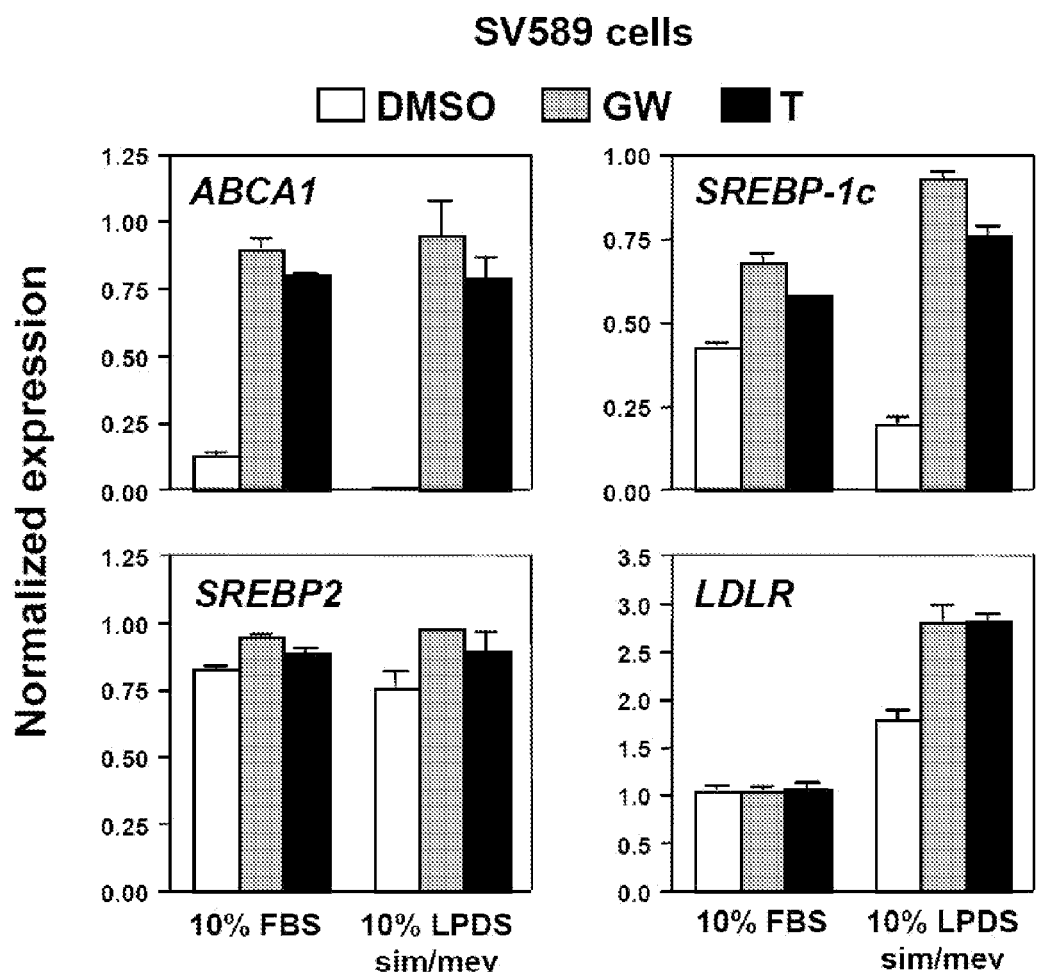
FIG. 5 shows the effect of LXR activation on LDLR mRNA expression in SV589 cells. Gene expression in SV589 cells cultured in 10% FBS or sterol depletion medium was determined 24 h after treatment with LXR agonists GW or T (1 μM).

We initially tested the ability of LXRs to modulate LDL uptake in cultured cells. Treatment of HepG2 cells with either of two structurally-unrelated synthetic LXR ligands (GW3695 or T1317) decreased binding and uptake of bodipy labeled-LDL (FIG. 1A). As the LDLR is the major route of LDL uptake, we tested the effects of LXR agonists on LDLR expression. Activation of LXR decreased LDLR protein expression in HepG2 cells independent of cellular sterol levels (FIG. 1B). The LDLR receptor runs as a doublet on western blots, with the ratio of the upper and lower bands varying by cell type. The upper band (m) is the mature glycosylated form found in the plasma membrane, while the lower band corresponds to an immature precursor (p). The effect of LXR was most prominent on the mature LDLR. Remarkably, this reduction occurred despite a slight increase in LDLR transcript, likely secondary to induction of SREBP-1c expression by LXR (FIG. 1C). The ability of LXRs to decrease LDLR proteins levels was also apparent in human SV589 fibroblasts that have been used extensively to delineate SREBP processing (FIG. 1D) (Adams et al. (2004) *J Biol Chem* 279: 52772) Reduction in LDLR protein by LXR ligands in SV589 cells was not paralleled by changes in HMGCoA reductase expression (FIG. 1D) and could not be attributed to a decrease in LDLR mRNA (FIG. 5A).

Figure 1E:
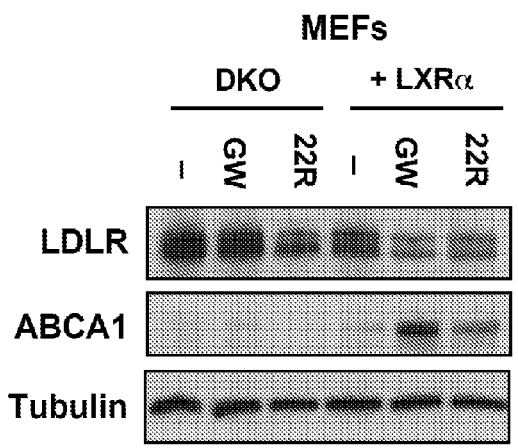
Figure 1F:
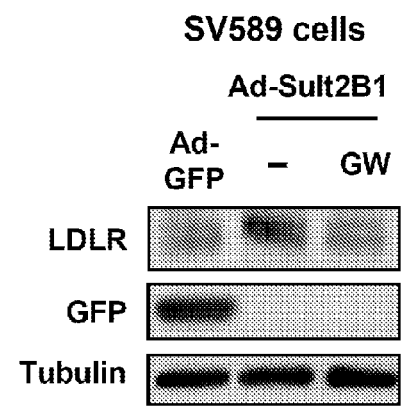
Figure 1G:
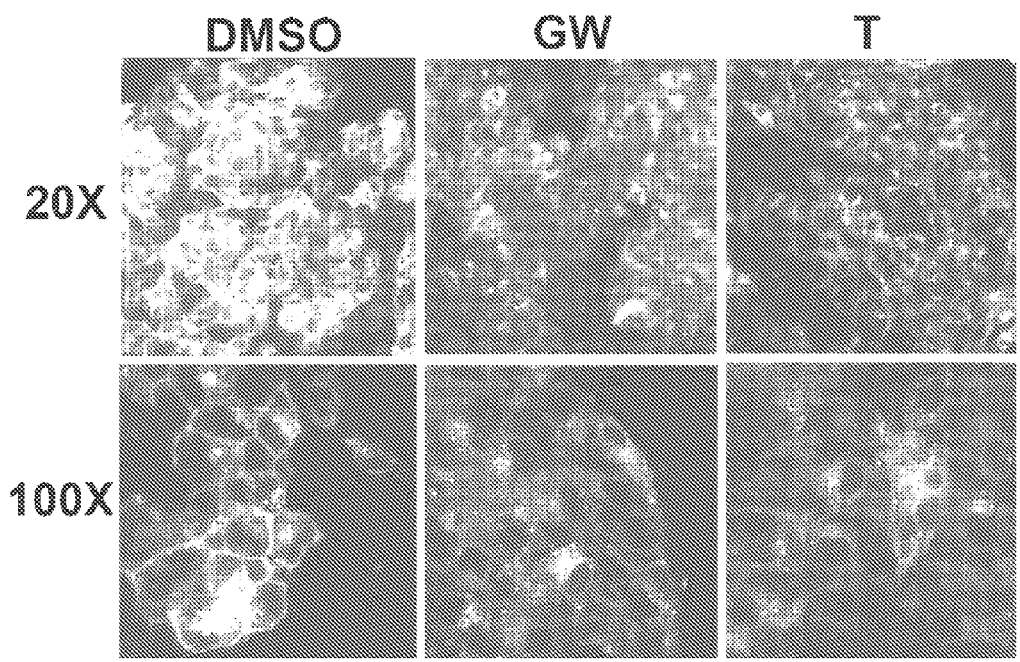

To determine whether the effect of the synthetic ligands on LDLR was LXR-dependent, we used immortalized Lxrαβ $^{(-/-)}$ mouse embryonic fibroblasts (MEFs) stably expressing LXRα or vector control. Oxysterol LXR ligands block SREBP processing in addition to activating LXR, and therefore 22(R)-hydroxycholesterol decreased LDLR protein in the absence or presence of LXRs (FIG. 1E). By contrast, the synthetic ligand GW3965 decreased LDLR only in cells expressing LXRα. To investigate the link between endogenous LXR ligands and LDLR expression we utilized an adenovirus expressing oxysterol sulfotransferase (Sult2b1). Depletion of oxysterol agonists by Sult2b1 in SV589 cells led to increased LDLR protein, and this effect was reversed by synthetic ligand (FIG. 1F). To further delineate the role of LXRs in regulating LDLR expression, we tested the effect of LXR agonists on LDLR produced from a transfected vector not subject to endogenous SREBP regulation. In HepG2 cells stably expressing an LDLR-GFP fusion protein, LDLR-GFP expression was visualized primarily on the plasma membrane (FIG. 1G). Ligand activation of LXR decreased overall LDLR-GFP expression and redistributed the LDLR from the plasma membrane to intracellular compartments (FIG. 1G).

Figure 2A:
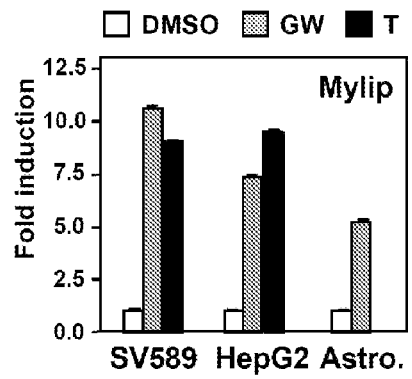
Figure 2B:
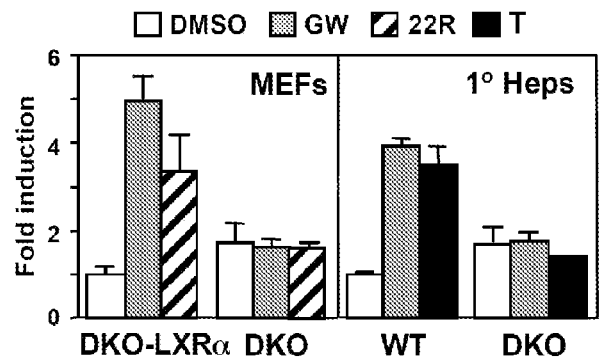
Figure 2C:
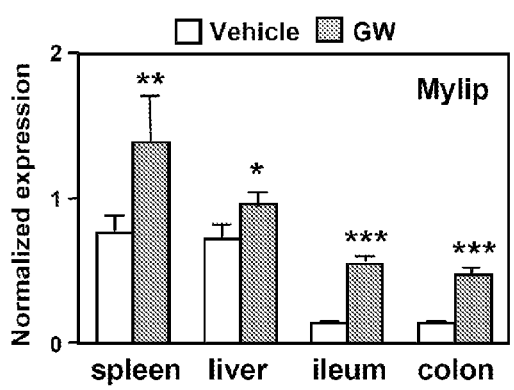

The above results indicate that LXR signaling modulates LDLR expression independent of the SREBP pathway. We reasoned that an LXR target gene must underlie this effect, possibly one that promotes degradation of the LDLR. Using transcriptional profiling we identified a potential mediator: the myosin light chain interacting protein (Mylip) (data not shown). Mylip is a member of the Ezrin/Radixin/Moesin (ERM) family of proteins that mediates interactions between proteins and membrane structures (Bretscher et al. (2992) *Nat Rev Mol Cell Biol* 3: 586). Distinguishing it from other members of this family, Mylip contains a C-terminal RING domain and acts as an E3-ubiquitin ligase (Olsson et al. (1999) *J Biol Chem* 274: 36288; Bornhauser et al. (2003) *FEBS Lett* 553: 195). LXR agonists strongly induced Mylip expression in cell lines and primary cells of human and rodent origin in an LXR-dependent manner (FIGS. 2A and 2B). Furthermore, Mylip expression was induced in vivo following administration of GW3965 to mice (FIG. 2C).

Figure 6D:
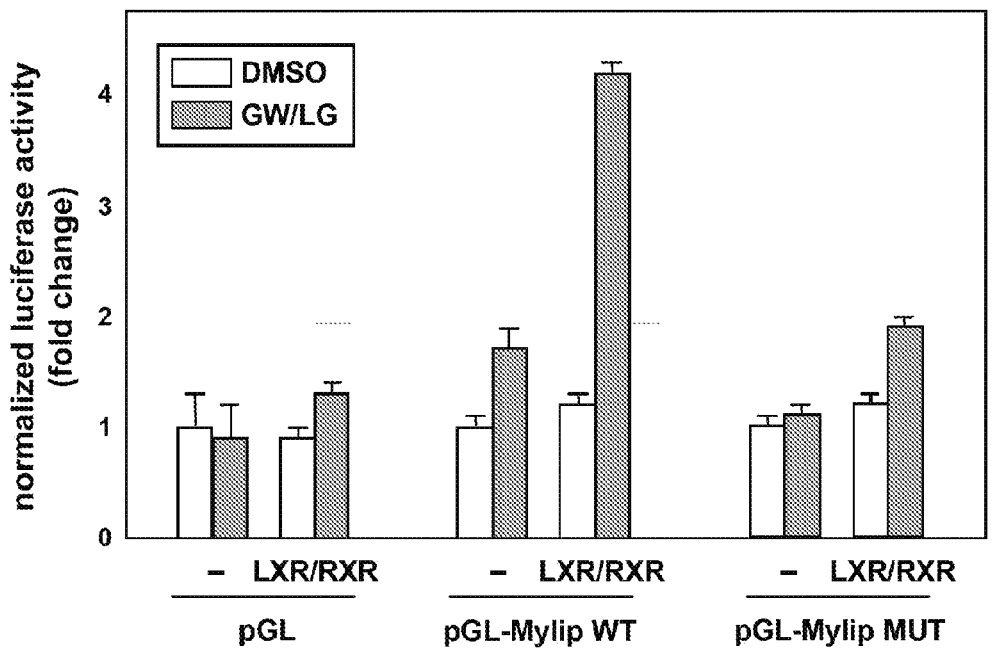

LXR regulation of Mylip was not sensitive to the ribosomal poison cycloheximide, suggesting that it is a direct transcriptional effect (FIG. 6A). It also could not be secondary to induction of SREBP-1c, because oxysterols that block SREBP processing still induced Mylip expression (FIG. 6B). LXRs activate target genes by binding to consensus elements (LXREs) in their promoters. We identified an LXRE approximately 2.5 kb upstream of the mouse Mylip translation start site (FIG. 6C) and generated a reporter construct encompassing this region. Activation by LXRa and GW3965 resulted in a ~4-fold increase in reporter activity that was largely abolished in the absence of a functional LXRE (FIG. 6D). EMSA analysis showed that LXR/RXR heterodimers bound to wild type but not mutant versions of the Mylip LXRE and that binding could be competed by an excess of unlabeled Mylip LXRE (FIG. 6E).

Figure 2D:
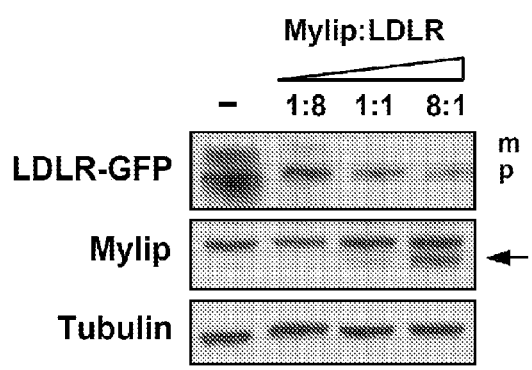
Figure 2E:
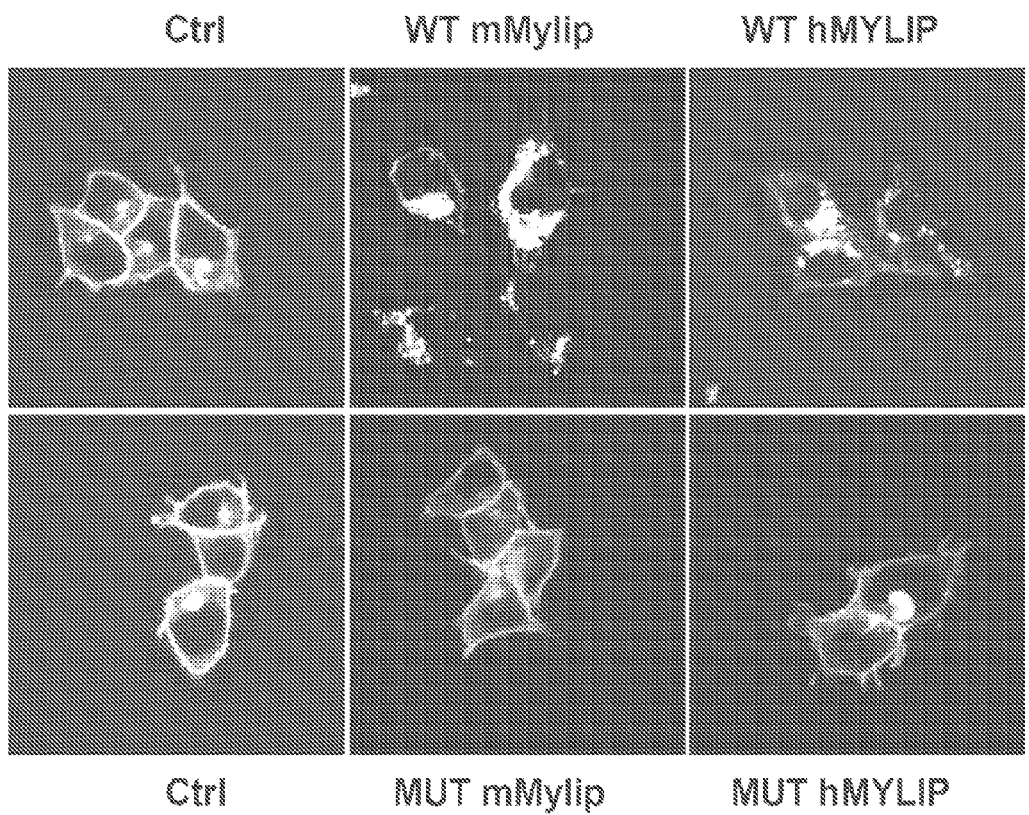
Figure 7:
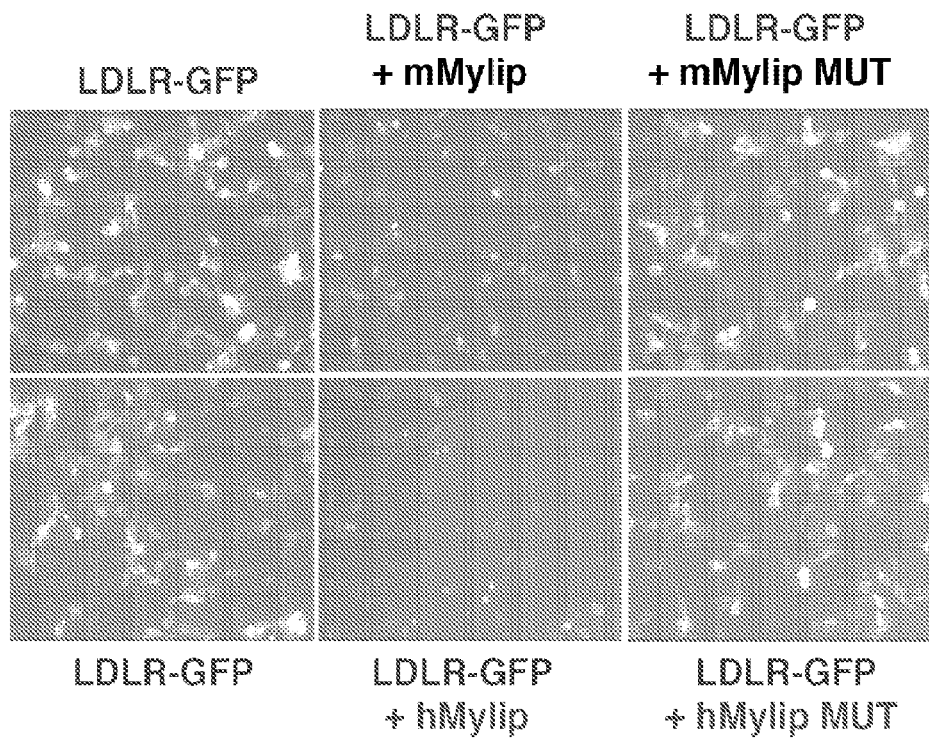
FIG. 7 shows that expression of Mylip inhibits plasma membrane expression of the LDLR. Low magnification immunofluorescene images of HEK293 cells co-transfected with LDLR-GFP and Mylip constructs

Ubiquitination plays an important role in modulating protein expression. Given that Mylip is a putative E3 ubiquitin ligase, we hypothesized that Mylip induction might underlie the ability of LXRs to inhibit LDLR expression. Employing a co-transfection system in HEK293T cells we found that both human and mouse Mylip potently reduced the expression of LDLR-GFP in a dose-dependent manner (FIG. 2D). Moreover, consistent with the effect observed with LXR agonists, Mylip expression redistributed LDLR-GFP expression from the plasma membrane to an intracellular compartment (FIG. 2E and FIG. 7). By contrast, Mylip carrying a point mutation (C387A) in the catalytic RING domain had no effect on LDLR expression or localization. Also, in line with the effects of LXR ligand (FIG. 1), the effects of Mylip were most prominent on the fully glycosylated mature LDLR form (FIGS. 2D and 2F). Notably, Mylip expression was greatly enhanced when the RING domain was mutated raising the possibility that Mylip might catalyze its own degradation.

The effect of Mylip on membrane protein expression appears to be selective for the LDLR. Levels of transfected LRP1-GFP or APP-GFP proteins, both of which contain NPXY motifs and undergo regulated endocytosis similar to the LDLR, were unaffected by Mylip expression (FIG. 2F). Mylip also did not influence expression of ABCA1-GFP, endogenous transferrin receptor (TFRC), or endogenous myosin regulatory light chain (MRLC). Importantly, regulation of LDLR receptor by Mylip was observed in multiple cell types, including primary hepatocytes (FIG. 2G), as well as HepG2 cells, macrophages, and fibroblasts (data not shown).

Figure 2H:
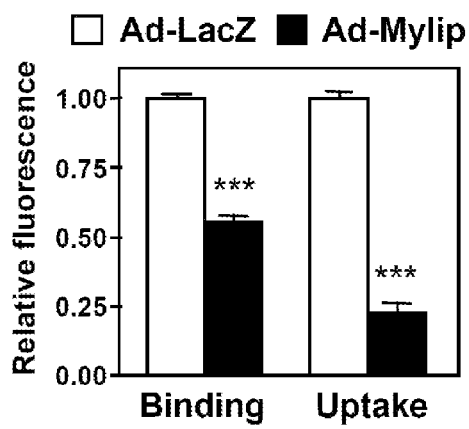
Figure 2I:
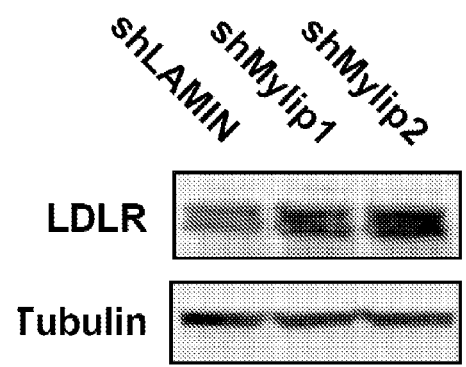
Figure 8A:
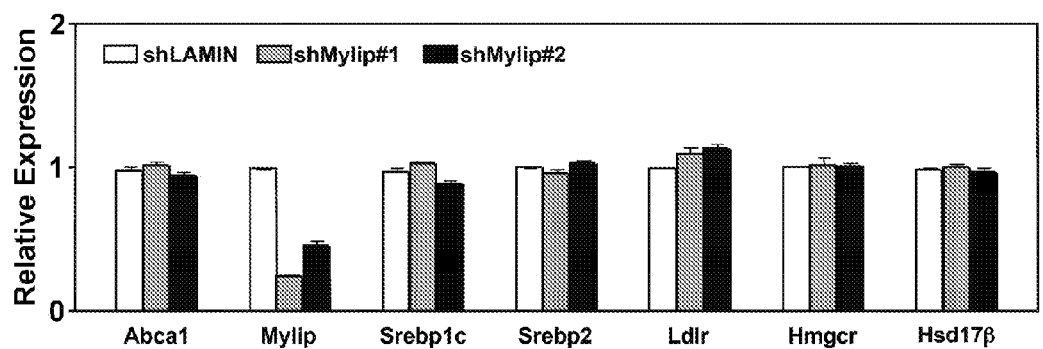
FIGS. 8A and 8B show the effect of Mylip knockdown on LDLR mRNA and protein expression in MEFs.
Figure 8B:
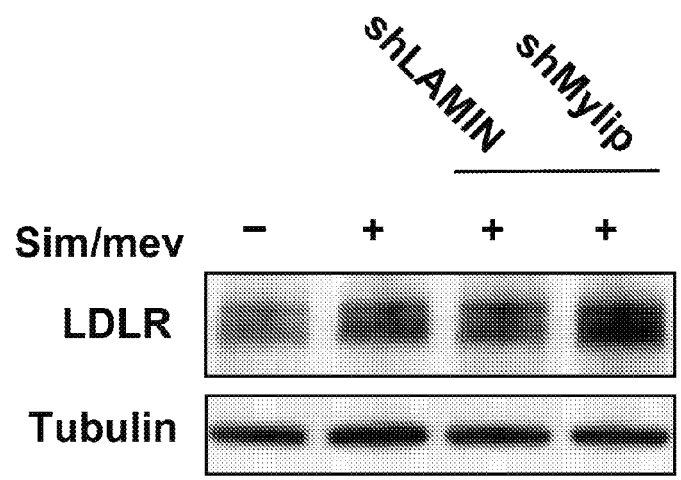

We next sought to determine whether Mylip expression could recapitulate the functional effects of LXR activation on LDL uptake. Indeed, expression of Mylip in MEFs from an adenoviral vector dramatically reduced LDL binding and uptake (FIG. 2H). Conversely, introduction of two independent shRNAs targeting mouse Mylip into MEFs increased LDLR protein without affecting LDLR mRNA (FIG. 2I and FIG. 8A). Importantly, the magnitude of the change in LDLR expression we observed following Mylip knockdown was comparable to that observed following inhibition of endogenous sterol production by statins (FIG. 8B). This observation suggests that modulation of Mylip activity is a physiological mechanism for regulating LDLR abundance.

In support of this idea, introduction of either Mylip shRNA construct into MEFs increased LDL uptake (FIG. 2J). Finally, the ability of an LXR ligand to reduce LDLR protein levels was substantially diminished when Mylip expression was knocked down, directly implicating Mylip in LXR-dependent regulation of LDLR expression (FIG. 2K).

Having identified Mylip as a regulator of LDLR expression, we endeavored to determine its mechanism of action. The data above suggest that a post-transcriptional event is involved. Pulse-chase labeling studies showed that Mylip did not block LDLR message translation or appearance of the immature protein, but it markedly reduced abundance of the mature form, pointing to a post-translational degradation event (FIG. 3A). The fact that mutation of the RING domain inactivates Mylip (FIG. 2E) implicates the E3 ligase activity in its mechanism of action. But what is the protein target for Mylip-directed ubiquitination? The most straightforward explanation for our data is that Mylip triggers ubiquitination of the LDLR itself, thereby marking it for degradation. The LDLR has not previously been shown to be ubiquitinated; however, to our knowledge this possibility has not been examined in contexts where LXR signaling or Mylip were specifically altered. We found that although basal polyubiquitination of the LDLR in 293T cells was minimal, it was dramatically enhanced by expression of active but not mutant Mylip (FIG. 3B).

Figure 9A:
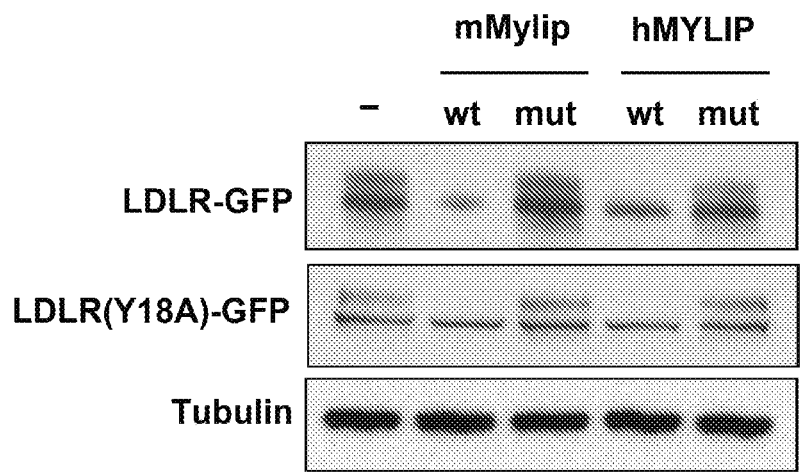
FIGS. 9A and 9B show the effect of Mylip on LDLR protein expression.
Figure 9B:
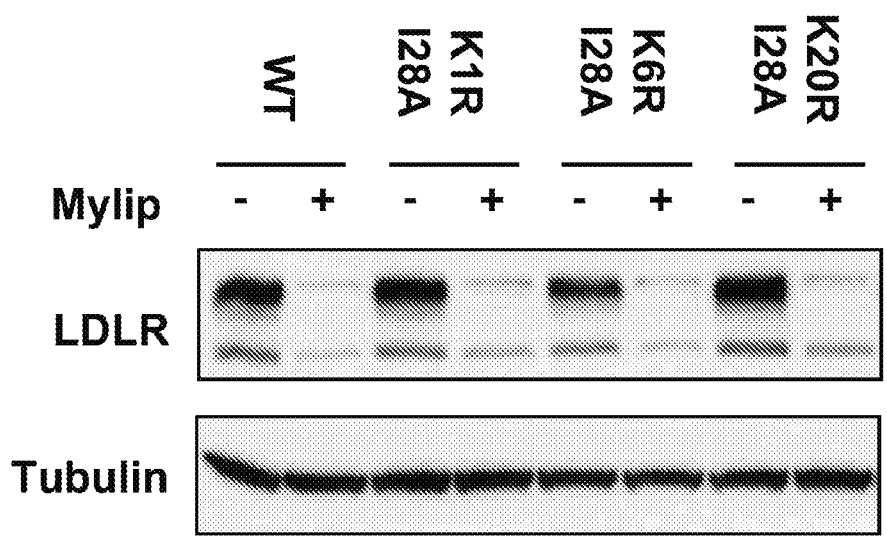

Next, we determined the structural requirements for LDLR degradation by Mylip. The 50 amino acid cytoplasmic tail of the LDLR links it to the endocytic machinery and cytoplasmic adapter proteins (Gotthardt et al. (2000) *J Biol Chem* 275: 25616). Mylip action on the LDLR was independent of the NPXY endocytosis motif in the cytoplasmic tail, because Mylip effectively reduced expression of an LDLR mutant (Y18A) defective in endocytosis (FIG. 9A) (Hunziker et al. (1991) *Cell* 66: 907). However, Mylip had no effect on an LDLR receptor lacking the entire intracellular domain (FIG. 3C). Typically, ubiquitination occurs on lysine residues, however, some membrane receptors have recently been demonstrated to be ubiquitinated on cysteine residues (Cadwell and Coscoy (2005) *Science* 309: 127). The LDLR intracellular domain contains 3 highly conserved lysines and one cysteine (FIG. 3D). We generated a panel of single and compound mutants of these LDLR residues and tested their effects on Mylip action. Remarkably, single mutations of any of these residues, or even loss of all three lysine residue, did not prevent Mylip from degrading the LDLR (FIG. 3E). However, superimposing the cysteine mutation on constructs containing two or three mutated lysines rendered the LDLR insensitive to degradation. To further narrow down the residues targeted by Mylip, we generated additional combined lysine and cysteine mutations (FIG. 3F). This analysis revealed that either an intact K20 or an intact C29 was required for Mylip mediated degradation. Only when these two residues were mutated together was Mylip action substantially blocked. Combined mutations of any of the three lysines with a mutation in 158, adjacent to C59, had no effect (FIG. 9B). Notably, both K20 and C29 are highly conserved among species, suggesting that the Mylip regulatory circuit may also be conserved (FIG. 3D). Finally, not only did combined mutation of the K20 and C29 residues block LDLR degradation by Mylip, it also blocked ubiquitination (FIG. 3G). Interestingly, the proteosome blocker MG132, despite greatly stabilizing Mylip expression, did not increase the Mylip-dependent level of LDLR ubiquitination. This observation is consistent with previous reports suggesting that degradation of the LDLR does not occur in the proteosome (FIG. 3G). These results strongly support the hypothesis that reduction of LDLR protein by Mylip involves directed ubiquitination of the cytoplasmic domain.

To study the physiological function of Mylip in vivo we transduced mice with adenoviral vectors encoding LacZ or mouse Mylip. Analysis of serum AST and ALT levels showed no evidence of hepatotoxicity due to viral infection (data not shown).

Figure 4A:
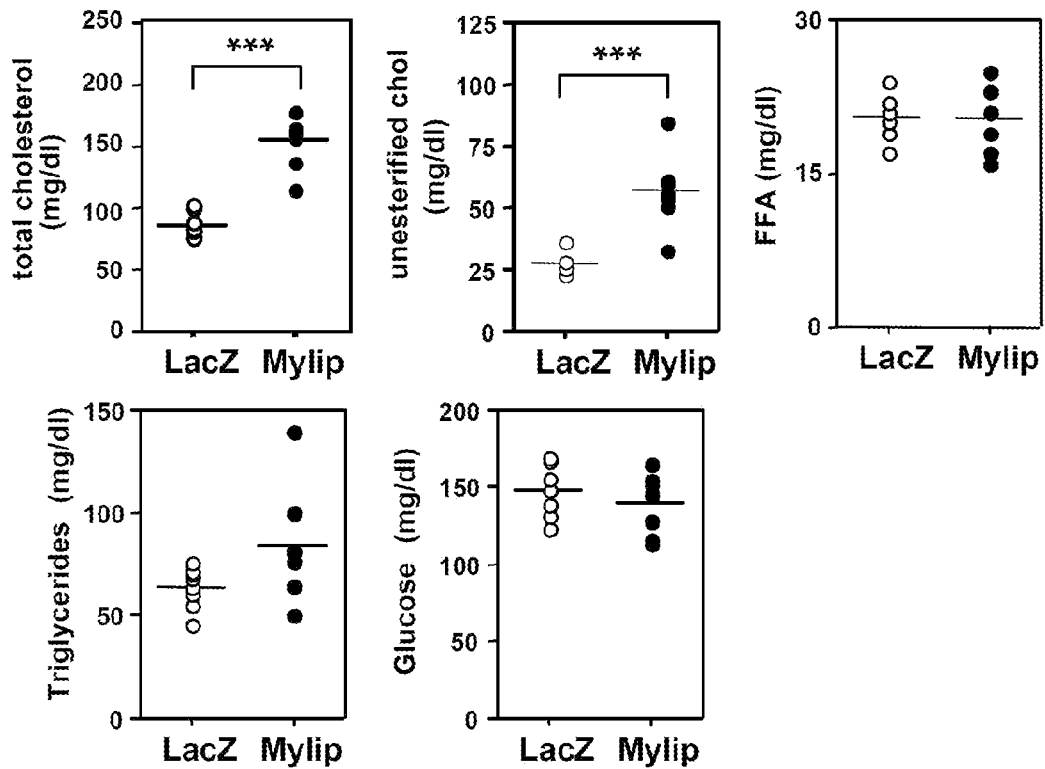
Figure 4B:
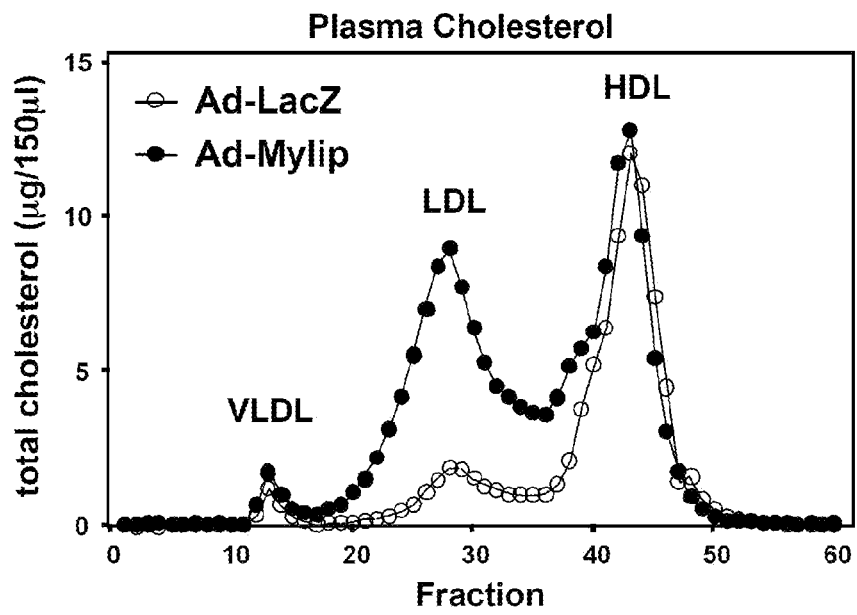
Figure 4F:
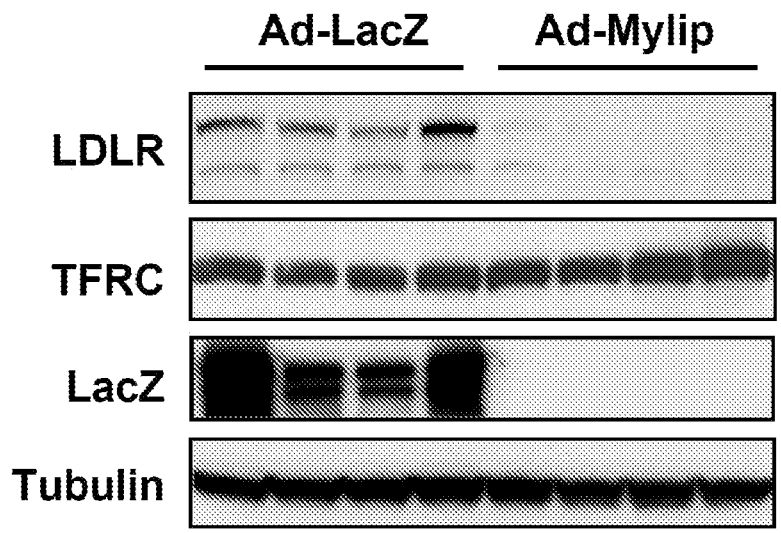
Figure 4G:
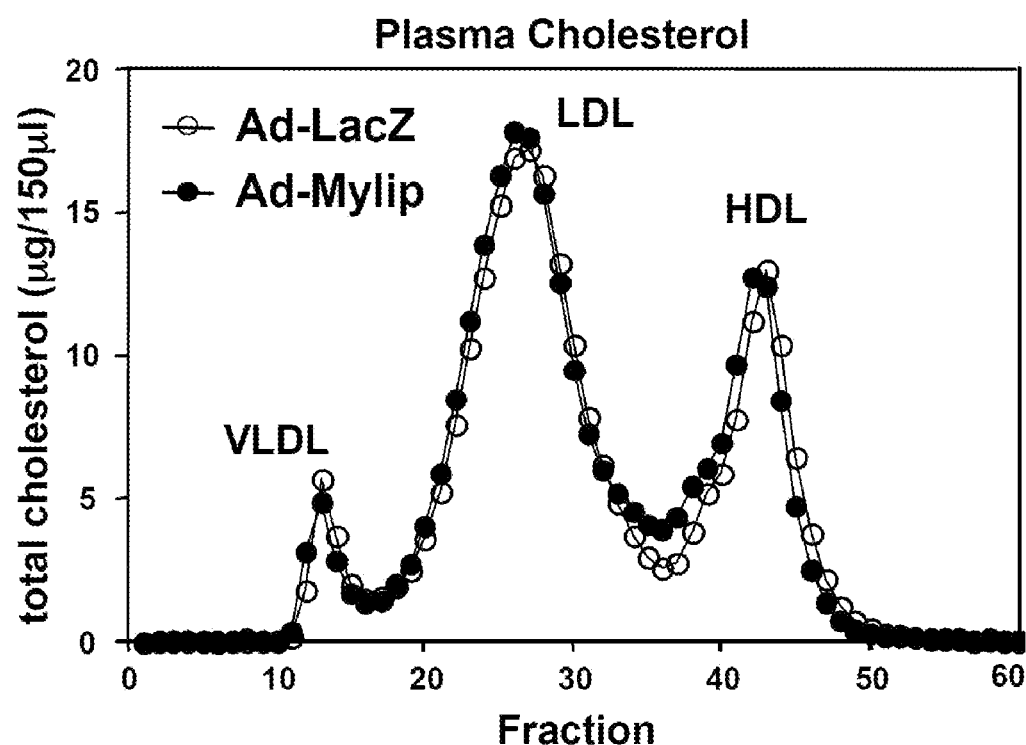
Figure 10A:
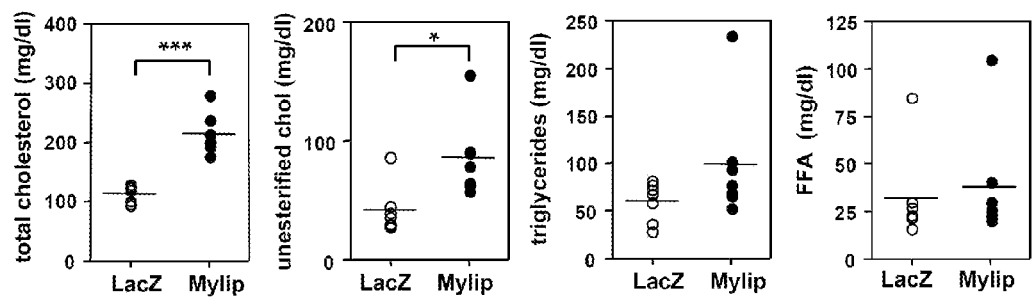
Figure 10B:
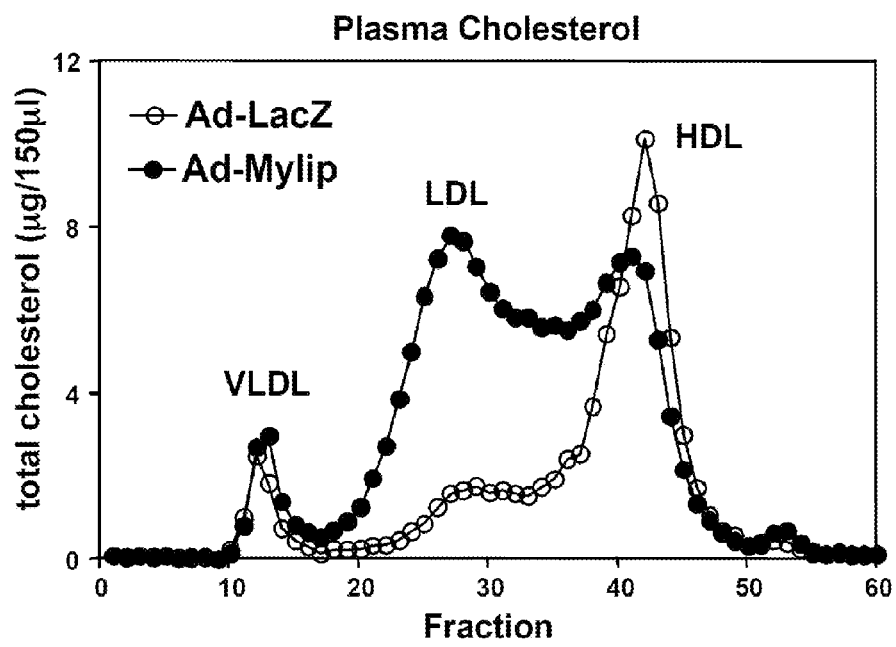
Figure 10C:
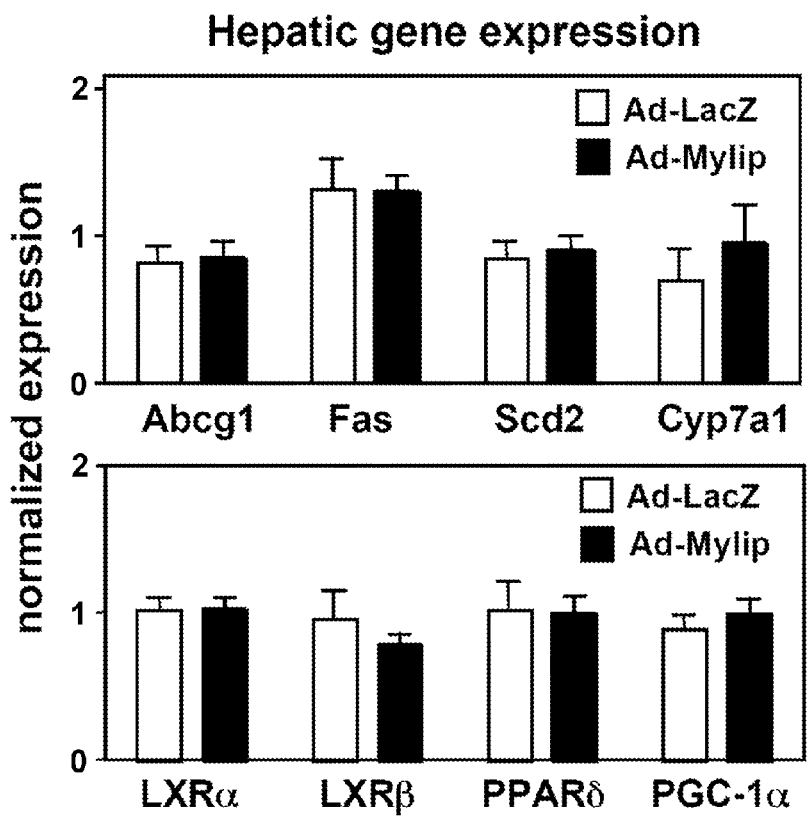
Figure 10D:
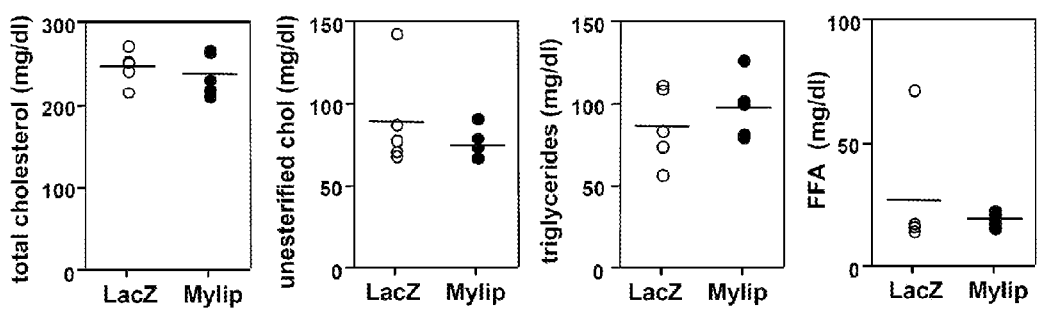

Remarkably, Mylip expression resulted in a striking increase in plasma levels of total and unesterified cholesterol (FIG. 4A). Levels of triglycerides, free fatty acids and glucose were not altered significantly. Fractionation of plasma revealed that Mylip expression caused a phenotype reminiscent of Ldlr$^{(-/-)}$ mice, characterized by a dramatic shift in the lipoprotein profile and the appearance of an LDL peak not present in the control mice (FIG. 4B). A slight increase in triglyceride content in the LDL-containing fractions was also observed (FIG. 4C). Western blotting confirmed the presence of apoB in this peak (FIG. 4D). Consistent with our in vitro results, hepatic expression of LXR and SREBP-2 target genes was not affected by Mylip expression (FIG. 4E). Rather, Mylip strongly reduced hepatic LDLR protein levels, providing a straightforward explanation for the appearance of an LDL fraction (FIG. 4F). By contrast, transferrin receptor expression was not altered by Mylip. An independent in vivo experiment showing virtually identical results is presented in FIGS. 10A-10C. Finally, Mylip adenovirus had no effect on plasma cholesterol levels or lipoprotein profiles or cholesterol levels of Ldlr$^{(-/-)}$ mice, unequivocally demonstrating that Mylip action is dependent on the LDLR (FIG. 4G, FIG. 10D, and FIG. 10E).

We have shown here that the sterol-sensitive nuclear receptor LXR regulates LDLR-dependent cholesterol uptake through a pathway independent of and complementary to the SREBPs. Activation of LXR induces expression of Mylip, which in turn catalyzes the ubiquitination of the LDLR, thereby targeting it for degradation. Our results offer a mechanistic explanation for an under-appreciated observation made two decades ago by Witztum and colleagues, who documented regulation of an ectopically-expressed LDLR by sterols (Sharkey et al. (1990) *J Lipid Res* 31: 2167). The physiological relevance of the LXR-Mylip-LDLR pathway is clear from our demonstrations that blocking endogenous Mylip expression promotes LDL uptake and that mice overexpressing Mylip in their livers phenocopy LDLR-/- mice.

Mechanistically we have established that Mylip triggers ubiquitination of the LDLR on K20 and C29 and that these residues are required for Mylip-dependent degradation. However, further study will be required to fully define the degradation pathway. Inhibition of the proteosome does not lead to the accumulation of poly-ubiquitinated LDLR, even when active Mylip is present. This suggests that Mylip-driven LDLR degradation is non-proteosomal, similar to what has been reported for Pcsk9 (Maxwell et al. (2005) *Proc. Natl. Acad. Sci., USA,* 102: 2069). Ubiquitination of membrane receptors can serve as a trafficking signal to direct proteins to specific organelles (Bonifacino and Traub (2003) *Annu Rev Biochem* 72: 395). It is therefore tempting to postulate that Mylip may act along the route LDLR traffics within the cell to direct it to a specific organelle(s) where it is degraded.

Another important issue to be resolved is the potential relationship between the Pcsk9 and Mylip pathways. Pcsk9 is a secreted protein induced by SREBP activation that may serve as a feedback inhibitor of SREBP action on the LDLR (Park et al. (2004) *J Biol Chem* 279: 50630; Maxwell et al. (2005) *Proc. Natl. Acad. Sci., USA,* 102: 2069). Pcsk9 binds to the LDLR extracellular ligand-binding domain, causing its removal from the cell surface and degradation. As Pcsk9 is a secreted protein and Mylip is cytoplasmic, it is unlikely that these proteins interact directly. However, despite extensive studies of Pcsk9-mediated LDLR degradation, the cellular location and mechanism of degradation are still unclear. An exciting but as yet unexplored possibility is that Mylip may act downstream of Pcsk9 in the same pathway to regulate LDLR expression.

Our identification of the Mylip-LDLR pathway fills a significant gap in our understanding of how LXRs control cholesterol homeostasis. The ability of LXRs to respond to excess cellular cholesterol by promoting efflux through ABC transporters has been extensively documented (Zelcer and Tontonoz (2006) *J Clin Invest* 116: 607). It makes intuitive sense that a sterol-activated transcription factor might also be employed to limit LDL cholesterol uptake, but this has not been described previously. The LXR-Mylip-LDLR pathway provides such a mechanism. Our results further illustrate how the two major sterol-regulated transcriptional factors, SREBP and LXR, act in a complementary and coordinated fashion to maintain cholesterol homeostasis. In fact, it may be very difficult to separate the components of these pathways in physiological contexts. Most endogenous oxysterol ligands of LXR inhibit SREBP processing. SREBP activation promotes LDLR expression, but also induces expression of the inhibitor Pcsk9. Systemic activation of LXR not only induces Mylip, but also promotes cholesterol efflux, induces SREBP-1c expression, stimulates bile acid synthesis, and blocks intestinal cholesterol absorption. Interestingly, LXR ligands have been reported to raise LDL levels in hamsters and primates and Mylip may be a contributor to this effect (Groot et al. (2005) *J Lipid Res* 46: 2182).

The LDL pathway is a validated target for cardiovascular therapy. Statin drugs act primarily by increasing hepatic expression of the LDLR, leading to increased LDL clearance. The possibility that pharmacologic targeting of the Mylip pathway provides a complementary strategy for increasing LDLR expression is intriguing. Indeed, Pcsk9 is being actively investigated as such a complementary target. In support of this idea, we have shown that knockdown of endogenous Mylip expression using siRNAs increases both LDLR expression and LDL uptake. Moreover, the fact that Mylip is an enzyme potentially opens the door for the development of small molecule inhibitors. The discovery that the enzymatic activity of Pcsk9 was not required for its action was disappointing from a drug development standpoint. By contrast, Mylip's E3 ligase activity appears critical for its action on the LDLR.

Abbreviations
  Liver X Receptors; LXRs
  LDL receptor; LDLR
  Myosin Light Chain Interacting Protein; Mylip
  LXR response element; LXRE
  mouse embryonic fibroblasts; MEFs
Materials & Methods
  Reagents The synthetic LXR ligands GW3965 and T0901317 were provided by T. Wilson (GlaxoSmithKline). MG132, Mevalonic acid, and 22R-hydroxycholesterol were from Sigma-Aldrich. Simvastatin sodium salt was from Calbiochem. BODIPY-LDL was purchased from Molecular Probes and fetal bovine lipoprotein deficient serum (LPDS) from Intracell.

Plasmids and Expression Constructs

The pEGFP-N3-hLDLR and its Y18A variant were a kind gift from Dr. A. Gonzalez (School of Medicine, Cassila, Chile) (Cancino et al. (2007) *Mol Biol Cell* 18: 4872). The non-tagged pCB6-hLDLR and its intracellular deletion mutant (pCB6-ΔhLDLR) were a kind gift from Dr. K. Matter (UCL, England) (Matter et al. (1992) *Cell* 71: 741). Site directed mutagenesis was used to introduce mutations in pCB6-hLDLR with the Quickchange multi-site mutagenesis kit (Stratagene). pEGFP-N1-hABCA1 was a kind gift of Dr. K. Ueda (Kyoto University, Japan) (Tanaka et al. (2003) *J Biol Chem* 278: 8815). The pEGFP-N1-hAPP and pEGFP-N1-light-chain-hLRP1 were a kind gift from Dr. B. Hyman (Harvard Medical School, USA) (Kinoshita et al. (2002) *J Neurochem* 82: 839). The pCDNA3.1-(HA-Ubiquitin)$_6$ was a kind gift from Dr. J. Wohlschlegel (UCLA, USA). The full-length human and mouse MYLIP cDNAs were amplified by PCR from IMAGE clone 3638617 and IMAGE clone 3964381, respectively, and cloned into the gateway entry plasmid pENTR1A (Invitrogen). The mMylip cDNA in IMAGE clone 3964381 contains 2 nucleotide changes from the mMylip reference sequence (NM_153789) that result in a P113A amino acid change. These two nucleotides were reverted to conform to the reference sequence using site directed mutagenesis. Additionally, a C387A mutation in the RING domain of both human and mouse MYLIP was introduced by site directed mutagenesis. To generate mammalian expression constructs for MYLIP we used LR recombination between MYLIP-containing pENTR1A and pDEST47 (Invitrogen). Restriction digest analysis and DNA sequencing were used to verify the correctness of all the constructs used in this study.

Mylip Promotor Analysis

A 10 Kb promotor region upstream of the mMylip transcription initiation site was analyzed for the presence of LXR binding elements. A consensus DR4 site was identified 2454 upstream of the transcription initiation site. Olignoucleotides encompassing this element were designed, annealed and tested for binding to LXR/RXR heterodimers in a standard EMSA assay. A 2.5 kB promotor fragment upstream of the transcription initiation site containing the identified LXRE was amplified by PCR from BAC clone RP23-17N24 using mMylip-prom-FWD GCTAGCCCTACTTAACCTACAAT-GACCT (SEQ ID NO:20) or mMylip-prom-ΔFWD GCTAGCTTCTGATGCTTCTACCTCTATC (SEQ ID NO:21) with the common antisense primer mMylip-prom-REV GAGCTCAGTTCCCGGGAGCTACACG (SEQ ID NO:22). Amplified fragments were cloned as SacI/XhoI fragments into pGL3 basic (Promega). Promotor analysis was done as previously described (Joseph et al. (2002) *J Biol Chem* 277: 11019).

Generation and Amplification of Adenoviral Particles

Ad-mMylip particles were generated by LR recombination of pENTR1A-mMylip and pAd/CMV/V5-DEST (Invitrogen). To generate Ad-shMylip virus we used the pAd-BLOCK-iT kit (Invitrogen) following the manufacturer's instructions. Briefly, oligonucleotides targeting 4 different regions of mMylip (see Table 2) were designed with proprietary software from Invitrogen and cloned into pU6-ENTR. The resulting pU6-mMylip$^{shRNA}$ plasmids were tested for their ability to inhibit mMylip expression in transient transfection experiments in HEK293T cells. The two constructs showing the greatest inhibition were LR recombined with pAD/BLOCK-iT-DEST (Invitrogen) to generate pAd-shMylip #1 and pAd-shMylip #2. Viruses used in this study were amplified, purified and tittered by Viraquest.

TABLE 2

Sequences of oligonucleotides used for constructing shRNA constructs.
All sequences target mMylip

| Name/Set | Sequence (5'-3') | SEQ ID NO |
|---|---|---|
| Set 1: | | |
| NZ#288-U6-1F | caccGGAGCAAAGGTGAGAGCTTAT*CGAA*ATAAGCTCTCACCTTTGCTCC | 23 |
| NZ#289-U6-1R | aaaaGGAGCAAAGGTGAGAGCTTAT*TTCG*ATAAGCTCTCACCTTTGCTCC | 24 |
| Set 2: | | |
| NZ#290-U6-2F | caccGCCTTAAACTGAGGGTCAAGT*CGAA*ACTTGACCCTCAGTTTAAGGC | 25 |
| NZ#291-U6-2R | aaaaGCCTTAAACTGAGGGTCAAGT*TTCG*ACTTGACCCTCAGTTTAAGGC | 26 |
| Set 3: | | |
| NZ#292-U6-3F | caccGGACAGCGAAGGACAGAAACT*CGAA*AGTTTCTGTCCTTCGCTGTCC | 27 |
| NZ#293-U6-3R | aaaaGGACAGCGAAGGACAGAAACT*TTCG*AGTTTCTGTCCTTCGCTGTCC | 28 |
| Set 4: | | |
| NZ#294-U6-4F | caccGCATCGTGCTCCTGTTTAAGA*CGAA*TCTTAAACAGGAGCACGATGC | 29 |
| NZ#295-U6-4R | aaaaGCATCGTGCTCCTGTTTAAGA*TTCG*TCTTAAACAGGAGCACGATGC | 30 |

Lower case: adaptor sequences for U6 plasmid
Normal: FWD complementary sequence
Italics: shRNA loop sequence
Underline: REV complementary sequence Cell Culture, Transfections and Adenoviral Infections The cell lines HEK293T, HepG2, and SV589 were obtained from ATCC. HEK293T were cultured in Optimem containing 2% FBS. HepG2 and SV589 were cultured in DMEM supplemented with 10% FBS. immortalized Lxrαβ$^{(-/-)}$ mouse embryonic fibroblasts (MEFs) were obtained by immortalizing E13.5 MEFs with a SV40 Large-T antigen retrovirus. To reconstitute mLxrα we transfected Phenix cells with pBabehygro or pBabehygro-mLxra. The resulting supernatant containing the corresponding retroviral particles was used to infect immortalized MEFs. Cells were selected in 800 μg/mL Hygromycin and surviving cells were used. HepG2-LDLR-GFP cells were generated by transfecting HepG2 cells with pEGFP-N1-LDLR and selecting cells with G418 (800 μg/mL).

Primary hepatocytes were isolated and maintained as previously reported (Pei et al. (2006) *Nat Med* 12: 1048). HEK293T cells were transfected using lipofectamine2000 (invitrogen). Typically, 0.8×10$^6$ cells were seeded in a 60 mm well and transfected the following day with 2 μg DNA. In experiments testing the ability of Mylip to degrade other potential protein targets a ratio of 3:1 (Mylip:target) was used. To infect MEFs and SV589 with adenovirus cells were seeded (0.2×10$^6$ cells/60 mm well) and infected the following day at an MOI of 300. HepG2 cells were infected at an MOI of 80. Primary hepatocytes were infected 4 hrs after plating at an MOI of 20. Infections were allowed to proceed for 18 hrs after which culture medium was replaced. Under these conditions more than 90% of the cells were transduced as assessed by GFP immunofluorescence. Where indicated, cells were subsequently sterol starved by incubating cells in DMEM supplemented with 10% LPDS, 5 μM Simvastatin, and 100 μM Mevalonic acid for an additional 18 hrs (sterol deficient medium).

LDL Uptake Assay

HepG2 cells were plated at density of 40,000 cells/well. On the following day the cells were pre-treated for 8 hrs with DMSO, 1 μM GW3965, or 1 μM T0901317 in DMEM supplemented with 10% FBS. MEFs (DKO-mLxra) were plated similarly and infected on the following day with the indicated adenovirus (MOI 300) for 18 hrs. Subsequently, cells were washed twice with PBS and incubated for an additional 16 hrs in sterol deficient medium to induce expression of the LDLR. In experiments with HepG2 cells the sterol deficient medium further contained the LXR synthetic ligands indicated above. Uptake was initiated by incubating cells in 200 μl of serum deficient medium containing 5 μg/mL of BODIPY-LDL. For measuring binding of BODIPY-LDL to cells, plates were placed on ice prior to processing. Uptake of BODIPY-LDL was measured after a 30 minute incubation period at 37° C. At that point cells were washed 2x with PBS containing 0.2% BSA and lysed in 100 μl RIPA buffer supplemented with protease inhibitors. Lysates were collected and cleared by centrifugation and 30 μl of cleared lysate was transferred into a 384 well plate and measured on a Typhoon apparatus (Amersham) with filters set for BODIPY. The protein concentration of the cleared lysates was determined and results are presented as relative fluorescence normalized for protein content.

RNA Isolation and Quantitative RT-PCR

Total RNA was isolated from cells and mouse tissues using Trizol (Invitrogen). One microgram of total RNA was reverse transcribed with random hexamers using iScript reverse transcription reagents kit (Biorad). Sybergreen (Diagenode) real-time quantitative PCR assays were performed using an Applied Biosystems 7900HT sequence detector. Results show averages of duplicate experiments normalized to 36B4. Sequences for qPCR primers are shown in Table 3.

TABLE 3 qPCR oligonucleotide pairs.

| Name/Set | Species | Sequence (5'-3') | SEQ ID NO |
|---|---|---|---|
| Human Set 1: | | | |
| NZ#179-hMYLIP-F | human | cgaggactgcctcaacca | 31 |
| NZ#180-hMYLIP-R | human | tgcagtccaaaatagtcaacttct | 32 |
| Human Set 2: | | | |
| NZ#284-hMYLIP new1-F | human | ttcttcgtggagcctcatct | 33 |
| NZ#285-hMYLIP new1-R | human | cctccttgatgtgcaagaaaa | 34 |
| Human Set 3: | | | |
| NZ#286-hMYLIP new2-F | human | atgaggagctctgtgccaag | 35 |
| NZ#287-hMYLIP new2-R | human | tccttatgttttgcaacaatgc | 36 |
| Mouse Set 1: | | | |
| bv-mMylip-458F | mouse | tgtggagcctcatctcatctt | 37 |
| bv-mMylip-526R | mouse | agggactctttaatgtgcaagaa | 38 |
| Mouse Set 2: | | | |
| NZ#197-mMylip(new1)-F | mouse | cagctatgaggacctgtgtgag | 39 |
| NZ#198-mMylip(new1)-R | mouse | tccttatgcttcgcaacgat | 40 |
| Mouse Set 3: | | | |
| NZ#199-mMylip(new2)-F | mouse | aggagatcaactccaccttctg | 41 |
| NZ#200-mMylip(new2)-R | mouse | atctgcagaccggacagg | 42 |

Antibodies, Immunoblot Analysis and Immunoprecipitation

Total cell or tissue lysates were prepared in RIPA buffer (150 mM NaCl, 1% NP-40, 0.1% Sodium Deoxycholate, 0.1% SDS, 100 mM Tris-HCl, pH 7.4) supplemented with protease inhibitors (Roche Molecular Biochemicals). Lysates were cleared by centriguation at 4° C. for 10 minutes at 10,000 g. Protein concentration of the cleared lysates was determined using the Bradford assay (Biorad) with BSA as reference. Samples (10-40 μg) were separated on NuPAGE Bis-Tris gels (Invitrogen) and transferred to nitrocellulose. Membranes were probed with the following antibodies: LDLR (Cayman chemical, 1:1000), ABCA1 (Novus, 1:1000), Tubulin (Calbiochem, 1:10000), HMGCR (rabbit anti-HMGCR polysera was a gift from Dr. Peter Edwards (Edwards et al. (1983) *J Biol Chem* 258: 7272), UCLA, 1:1000), GFP (affinity purified rabbit polyclonal anti-GFP was a gift from Dr. Mireille Riedinger, UCLA, 1:5000), TFRC (Zymed, 1:5000), MRLC (Cell Signaling, 1:1000) and poly-ubiquitin (Biomol, 1:1000). Polysera against MYLIP was raised in rabbits following immunization with a KLH-conjugated peptide corresponding to amino acids 316-329 of human and mouse MYLIP (Sigma-genosys) and used at a dilution of 1:1000. Appropriate secondary HRP-conjugated antibodies (DAKO) were used and visualized with chemiluminescence (ECL, Amersham). To immunoprecipitate LDLR-GFP, lysates were prepared as above and pre-cleared by incubation with Protein-A agarose beads (Santa Cruz) for 30 minutes. Subsequently, equal amounts of protein of cleared lysate were incubated with anti-GFP polysera (1:1000) for 30 minutes prior to addition of Protein-A agarose beads for an additional 16 hrs. For HA immunoprecipitations, equal amounts of protein of cleared lysates were incubated with EZ view red anti-HA affinity beads (Sigma) for 16 hrs. Subsequently, beads were washed 4× with RIPA buffer supplemented with protease inhibitors. All incubations and washes were done at 4° C. with rotation. Proteins were eluted from the beads by boiling in 1× protein sample buffer for 5 minutes.

Metabolic Labeling of Cells

HepG2-LDLR-GFP cells were infected with adenovirus as indicated above for 18 hrs. Subsequently, cells were washed 2× with PBS and pulsed for 30 minutes with DMEM lacking Methionine and Cysteine (MP-Biochemicals) supplemented with 200 μCi/well easy Tag express $^{35}$S protein labeling mix (Perkin Elmer). Cells were then washed 3× and chased in DMEM containing 10% FBS and 100 μg/mL Methionine and 500 μg/mL Cysteine for the indicated times. Preparation of cell lysates and immunoprecipitation of LDLR-GFP was conducted as detailed above.

Animal Experiments

C57BL/6 mice and C57BL/6 Ldlr$^{(-/-)}$ mice (Jackson Laboratoryfed) were fed a standard chow diet and housed in a temperature-controlled room under a 12-hour light/12-hour dark cycle under pathogen-free conditions. For adenoviral infections, age-matched (8-10 weeks old) male mice were injected with 1.5×E109 PFU by tail-vein injection. Mice were sacrificed 6 days later following a 6 hr fast. At the time of sacrifice liver tissue and blood was collected by cardiac-puncture and immediately frozen in liquid nitrogen and stored at −80° C. Liver tissue was processed for isolation of RNA and protein as above. Plasma lipids were determined as previously reported. Animal experiments were conducted in accordance with the UCLA Animal Research Committee.

Statistical Aanalysis

Real-time PCR data, LDL-uptake assays, and plasma lipid parameters are expressed as mean±standard deviation. Statistical analysis was done with a two-tailed Student's t-test. A probability value of $p<0.05$ was considered statistically significant.

Example 2

Further Studies

Generation and Validation of Idol−/− Cells as an Independent Screening Method.

Figure 12A:
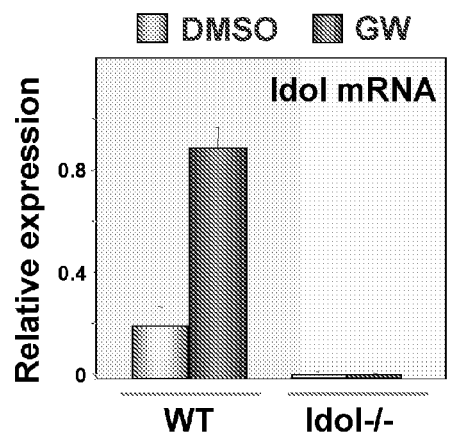
FIGS. 12A and 12B show data regarding the generation and validation of homozygous knockout Idol ES cells.
Figure 12B:
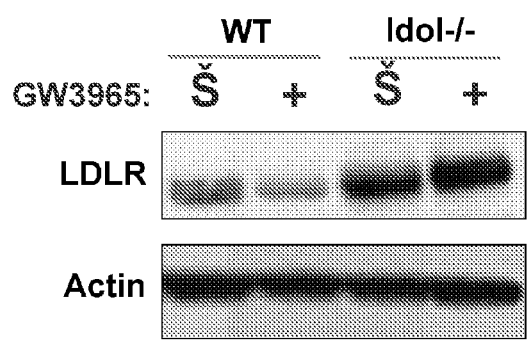

We have generated homozygous Idol−/− ES cells from our targeted heterozygous ES clones through high dose G418 selection. As shown in FIG. 12A, these cells completely lack expression of Idol mRNA. Interestingly, basal and LXR-dependent expression of LDLR protein is markedly altered in the genetic absence of Idol. The Idol−/− ES cells express significantly higher levels of LDLR protein (FIG. 12B).

We propose a screen for small molecules that affect the Idol pathway based on the Idol−/− cells. WT and Idol−/− are screened for response to candidate small molecules. The effect of Idol-specific small molecules will be lost in the Idol−/− cells. This screening method will be used in conjunction with the cell-based reporter screens described previously.

Identification of the Idol-LDLR Recognition Sequence.

Figure 13:
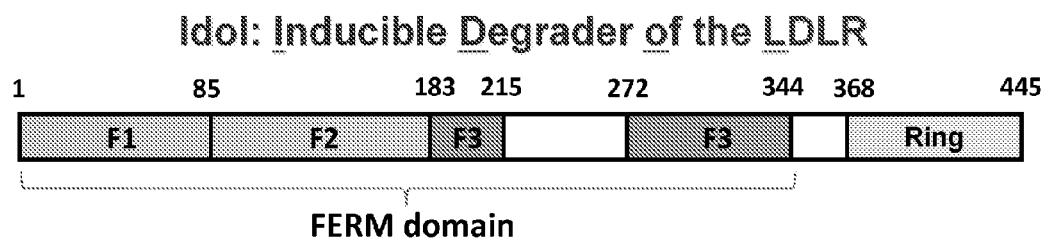
FIG. 13 illustrates the domain structure of Idol (mylip). The protein contains an N-terminal FERM protein-protein interaction domain and a C-terminal RING domain characteristic of E3 ubiquitin ligases.
Figures 14, 15:
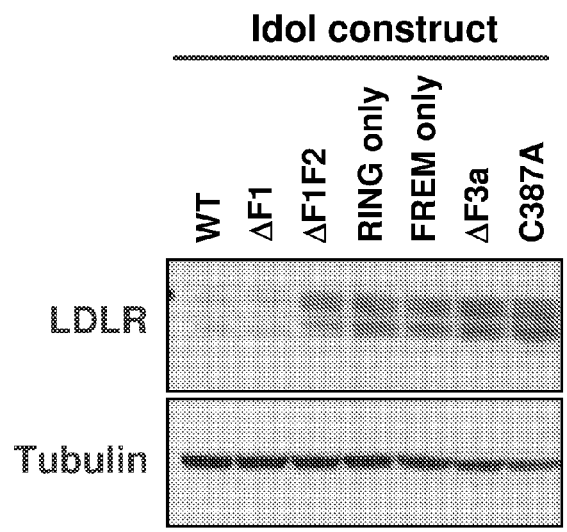
FIG. 14 shows the results of an analysis of Idol functional domains. HEK293 cells were transiently transfected with LDLR and/or WT or mutant Idol constructs as indicated. LDLR expression was determined by immunoblotting. C387A is a point mutation that inactivates the RING domain.
FIG. 15 shows an alignment of cytoplasmic tails of candidate membrane protein targets of Idol. Ubiquitination sites in the LDLR are shown in the areas labeled with asterisks. The NPVY internalization signal shown in the box labeled with ▲ highlighted blue. Other regions of sequence similarity are in the boxes labeled with Δ. LDLR (SEQ ID NO:10), VLDLR (SEQ ID NO:11), apoER2 (SEQ ID NO:12), LRP1B (SEQ ID NO:13), LRP1 (SEQ ID NO:14), EGFR (SEQ ID NO:15).

Our data indicate that the FERM domain interacts directly with the cytoplasmic tail of the LDLR and provides target recognition, while the RING domain is essential for E3 ligase activity. Since Idol is the only protein in the mammalian genome with both FERM and RING domains, this model provides an attractive explanation for the specificity of Idol effects and can be used as the basis to screen for inhibitors. The Idol FERM domain is predicted to contain 4 distinct loops (F1, F2, F3 and F3a; FIG. 13). We have determined that both the FERM and RING domains are required for Idol action on the DLR (FIG. 14). In addition, the F1 loop of Idol is dispensable for LDLR degradation, but the F3a loop, which is unique to Idol and not present other FERM domains, is essential (FIG. 14).

Furthermore, as shown in FIG. 15, the two proteins most closely related by sequence to the LDLR, the VLDLR and apoER2, are both capable of being degraded by Idol in our cotransfection assay. Several other members, including LRP-1, LRP-1b and the EGFR receptor are not. Based on these results, we can conclude that neither the NPVY internalization motif, nor the presence of the LDLR lysine or cysteine ubiquitination sites are sufficient to confer Idol recognition. Rather, the residues conserved between LDLR, VLDLR and apoER2 are important for Idol recognition. We have further determined that the FERM domain of Idol is critical for interaction with the LDLR. Disruption of Idol FERM domain interaction with these LDLR residues using a small molecule would inactivate the Idol-LDLR pathway.

The Idol-LDLR recognition sequence can be used as the basis for a screen aimed at identifying small molecules that specifically disrupted Idol-LDLR interaction by targeting this region of the LDLR.

Use of Idol Transgenic and Knockout Mice as the Basis of Screens for Small Molecules Targeting the Idol Pathway.

Figure 16:
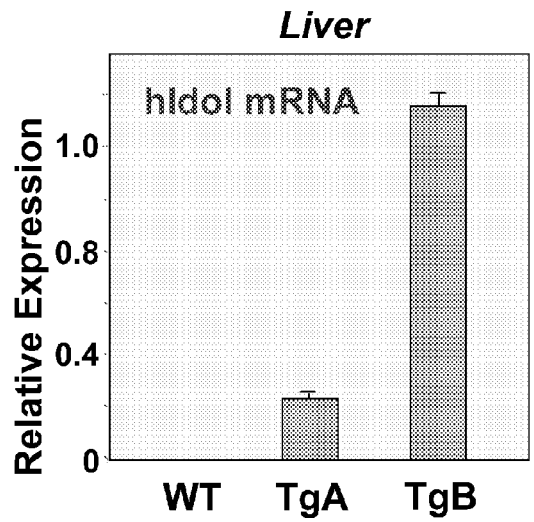
FIG. 16 shows data illustrating the validation of liver-specific Idol transgenic mice. Expression of human transgene specific Idol expression in livers of Albumin-Idol Tg mice determined by realtime PCR.

We have generated transgenic (Tg) mice that express human Idol from the liver-specific albumen promoter. We have established two independent lines and confirmed that these mice express human Idol specifically in their livers (FIG. 16). Quantitative realtime PCR has established that line A expresses approximately 2× more Idol mRNA compared to C57B1/6 mice and line B expresses approximately 6× more Idol mRNA (not shown). These mice can be used to validate small molecule, shRNA, siRNA or antisense Idol modulators.

Figure 17:
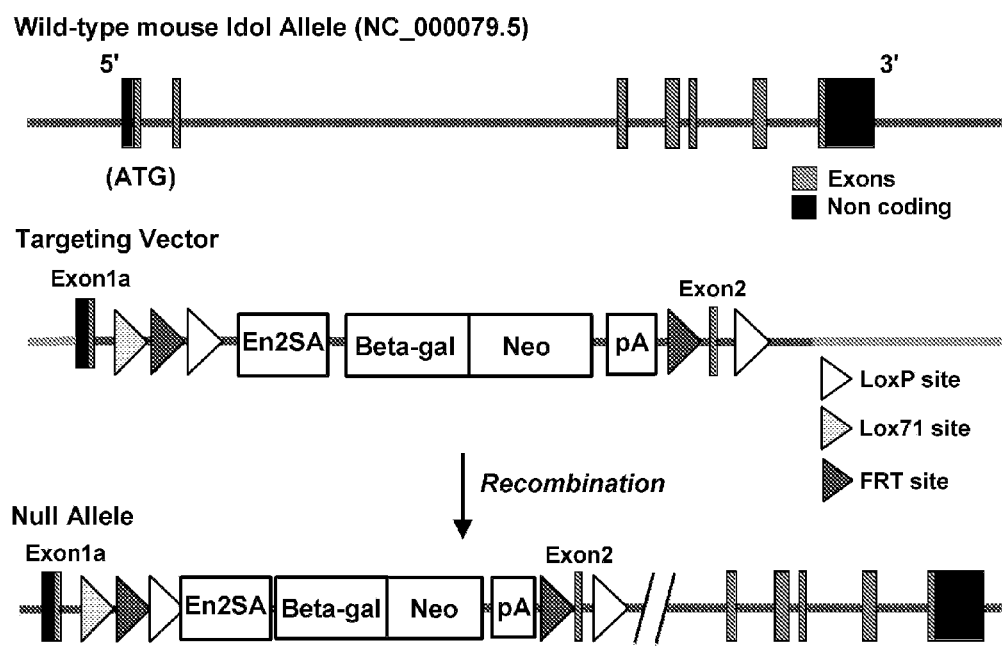
FIG. 17 illustrates a knockout strategy for the mouse Idol locus. The targeting vector is conditional-ready and the null allele can be converted to a floxed allele by crossing with FLIP-expressing mice. This will yield an allele with exon2
Figure 18:
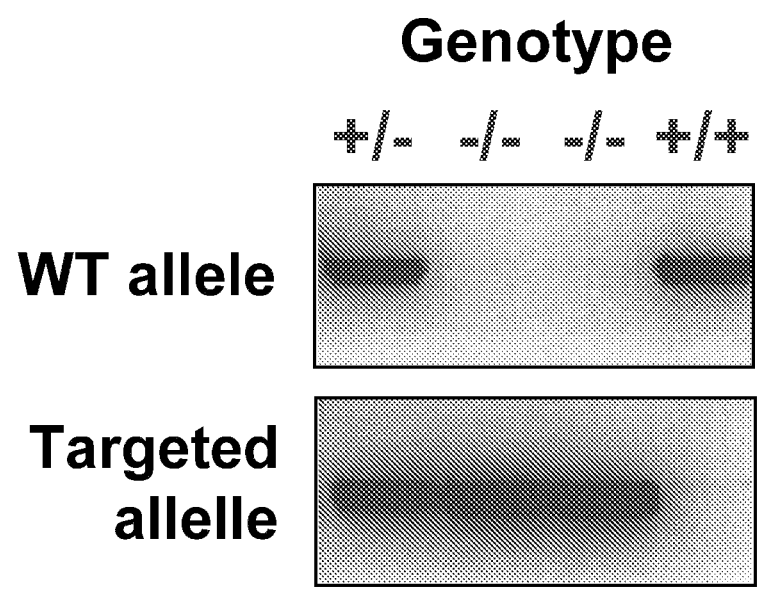
FIG. 18 shows data from the PCR validation of Idol null mice. Tail DNA was analyzed by PCR for the presence of WT and null Idol alleles.

We have also generated Idol knockout mice using the targeting strategy shown in FIG. 17. Crosses of Idol−/+ mice have yielded pups of all three expected genotypes at approximately Mendelian ratios (FIG. 18). Thus, the global Idol null mice are viable and available for use in screens of small molecule, shRNA, siRNA, or antisense Idol modulators.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A method of screening for an agent that inhibits low density lipoprotein (LDL) receptor degradation, or that promotes LDL uptake, or that inhibits low density lipoprotein (LDL) receptor degradation and promotes LDL uptake in a mammal, said method comprising:
   contacting a plurality of test agents, each to a plurality of cells;
   detecting the expression or activity of myosin light chain interacting protein (Mylip) in said cells; and
   scoring test agents that decrease Mylip expression or activity, as compared to the expression or activity of myosin light chain interacting protein (Mylip) in a control as test agents that inhibit LDL receptor degradation, or that promote LDL uptake, or that inhibit LDL receptor degradation and promote LDL uptake in a mammal.

2. The method of claim 1, wherein said detecting comprises detecting expression of a reporter gene whose expression is regulated by the Mylip promoter.

3. The method of claim 1, wherein the expression of Mylip is detected by detecting Mylip mRNA from said cell.

4. The method of claim 3, wherein said level of Mylip mRNA is measured by hybridizing said mRNA to a probe that specifically hybridizes to a Mylip nucleic acid.

5. The method of claim 1, wherein said detecting the expression or activity of myosin light chain interacting protein (Mylip) comprises detecting the activity of Mylip on an LDL receptor.

6. The method of claim 1, wherein said detecting the expression or activity of myosin light chain interacting protein (Mylip) comprises detecting Mylip auto-degradation.

7. The method of claim 1, wherein said detecting the expression or activity of myosin light chain interacting protein (Mylip) comprises detecting LDL uptake where an increase in LDL uptake is an indicator of Mylip inhibition.

8. A method of screening for an agent that inhibits low density lipoprotein receptor (LDLR) degradation and/or promotes low density lipoprotein (LDL) uptake in a mammal, said method comprising:
   contacting an LDLR or a fragment thereof comprising the amino acid residues that interact with an Idol protein or a fragment thereof comprising a FERM domain (F for 4.1 protein, E for ezrin, R for radixin and M for moesin) with a test agent;
   detecting interaction or binding of the LDLR with said Idol protein or fragment; and
   scoring moieties that reduce or block LDLR/Idol interaction or binding as agents that inhibit LDL receptor degradation and/or promote LDL uptake in a mammal.

9. The method of claim 1, wherein said test agents are small organic molecules.

10. The method of claim 9, wherein said test agent is a small organic molecule.

* * * * *

UNITED STATES PATENT AND TRADEMARK OFFICE
CERTIFICATE OF CORRECTION

Page 1 of 1

PATENT NO.            : 8,512,964 B2
APPLICATION NO.       : 13/132296
DATED                 : August 20, 2013
INVENTOR(S)           : Tontonoz et al.

It is certified that error appears in the above-identified patent and that said Letters Patent is hereby corrected as shown below:

SPECIFICATION:

1. Column 1, lines 15-18, change "This invention was made with Government support under Grant No. R01 HL066088, awarded by the National Institutes of Health. The Government has certain rights in this invention." to -- This invention was made with Government support under Grant No. HL066088 awarded by the National Institutes of Health. The Government has certain rights in the invention. --.

Signed and Sealed this
First Day of April, 2014

Michelle K. Lee
*Deputy Director of the United States Patent and Trademark Office*